US012637694B2

(12) United States Patent
Schambach et al.

(10) Patent No.: US 12,637,694 B2
(45) Date of Patent: May 26, 2026

(54) ALL-IN ONE VECTOR FOR CAR AND THERAPEUTIC EFFECTOR MOLECULE

(71) Applicant: Medizinische Hochscule Hannover, Hannover (DE)

(72) Inventors: Axel Schambach, Hannover (DE); Katharina Zimmermann, Hannover (DE); Hinrich Abken, Geiselhöring (DE); Johannes Kühle, Cologne (DE)

(73) Assignee: Medizinische Hochschule Hannover, Hannover (DE)

( * ) Notice: Subject to any disclaimer, the term of this patent is extended or adjusted under 35 U.S.C. 154(b) by 1191 days.

(21) Appl. No.: 17/619,789

(22) PCT Filed: Jun. 22, 2020

(86) PCT No.: PCT/EP2020/067380
§ 371 (c)(1),
(2) Date: Dec. 16, 2021

(87) PCT Pub. No.: WO2020/254694
PCT Pub. Date: Dec. 24, 2020

(65) Prior Publication Data
US 2023/0142916 A1 May 11, 2023

(30) Foreign Application Priority Data

Jun. 21, 2019 (EP) .................................... 19181837

(51) Int. Cl.
| | |
|---|---|
| *C12N 15/86* | (2006.01) |
| *A61K 35/17* | (2025.01) |
| *A61K 40/11* | (2025.01) |
| *A61K 40/15* | (2025.01) |
| *A61K 40/17* | (2025.01) |
| *A61K 40/24* | (2025.01) |
| *A61K 40/31* | (2025.01) |
| *A61K 40/42* | (2025.01) |
| *C07K 14/705* | (2006.01) |
| *C07K 14/725* | (2006.01) |
| *A61K 39/00* | (2006.01) |

(52) U.S. Cl.
CPC .............. *C12N 15/86* (2013.01); *A61K 40/11* (2025.01); *A61K 40/15* (2025.01); *A61K 40/17* (2025.01); *A61K 40/24* (2025.01); *A61K 40/31* (2025.01); *A61K 40/4258* (2025.01); *A61K 40/4266* (2025.01); *C07K 14/7051* (2013.01); *C07K 14/70521* (2013.01); *C07K 14/70578* (2013.01); *A61K 2039/55538* (2013.01); *C07K 2319/02* (2013.01); *C07K 2319/33* (2013.01)

(58) Field of Classification Search
CPC ........ C12N 15/86; A61K 40/11; A61K 40/15; A61K 40/31; C07K 14/7051; C07K 2319/33; C07K 2319/00; C07K 2319/03
See application file for complete search history.

(56) References Cited

U.S. PATENT DOCUMENTS 8,556,882 B2 * 10/2013 Morgan ............. C07K 14/4702
604/522
2019/0112380 A1 4/2019 Chaudhary

FOREIGN PATENT DOCUMENTS

| | | |
|---|---|---|
| WO | 2017186121 A1 | 11/2017 |
| WO | 2018132494 A1 | 7/2018 |
| WO | 2019006468 A1 | 1/2019 |
| WO | 2019034703 A2 | 2/2019 |
| WO | 2019051424 A2 | 3/2019 |

OTHER PUBLICATIONS

Higashimoto, T., Urbinati, F., Perumbeti, A., Jiang, G., Zarzuela, A., Chang, L.J., Kohn, D.B. and Malik, P., 2007. The woodchuck hepatitis virus post-transcriptional regulatory element reduces readthrough transcription from retroviral vectors. Gene therapy, 14(17), pp. 1298-1304. (Year: 2007).*
Chmielewski et al., "CAR T Cells Releasing IL-18 Convert to T-Bet(high) FoxO1(low) Effectors that Exhibit Augmented Activity against Advanced Solid Tumors", Cell Reports, 2017, pp. 3205-3219, vol. 21, Cell Press.
Sakemura et al., "A Tet-On Inducible System for Controlling CD-19 Chimeric Antigen Receptor Expression upon Drug Administration", Cancer Immunology Research, 2016, pp. 658-668, vol. 4, No. 8, American Associate for Cancer Research.
Zimmermann et al., "Design and Characterization of an 'All-in-One' Lentiviral Vector System Combining Constitutive Anti-GD2 CAR Expression and Inducible Cytokines", Cancers, 2020, pp. 1-22, vol. 12, No. 375, MDPI.
Chmielewski et al., "CAR T cells transform to trucks: chimeric antigen receptor-redirected T cells engineered to deliver inducible IL-12 modulate the tumour stroma to combat cancer", Cancer Immunology Immunotherapy, 2012, pp. 1269-1277, vol. 61, Springer.
International Search Report and Written Opinion from the corresponding International Patent Application No. PCT/EP2020/067380, dated Sep. 8, 2020.

* cited by examiner (Continued)

Primary Examiner — Jeremy C Flinders
Assistant Examiner — Masudur Rahman
(74) *Attorney, Agent, or Firm* — Greer, Burns & Crain, Ltd.; Steven P. Fallon; E. Kate Berezutskaya

(57) ABSTRACT

Immune cells containing a nucleic acid construct, also referred to as a vector or viral vector, for use in immune therapy, e.g. for use in the treatment of cancer, or for use in the treatment of autoimmune disease, or for use in the treatment of GvH or HvG. The nucleic acid construct comprises a second expression cassette for constitutive expression of a CAR or a TCR, the binding of which to its target antigen results in signalling and induces the expression of an effector molecule from a first expression cassette, which is contained on the same nucleic acid construct, and which first expression cassette encodes the effector molecule under the control of a promoter inducible by signalling of the CAR or TCR.

20 Claims, 6 Drawing Sheets

Figures 1, 2, 3:
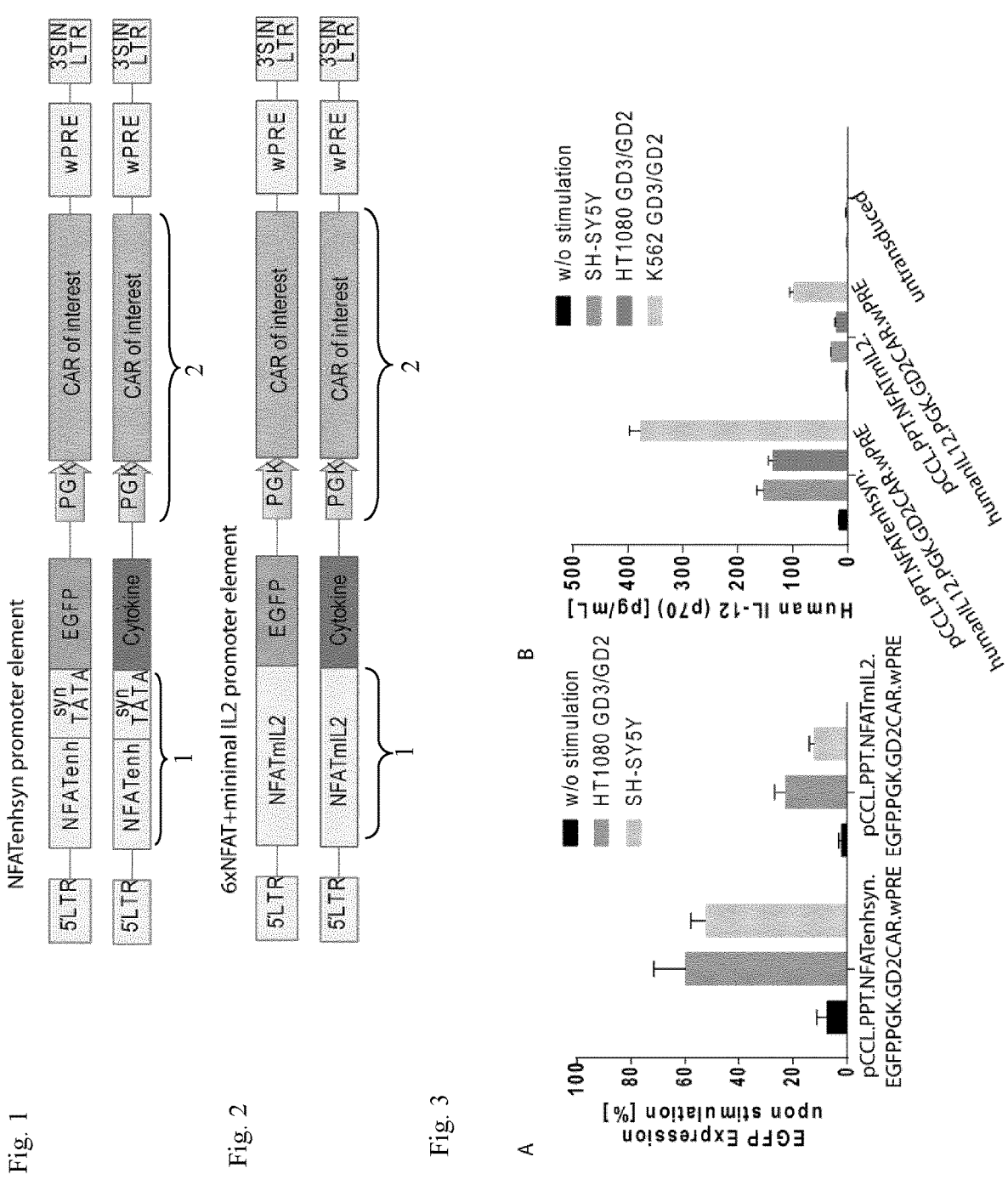

Specification includes a Sequence Listing.

SEQUENCE LISTING

```
<160> NUMBER OF SEQ ID NOS: 35

<210> SEQ ID NO 1
<211> LENGTH: 244
<212> TYPE: DNA
<213> ORGANISM: Artificial Sequence
<220> FEATURE:
<223> OTHER INFORMATION: NFATenhsyn promoter
<220> FEATURE:
<221> NAME/KEY: TATA_signal
<222> LOCATION: 202..208
<223> OTHER INFORMATION: /note="TATA box"

<400> SEQUENCE: 1
tggaggaaaa actgtttcat acagaaggcg tggaggaaaa actgtttcat acagaaggcg        60
tggaggaaaa actgtttcat acagaaggcg tggaggaaaa actgtttcat acagaaggcg       120
tggaggaaaa actgtttcat acagaaggcg tggaggaaaa actgtttcat acagaaggcg       180
tctgcaggag actctagagg gtatataatg gtttaaactt aagcttggta ccgggccccc       240
gaag                                                                     244

<210> SEQ ID NO 2
<211> LENGTH: 364
<212> TYPE: DNA
<213> ORGANISM: Artificial Sequence
<220> FEATURE:
<223> OTHER INFORMATION: NFATmIL2 promoter
<220> FEATURE:
<221> NAME/KEY: TATA_signal
<222> LOCATION: 291..297
<223> OTHER INFORMATION: /note="TATA box"

<400> SEQUENCE: 2
gatatcgaat taggaggaaa aactgtttca tacagaaggc gtcaattagg aggaaaaact        60
gtttcataca gaaggcgtca attaggagga aaaactgttt catacagaag gcgtcaattg       120
gtcccatcga attaggagga aaaactgttt catacagaag gcgtcaatta ggaggaaaaa       180
```

-continued

```
ctgtttcata cagaaggcgt caattaggag gaaaaactgt ttcatacaga aggcgtcaat      240
tggtcccggg acattttgac accccataa tattttttcca gaattaacag tataaattgc      300
atctcttgtt caagagttcc ctatcactct ctttaatcac tactcacagt aacctcaact      360
cctg                                                                   364

<210> SEQ ID NO 3
<211> LENGTH: 173
<212> TYPE: DNA
<213> ORGANISM: Artificial Sequence
<220> FEATURE:
<223> OTHER INFORMATION: NFN:Benhsyn promoter
<220> FEATURE:
<221> NAME/KEY: TATA_signal
<222> LOCATION: 131..137
<223> OTHER INFORMATION: /note="TATA box"

<400> SEQUENCE: 3
ctcgagggga atttccgggg actttccggg aatttccggg gactttccgg gaatttccgg       60
gaatttccgg ggactttccg ggaatttccg gggactttcc gggaatttcc ctgcaggaga      120
ctctagaggg tatataatgg tttaaactta agcttggtac cgggcccccg aag            173

<210> SEQ ID NO 4
<211> LENGTH: 1623
<212> TYPE: DNA
<213> ORGANISM: Artificial Sequence
<220> FEATURE:
<223> OTHER INFORMATION: IL-12 coding sequence
<220> FEATURE:
<221> NAME/KEY: CDS
<222> LOCATION: 1..1623
<223> OTHER INFORMATION: /note="synthetic coding sequence for IL-12"
      /transl_table=1

<400> SEQUENCE: 4 atg tgt cac cag cag ctg gtc atc agc tgg ttc agc ctg gtg ttc ctg        48
Met Cys His Gln Gln Leu Val Ile Ser Trp Phe Ser Leu Val Phe Leu
1               5                   10                  15 gcc tct cct ctg gtg gcc atc tgg gag ctg aag aaa gac gtg tac gtg        96
Ala Ser Pro Leu Val Ala Ile Trp Glu Leu Lys Lys Asp Val Tyr Val
                20                  25                  30 gtg gaa ctg gac tgg tat ccc gat gct cct ggc gag atg gtg gtg ctg       144
Val Glu Leu Asp Trp Tyr Pro Asp Ala Pro Gly Glu Met Val Val Leu
            35                  40                  45 acc tgc gat acc cct gaa gag gac ggc atc acc tgg aca ctg gat cag       192
Thr Cys Asp Thr Pro Glu Glu Asp Gly Ile Thr Trp Thr Leu Asp Gln
        50                  55                  60 tct agc gag gtg ctc ggc agc ggc aag acc ctg acc atc caa gtg aaa       240
Ser Ser Glu Val Leu Gly Ser Gly Lys Thr Leu Thr Ile Gln Val Lys
65                  70                  75                  80 gag ttt ggc gac gcc ggc cag tac acc tgt cac aaa ggc gga gaa gtg       288
Glu Phe Gly Asp Ala Gly Gln Tyr Thr Cys His Lys Gly Gly Glu Val
                85                  90                  95 ctg agc cac agc ctg ctg ctc ctc cac aag aaa gag gat ggc att tgg       336
Leu Ser His Ser Leu Leu Leu Leu His Lys Lys Glu Asp Gly Ile Trp
            100                 105                 110 agc acc gac atc ctg aag gac cag aaa gag ccc aag aac aag acc ttc       384
Ser Thr Asp Ile Leu Lys Asp Gln Lys Glu Pro Lys Asn Lys Thr Phe
        115                 120                 125 ctg aga tgc gag gcc aag aac tac agc ggc cgg ttc aca tgt tgg tgg       432
Leu Arg Cys Glu Ala Lys Asn Tyr Ser Gly Arg Phe Thr Cys Trp Trp
    130                 135                 140
```

-continued

```
ctg acc acc atc agc acc gac ctg acc ttc agc gtg aag tcc agc aga    480
Leu Thr Thr Ile Ser Thr Asp Leu Thr Phe Ser Val Lys Ser Ser Arg
145             150                 155                 160 ggc agc agt gat cct cag ggc gtt aca tgt ggc gcc gct aca ctg tct    528
Gly Ser Ser Asp Pro Gln Gly Val Thr Cys Gly Ala Ala Thr Leu Ser
                165                 170                 175 gcc gaa aga gtg cgg ggc gac aac aaa gaa tac gag tac agc gtg gaa    576
Ala Glu Arg Val Arg Gly Asp Asn Lys Glu Tyr Glu Tyr Ser Val Glu
            180                 185                 190 tgc caa gag gac agc gcc tgt cca gcc gcc gaa gag tct ctg cct atc    624
Cys Gln Glu Asp Ser Ala Cys Pro Ala Ala Glu Glu Ser Leu Pro Ile
        195                 200                 205 gaa gtg atg gtg gac gcc gtg cac aag ctg aag tac gag aac tac acc    672
Glu Val Met Val Asp Ala Val His Lys Leu Lys Tyr Glu Asn Tyr Thr
    210                 215                 220 tcc agc ttt ttc atc cgg gac atc atc aag ccc gat cct cca aag aac    720
Ser Ser Phe Phe Ile Arg Asp Ile Ile Lys Pro Asp Pro Pro Lys Asn
225                 230                 235                 240 ctg cag ctg aag cct ctg aag aac agc aga cag gtg gaa gtg tcc tgg    768
Leu Gln Leu Lys Pro Leu Lys Asn Ser Arg Gln Val Glu Val Ser Trp
                245                 250                 255 gag tac ccc gac acc tgg tct aca ccc cac agc tac ttc agc ctg acc    816
Glu Tyr Pro Asp Thr Trp Ser Thr Pro His Ser Tyr Phe Ser Leu Thr
            260                 265                 270 ttt tgc gtg caa gtg cag ggc aag tcc aag cgc gag aaa aag gac cgg    864
Phe Cys Val Gln Val Gln Gly Lys Ser Lys Arg Glu Lys Lys Asp Arg
        275                 280                 285 gtg ttc acc gac aag acc agc gcc acc gtg atc tgc aga aag aac gcc    912
Val Phe Thr Asp Lys Thr Ser Ala Thr Val Ile Cys Arg Lys Asn Ala
    290                 295                 300 agc atc agc gtc aga gcc cag gac cgc tac tac agc agc tct tgg agc    960
Ser Ile Ser Val Arg Ala Gln Asp Arg Tyr Tyr Ser Ser Ser Trp Ser
305                 310                 315                 320 gaa tgg gcc agc gtg cca tgt tct ggt ggc gga gga tct ggc gga ggt   1008
Glu Trp Ala Ser Val Pro Cys Ser Gly Gly Gly Gly Ser Gly Gly Gly
                325                 330                 335 gga agc ggc gga ggc gga tct aga aat ctg cct gtg gcc act cct gat   1056
Gly Ser Gly Gly Gly Gly Ser Arg Asn Leu Pro Val Ala Thr Pro Asp
            340                 345                 350 cct ggc atg ttc cct tgt ctg cac cac agc cag aac ctg ctg aga gcc   1104
Pro Gly Met Phe Pro Cys Leu His His Ser Gln Asn Leu Leu Arg Ala
        355                 360                 365 gtg tcc aac atg ctg cag aag gcc aga cag acc ctg gaa ttc tac ccc   1152
Val Ser Asn Met Leu Gln Lys Ala Arg Gln Thr Leu Glu Phe Tyr Pro
    370                 375                 380 tgc acc agc gag gaa atc gac cac gag gac atc acc aag gat aag acc   1200
Cys Thr Ser Glu Glu Ile Asp His Glu Asp Ile Thr Lys Asp Lys Thr
385                 390                 395                 400 agt acc gtg gaa gcc tgc ctg cct ctg gaa ctg acc aag aac gag agc   1248
Ser Thr Val Glu Ala Cys Leu Pro Leu Glu Leu Thr Lys Asn Glu Ser
                405                 410                 415 tgc ctg aac agc cgg gaa acc agc ttc atc acc aac ggc tct tgc ctg   1296
Cys Leu Asn Ser Arg Glu Thr Ser Phe Ile Thr Asn Gly Ser Cys Leu
            420                 425                 430 gcc agc aga aag acc tcc ttc atg atg gcc ctg tgc ctg agc agc atc   1344
Ala Ser Arg Lys Thr Ser Phe Met Met Ala Leu Cys Leu Ser Ser Ile
        435                 440                 445 tac gag gac ctg aag atg tac cag gtg gaa ttc aag acc atg aac gcc   1392
Tyr Glu Asp Leu Lys Met Tyr Gln Val Glu Phe Lys Thr Met Asn Ala
    450                 455                 460
```

-continued

```
aag ctg ctg atg gac ccc aag cgg cag atc ttc ctg gac cag aat atg      1440
Lys Leu Leu Met Asp Pro Lys Arg Gln Ile Phe Leu Asp Gln Asn Met
465                 470                 475                 480 ctg gcc gtg atc gac gag ctg atg cag gcc ctg aac ttc aac agc gag      1488
Leu Ala Val Ile Asp Glu Leu Met Gln Ala Leu Asn Phe Asn Ser Glu
                485                 490                 495 aca gtg ccc cag aag tct agc ctg gaa gaa ccc gac ttc tac aag acc      1536
Thr Val Pro Gln Lys Ser Ser Leu Glu Glu Pro Asp Phe Tyr Lys Thr
            500                 505                 510 aag atc aag ctg tgc atc ctg ctg cac gcc ttc cgc atc aga gcc gtg      1584
Lys Ile Lys Leu Cys Ile Leu Leu His Ala Phe Arg Ile Arg Ala Val
        515                 520                 525 acc atc gat aga gtg atg agc tac ctg aac gcc tcc tga                  1623
Thr Ile Asp Arg Val Met Ser Tyr Leu Asn Ala Ser
    530                 535                 540
```

```
<210> SEQ ID NO 5
<211> LENGTH: 540
<212> TYPE: PRT
<213> ORGANISM: Artificial Sequence
<220> FEATURE:
<223> OTHER INFORMATION: [CDS]:1..1623 from SEQ ID NO 4

<400> SEQUENCE: 5

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
        50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
                100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
        130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
                180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
        210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255
```

-continued

```
Glu Tyr Pro Asp Thr Trp Ser Thr Pro His Ser Tyr Phe Ser Leu Thr
            260             265             270

Phe Cys Val Gln Val Gln Gly Lys Ser Lys Arg Glu Lys Lys Asp Arg
        275             280             285

Val Phe Thr Asp Lys Thr Ser Ala Thr Val Ile Cys Arg Lys Asn Ala
    290             295             300

Ser Ile Ser Val Arg Ala Gln Asp Arg Tyr Tyr Ser Ser Ser Trp Ser
305             310             315             320

Glu Trp Ala Ser Val Pro Cys Ser Gly Gly Gly Gly Ser Gly Gly Gly
            325             330             335

Gly Ser Gly Gly Gly Gly Ser Arg Asn Leu Pro Val Ala Thr Pro Asp
            340             345             350

Pro Gly Met Phe Pro Cys Leu His His Ser Gln Asn Leu Leu Arg Ala
            355             360             365

Val Ser Asn Met Leu Gln Lys Ala Arg Gln Thr Leu Glu Phe Tyr Pro
    370             375             380

Cys Thr Ser Glu Glu Ile Asp His Glu Asp Ile Thr Lys Asp Lys Thr
385             390             395             400

Ser Thr Val Glu Ala Cys Leu Pro Leu Glu Leu Thr Lys Asn Glu Ser
            405             410             415

Cys Leu Asn Ser Arg Glu Thr Ser Phe Ile Thr Asn Gly Ser Cys Leu
            420             425             430

Ala Ser Arg Lys Thr Ser Phe Met Met Ala Leu Cys Leu Ser Ser Ile
            435             440             445

Tyr Glu Asp Leu Lys Met Tyr Gln Val Glu Phe Lys Thr Met Asn Ala
    450             455             460

Lys Leu Leu Met Asp Pro Lys Arg Gln Ile Phe Leu Asp Gln Asn Met
465             470             475             480

Leu Ala Val Ile Asp Glu Leu Met Gln Ala Leu Asn Phe Asn Ser Glu
            485             490             495

Thr Val Pro Gln Lys Ser Ser Leu Glu Glu Pro Asp Phe Tyr Lys Thr
            500             505             510

Lys Ile Lys Leu Cys Ile Leu Leu His Ala Phe Arg Ile Arg Ala Val
            515             520             525

Thr Ile Asp Arg Val Met Ser Tyr Leu Asn Ala Ser
    530             535             540
```

```
<210> SEQ ID NO 6
<211> LENGTH: 534
<212> TYPE: DNA
<213> ORGANISM: Artificial Sequence
<220> FEATURE:
<223> OTHER INFORMATION: synthetic coding sequence for IL-18
<220> FEATURE:
<221> NAME/KEY: CDS
<222> LOCATION: 1..534
<223> OTHER INFORMATION: /note="synthetic coding sequence for IL-18"
      /transl_table=1

<400> SEQUENCE: 6 atg gcc tgg acc gtt ctc ctc ctc ggc ctc ctc tct cac tgc aca ggc        48
Met Ala Trp Thr Val Leu Leu Leu Gly Leu Leu Ser His Cys Thr Gly
1               5                   10                  15 tct gtg acc tcc tac ttt ggc aag ctt gaa tct aaa tta tca gtc ata        96
Ser Val Thr Ser Tyr Phe Gly Lys Leu Glu Ser Lys Leu Ser Val Ile
                20                  25                  30 aga aat ttg aat gac caa gtt ctc ttc att gac caa gga aat cgg cct       144
Arg Asn Leu Asn Asp Gln Val Leu Phe Ile Asp Gln Gly Asn Arg Pro
```

-continued

```
                35                    40                    45 cta ttt gaa gat atg act gat tct gac tgt aga gat aat gca ccc cgg        192
Leu Phe Glu Asp Met Thr Asp Ser Asp Cys Arg Asp Asn Ala Pro Arg
    50                    55                    60 acc ata ttt att ata agt atg tat aaa gat agc cag cct aga ggt atg        240
Thr Ile Phe Ile Ile Ser Met Tyr Lys Asp Ser Gln Pro Arg Gly Met
65                    70                    75                    80 gct gta act atc tct gtg aag tgt gag aaa att tca act ctc tcc tgt        288
Ala Val Thr Ile Ser Val Lys Cys Glu Lys Ile Ser Thr Leu Ser Cys
                85                    90                    95 gag aac aaa att att tcc ttt aag gaa atg aat cct cct gat aac atc        336
Glu Asn Lys Ile Ile Ser Phe Lys Glu Met Asn Pro Pro Asp Asn Ile
            100                   105                   110 aag gat aca aaa agt gac atc ata ttc ttt cag aga agt gtc cca gga        384
Lys Asp Thr Lys Ser Asp Ile Ile Phe Phe Gln Arg Ser Val Pro Gly
            115                   120                   125 cat gat aat aag atg caa ttt gaa tct tca tca tac gaa gga tac ttt        432
His Asp Asn Lys Met Gln Phe Glu Ser Ser Ser Tyr Glu Gly Tyr Phe
        130                   135                   140 cta gct tgt gaa aaa gag aga gac ctt ttt aaa ctc att ttg aaa aaa        480
Leu Ala Cys Glu Lys Glu Arg Asp Leu Phe Lys Leu Ile Leu Lys Lys
145                   150                   155                   160 gag gat gaa ttg ggg gat aga tct ata atg ttc act gtt caa aac gaa        528
Glu Asp Glu Leu Gly Asp Arg Ser Ile Met Phe Thr Val Gln Asn Glu
                165                   170                   175 gac tag                                                                534
Asp

<210> SEQ ID NO 7
<211> LENGTH: 177
<212> TYPE: PRT
<213> ORGANISM: Artificial Sequence
<220> FEATURE:
<223> OTHER INFORMATION: [CDS]:1..534 from SEQ ID NO 6

<400> SEQUENCE: 7

Met Ala Trp Thr Val Leu Leu Leu Gly Leu Leu Ser His Cys Thr Gly
1               5                   10                  15

Ser Val Thr Ser Tyr Phe Gly Lys Leu Glu Ser Lys Leu Ser Val Ile
            20                  25                  30

Arg Asn Leu Asn Asp Gln Val Leu Phe Ile Asp Gln Gly Asn Arg Pro
        35                  40                  45

Leu Phe Glu Asp Met Thr Asp Ser Asp Cys Arg Asp Asn Ala Pro Arg
    50                  55                  60

Thr Ile Phe Ile Ile Ser Met Tyr Lys Asp Ser Gln Pro Arg Gly Met
65                  70                  75                  80

Ala Val Thr Ile Ser Val Lys Cys Glu Lys Ile Ser Thr Leu Ser Cys
                85                  90                  95

Glu Asn Lys Ile Ile Ser Phe Lys Glu Met Asn Pro Pro Asp Asn Ile
            100                 105                 110

Lys Asp Thr Lys Ser Asp Ile Ile Phe Phe Gln Arg Ser Val Pro Gly
        115                 120                 125

His Asp Asn Lys Met Gln Phe Glu Ser Ser Ser Tyr Glu Gly Tyr Phe
        130                 135                 140

Leu Ala Cys Glu Lys Glu Arg Asp Leu Phe Lys Leu Ile Leu Lys Lys
145                 150                 155                 160

Glu Asp Glu Leu Gly Asp Arg Ser Ile Met Phe Thr Val Gln Asn Glu
                165                 170                 175
```

Asp

```
<210> SEQ ID NO 8
<211> LENGTH: 9555
<212> TYPE: DNA
<213> ORGANISM: Artificial Sequence
<220> FEATURE:
<223> OTHER INFORMATION: pCCL.PPT.NFATenhsyn.EGFP.PGK.CAR.wPRE
<220> FEATURE:
<221> NAME/KEY: promoter
<222> LOCATION: 1785..2455
<223> OTHER INFORMATION: /function="CMV promoter"
<220> FEATURE:
<221> NAME/KEY: LTR
<222> LOCATION: 2456..2636
<223> OTHER INFORMATION: /note="5B4 LTR truncated"
<220> FEATURE:
<221> NAME/KEY: misc_signal
<222> LOCATION: 2683..2808
<223> OTHER INFORMATION: /note="packaging signal of HIV-1"
<220> FEATURE:
<221> NAME/KEY: misc_signal
<222> LOCATION: 3301..3534
<223> OTHER INFORMATION: /note="RRE of HIV-1"
<220> FEATURE:
<221> NAME/KEY: misc_signal
<222> LOCATION: 3302..3543
<223> OTHER INFORMATION: /note="PRE"
<220> FEATURE:
<221> NAME/KEY: terminator
<222> LOCATION: 4027..4150
<223> OTHER INFORMATION: /note="cPPT/CTScPPT/CTS, central polypurine
      tract and central termination sequence of HIV-1"
<220> FEATURE:
<221> NAME/KEY: promoter
<222> LOCATION: 4174..4417
<223> OTHER INFORMATION: /note="NFATenhsyn"
<220> FEATURE:
<221> NAME/KEY: CDS
<222> LOCATION: 4430..5149
<223> OTHER INFORMATION: /gene="EGFP"
      /transl_table=1
<220> FEATURE:
<221> NAME/KEY: promoter
<222> LOCATION: 5158..5673
<223> OTHER INFORMATION: /note="PGK promoter"
<220> FEATURE:
<221> NAME/KEY: gene
<222> LOCATION: 5705..7159
<223> OTHER INFORMATION: /gene="placeholder for CAR"
      /n=any nucleotide
<220> FEATURE:
<221> NAME/KEY: misc_signal
<222> LOCATION: 7186..7774
<223> OTHER INFORMATION: /note="WPRE"
<220> FEATURE:
<221> NAME/KEY: LTR
<222> LOCATION: 7861..8094
<223> OTHER INFORMATION: /note="3B4 LTR (delta U3)"

<400> SEQUENCE: 8
agtactcacc agtcacagaa aagcatctta cggatggcat gacagtaaga gaattatgca    60
gtgctgccat aaccatgagt gataacactg cggccaactt acttctgaca acgatcggag   120
gaccgaagga gctaaccgct tttttgcaca acatgggga  tcatgtaact cgccttgatc   180
gttgggaacc ggagctgaat gaagccatac caaacgacga gcgtgacacc acgatgcctg   240
tagcaatggc aacaacgttg cgcaaactat taactggcga actacttact ctagcttccc   300
ggcaacaatt aatagactgg atggaggcgg ataaagttgc aggaccactt ctgcgctcgg   360
cccttccggc tggctggttt attgctgata aatctggagc cggtgagcgt gggtctcgcg   420
gtatcattgc agcactgggg ccagatggta agccctcccg tatcgtagtt atctacacga   480
```

-continued

```
cggggagtca ggcaactatg gatgaacgaa atagacagat cgctgagata ggtgcctcac    540
tgattaagca ttggtaactg tcagaccaag tttactcata tatactttag attgatttaa    600
aacttcattt ttaatttaaa aggatctagg tgaagatcct ttttgataat ctcatgacca    660
aaatccctta acgtgagttt tcgttccact gagcgtcaga ccccgtagaa aagatcaaag    720
gatcttcttg agatcctttt tttctgcgcg taatctgctg cttgcaaaca aaaaaaccac    780
cgctaccagc ggtggtttgt ttgccggatc aagagctacc aactcttttt ccgaaggtaa    840
ctggcttcag cagagcgcag ataccaaata ctgttcttct agtgtagccg tagttaggcc    900
accacttcaa gaactctgta gcaccgccta catacctcgc tctgctaatc ctgttaccag    960
tggctgctgc cagtggcgat aagtcgtgtc ttaccgggtt ggactcaaga cgatagttac   1020
cggataaggc gcagcggtcg ggctgaacgg ggggttcgtg cacacagccc agcttggagc   1080
gaacgaccta caccgaactg agatacctac agcgtgagct atgagaaagc gccacgcttc   1140
ccgaagggag aaaggcggac aggtatccgg taagcggcag ggtcggaaca ggagagcgca   1200
cgagggagct tccaggggga aacgcctggt atctttatag tcctgtcggg tttcgccacc   1260
tctgacttga gcgtcgattt ttgtgatgct cgtcagggggg gcggagccta tggaaaaacg   1320
ccagcaacgc ggcctttttta cggttcctgg cctttttgctg gcctttttgct cacatgttct   1380 ttcctgcgtt atccctgat tctgtggata accgtattac cgcctttgag tgagctgata   1440
ccgctcgccg cagccgaacg accgagcgca gcgagtcagt gagcgaggaa gcggaagagc   1500
gcccaatacg caaaccgcct ctccccgcgc gttggccgat tcattaatgc agctggcacg   1560
acaggtttcc cgactggaaa gcgggcagtg agcgcaacgc aattaatgtg agttagctca   1620
ctcattaggc accccaggct ttacacttta tgcttccggc tcgtatgttg tgtggaattg   1680
tgagcggata acaatttcac acaggaaaca gctatgacca tgattacgcc aagcgcgcaa   1740
ttaaccctca ctaaagggaa caaaagctgg agctgcaagc ttggccattg catacgttgt   1800
atccatatca taatatgtac atttatattg gctcatgtcc aacattaccg ccatgttgac   1860
attgattatt gactagttat taatagtaat caattacggg gtcattagtt catagcccat   1920
atatggagtt ccgcgttaca taacttacgg taaatggccc gcctggctga ccgcccaacg   1980
acccccgccc attgacgtca ataatgacgt atgttcccat agtaacgcca tagggactt   2040 tccattgacg tcaatgggtg gagtatttac ggtaaactgc ccacttggca gtacatcaag   2100
tgtatcatat gccaagtacg cccctattg acgtcaatga cggtaaatgg cccgcctggc   2160
attatgccca gtacatgacc ttatgggact ttcctacttg gcagtacatc tacgtattag   2220
tcatcgctat taccatggtg atgcggtttt ggcagtacat caatgggcgt ggatagcggt   2280
ttgactcacg gggatttcca agtctccacc ccattgacgt caatgggagt ttgttttggc   2340
accaaaatca acgggacttt ccaaaatgtc gtaacaactc cgccccattg acgcaaatgg   2400
gcggtaggcg tgtacggtgg gaggtctata taagcagagc tcgtttagtg aaccggggtc   2460
tctctggtta gaccagatct gagcctggga gctctctggc taactaggga acccactgct   2520
taagcctcaa taaagcttgc cttgagtgct tcaagtagtg tgtgcccgtc tgttgtgtga   2580
ctctggtaac tagagatccc tcagaccctt ttagtcagtg tggaaaatct ctagcagtgg   2640
cgcccgaaca gggacttgaa agcgaaaggg aaaccagagg agctctctcg acgcaggact   2700
cggcttgctg aagcgcgcac ggcaagaggc gaggggcggc gactggtgag tacgccaaaa   2760
attttgacta gcggaggcta gaaggagaga gatgggtgcg agagcgtcag tattaagcgg   2820
```

-continued

```
gggagaatta gatcgcgatg ggaaaaaatt cggttaaggc caggggggaaa gaaaaaatat      2880 aaattaaaac atatagtatg ggcaagcagg gagctagaac gattcgcagt taatcctggc      2940
ctgttagaaa catcagaagg ctgtagacaa atactgggac agctacaacc atcccttcag      3000
acaggatcag aagaacttag atcattatat aatacagtag caaccctcta ttgtgtgcat      3060
caaaggatag agataaaaga caccaaggaa gctttagaca agatagagga agagcaaaac      3120
aaaagtaaga ccaccgcaca gcaagcggcc gctgatcttc agacctggag gaggagatat      3180
gagggacaat tggagaagtg aattatataa atataaagta gtaaaaattg aaccattagg      3240
agtagcaccc accaaggcaa agagaagagt ggtgcagaga gaaaaaagag cagtgggaat      3300
aggagctttg ttccttgggt tcttgggagc agcaggaagc actatgggcg cagcctcaat      3360
gacgctgacg gtacaggcca gacaattatt gtctggtata gtgcagcagc agaacaattt      3420
gctgagggct attgaggcgc aacagcatct gttgcaactc acagtctggg gcatcaagca      3480
gctccaggca agaatcctgg ctgtggaaag atacctaaag gatcaacagc tcctggggat      3540
ttggggttgc tctggaaaac tcatttgcac cactgctgtg ccttggaatg ctagttggag      3600
taataaatct ctggaacaga tttggaatca cacgacctgg atggagtggg acagagaaat      3660
taacaattac acaagcttaa tacactcctt aattgaagaa tcgcaaaacc agcaagaaaa      3720
gaatgaacaa gaattattgg aattagataa atgggcaagt ttgtggaatt ggtttaacat      3780
aacaaattgg ctgtggtata taaaattatt cataatgata gtaggaggct tggtaggttt      3840
aagaatagtt tttgctgtac tttctatagt gaatagagtt aggcagggat attcaccatt      3900
atcgtttcag acccacctcc caaccccgag gggacccgac aggcccgaag gaatagaaga      3960
agaaggtgga gagagagaca gagacagatc cattcgatta gtgaacggat ctcgacggta      4020
tcggttaact tttaaaagaa aagggggggat tggggggtac agtgcagggg aaagaatagt      4080
agacataata gcaacagaca tacaaactaa agaattacaa aaacaaatta caaaaattca      4140
aaattttatc gatcacgaga ctagcctcga gcgtggagga aaaactgttt catacagaag      4200
gcgtggagga aaaactgttt catacagaag gcgtggagga aaaactgttt catacagaag      4260
gcgtggagga aaaactgttt catacagaag gcgtggagga aaaactgttt catacagaag      4320
gcgtggagga aaaactgttt catacagaag gcgtctgcag gagactctag agggtatata      4380
atggtttaaa cttaagcttg gtaccgggcc cccgaagacg cgtgccacc atg gtg agc      4438
                                                       Met Val Ser
                                                         1
```

```
aag ggc gag gag ctg ttc acc ggg gtg gtg ccc atc ctg gtc gag ctg      4486
Lys Gly Glu Glu Leu Phe Thr Gly Val Val Pro Ile Leu Val Glu Leu
  5                  10                  15
```

```
gac ggc gac gta aac ggc cac aag ttc agc gtg tcc ggc gag ggc gag      4534
Asp Gly Asp Val Asn Gly His Lys Phe Ser Val Ser Gly Glu Gly Glu
 20                  25                  30                  35
```

```
ggc gat gcc acc tac ggc aag ctg acc ctg aag ttc atc tgc acc acc      4582
Gly Asp Ala Thr Tyr Gly Lys Leu Thr Leu Lys Phe Ile Cys Thr Thr
             40                  45                  50
```

```
ggc aag ctg ccc gtg ccc tgg ccc acc ctc gtg acc acc ctg acc tac      4630
Gly Lys Leu Pro Val Pro Trp Pro Thr Leu Val Thr Thr Leu Thr Tyr
         55                  60                  65
```

```
ggc gtg cag tgc ttc agc cgc tac ccc gac cac atg aag cag cac gac      4678
Gly Val Gln Cys Phe Ser Arg Tyr Pro Asp His Met Lys Gln His Asp
     70                  75                  80
```

```
ttc ttc aag tcc gcc atg ccc gaa ggc tac gtc cag gag cgc acc atc      4726
Phe Phe Lys Ser Ala Met Pro Glu Gly Tyr Val Gln Glu Arg Thr Ile
 85                  90                  95
```

-continued

```
ttc ttc aag gac gac ggc aac tac aag acc cgc gcc gag gtg aag ttc     4774
Phe Phe Lys Asp Asp Gly Asn Tyr Lys Thr Arg Ala Glu Val Lys Phe
100                 105                 110                 115 gag ggc gac acc ctg gtg aac cgc atc gag ctg aag ggc atc gac ttc     4822
Glu Gly Asp Thr Leu Val Asn Arg Ile Glu Leu Lys Gly Ile Asp Phe
                120                 125                 130 aag gag gac ggc aac atc ctg ggg cac aag ctg gag tac aac tac aac     4870
Lys Glu Asp Gly Asn Ile Leu Gly His Lys Leu Glu Tyr Asn Tyr Asn
                135                 140                 145 agc cac aac gtc tat atc atg gcc gac aag cag aag aac ggc atc aag     4918
Ser His Asn Val Tyr Ile Met Ala Asp Lys Gln Lys Asn Gly Ile Lys
            150                 155                 160 gtg aac ttc aag atc cgc cac aac atc gag gac ggc agc gtg cag ctc     4966
Val Asn Phe Lys Ile Arg His Asn Ile Glu Asp Gly Ser Val Gln Leu
        165                 170                 175 gcc gac cac tac cag cag aac acc ccc atc ggc gac ggc ccc gtg ctg     5014
Ala Asp His Tyr Gln Gln Asn Thr Pro Ile Gly Asp Gly Pro Val Leu
180                 185                 190                 195 ctg ccc gac aac cac tac ctg agc acc cag tcc gcc ctg agc aaa gac     5062
Leu Pro Asp Asn His Tyr Leu Ser Thr Gln Ser Ala Leu Ser Lys Asp
                200                 205                 210 ccc aac gag aag cgc gat cac atg gtc ctg ctg gag ttc gtg acc gcc     5110
Pro Asn Glu Lys Arg Asp His Met Val Leu Leu Glu Phe Val Thr Ala
            215                 220                 225 gcc ggg atc act ctc ggc atg gac gag ctg tac aag taa tcgaattccc     5159
Ala Gly Ile Thr Leu Gly Met Asp Glu Leu Tyr Lys
            230                 235 acggggttgg ggttgcgcct tttccaaggc agccctgggt ttgcgcaggg acgcggctgc     5219
tctgggcgtg gttccgggaa acgcagcggc gccgaccctg ggtctcgcac attcttcacg     5279
tccgttcgca gcgtcacccg gatcttcgcc gctacccttg tgggcccccc ggcgacgctt     5339
cctgctccgc ccctaagtcg ggaaggttcc ttgcggttcg cggcgtgccg gacgtgacaa     5399
acggaagccg cacgtctcac tagtaccctc gcagacggac agcgccaggg agcaatggca     5459
gcgcgccgac cgcgatgggc tgtggccaat agcggctgct cagcggggcg cgccgagagc     5519
agcggccggg aaggggcggt gcgggaggcg gggtgtgggg cggtagtgtg ggccctgttc     5579
ctgcccgcgc ggtgttccgc attctgcaag cctccggagc gcacgtcggc agtcggctcc     5639
ctcgttgacc gaatcaccga cctctctccc caggggggatc caccggtcac gtggctagcg     5699
ccaccnnnnn nnnnnnnnnn nnnnnnnnnn nnnnnnnnnn nnnnnnnnnn nnnnnnnnnn     5759
nnnnnnnnnn nnnnnnnnnn nnnnnnnnnn nnnnnnnnnn nnnnnnnnnn nnnnnnnnnn     5819
nnnnnnnnnn nnnnnnnnnn nnnnnnnnnn nnnnnnnnnn nnnnnnnnnn nnnnnnnnnn     5879
nnnnnnnnnn nnnnnnnnnn nnnnnnnnnn nnnnnnnnnn nnnnnnnnnn nnnnnnnnnn     5939
nnnnnnnnnn nnnnnnnnnn nnnnnnnnnn nnnnnnnnnn nnnnnnnnnn nnnnnnnnnn     5999
nnnnnnnnnn nnnnnnnnnn nnnnnnnnnn nnnnnnnnnn nnnnnnnnnn nnnnnnnnnn     6059
nnnnnnnnnn nnnnnnnnnn nnnnnnnnnn nnnnnnnnnn nnnnnnnnnn nnnnnnnnnn     6119
nnnnnnnnnn nnnnnnnnnn nnnnnnnnnn nnnnnnnnnn nnnnnnnnnn nnnnnnnnnn     6179
nnnnnnnnnn nnnnnnnnnn nnnnnnnnnn nnnnnnnnnn nnnnnnnnnn nnnnnnnnnn     6239
nnnnnnnnnn nnnnnnnnnn nnnnnnnnnn nnnnnnnnnn nnnnnnnnnn nnnnnnnnnn     6299
nnnnnnnnnn nnnnnnnnnn nnnnnnnnnn nnnnnnnnnn nnnnnnnnnn nnnnnnnnnn     6359
nnnnnnnnnn nnnnnnnnnn nnnnnnnnnn nnnnnnnnnn nnnnnnnnnn nnnnnnnnnn     6419
```

-continued

```
nnnnnnnnnn nnnnnnnnnn nnnnnnnnnn nnnnnnnnnn nnnnnnnnnn nnnnnnnnnn      6479
nnnnnnnnnn nnnnnnnnnn nnnnnnnnnn nnnnnnnnnn nnnnnnnnnn nnnnnnnnnn      6539
nnnnnnnnnn nnnnnnnnnn nnnnnnnnnn nnnnnnnnnn nnnnnnnnnn nnnnnnnnnn      6599
nnnnnnnnnn nnnnnnnnnn nnnnnnnnnn nnnnnnnnnn nnnnnnnnnn nnnnnnnnnn      6659
nnnnnnnnnn nnnnnnnnnn nnnnnnnnnn nnnnnnnnnn nnnnnnnnnn nnnnnnnnnn      6719
nnnnnnnnnn nnnnnnnnnn nnnnnnnnnn nnnnnnnnnn nnnnnnnnnn nnnnnnnnnn      6779
nnnnnnnnnn nnnnnnnnnn nnnnnnnnnn nnnnnnnnnn nnnnnnnnnn nnnnnnnnnn      6839
nnnnnnnnnn nnnnnnnnnn nnnnnnnnnn nnnnnnnnnn nnnnnnnnnn nnnnnnnnnn      6899
nnnnnnnnnn nnnnnnnnnn nnnnnnnnnn nnnnnnnnnn nnnnnnnnnn nnnnnnnnnn      6959
nnnnnnnnnn nnnnnnnnnn nnnnnnnnnn nnnnnnnnnn nnnnnnnnnn nnnnnnnnnn      7019
nnnnnnnnnn nnnnnnnnnn nnnnnnnnnn nnnnnnnnnn nnnnnnnnnn nnnnnnnnnn      7079
nnnnnnnnnn nnnnnnnnnn nnnnnnnnnn nnnnnnnnnn nnnnnnnnnn nnnnnnnnnn      7139
nnnnnnnnnn nnnnnnnnnn taggatccgc cggcggccgc gtcgacaatc aacctctgga      7199
ttacaaaatt tgtgaaagat tgactggtat tcttaactat gttgctcctt ttacgctatg      7259
tggatacgct gctttaatgc ctttgtatca tgctattgct tcccgtatgg ctttcatttt      7319
ctcctccttg tataaatcct ggttgctgtc tctttatgag gagttgtggc ccgttgtcag      7379
gcaacgtggc gtggtgtgca ctgtgtttgc tgacgcaacc cccactggtt ggggcattgc      7439
caccacctgt cagctccttt ccgggacttt cgctttcccc ctccctattg ccacggcgga      7499
actcatcgcc gcctgccttg cccgctgctg gacagggggct cggctgttgg gcactgacaa      7559
ttccgtggtg ttgtcgggga agctgacgtc ctttccatgg ctgctcgcct gtgttgccac      7619
ctggattctg cgcgggacgt ccttctgcta cgtcccttcg gccctcaatc cagcggacct      7679
tccttcccgc ggcctgctgc cggctctgcg gcctcttccg cgtcttcgcc ttcgccctca      7739
gacgagtcgg atctcccttt gggccgcctc cccgcctgga attcgagctc ggtacctta      7799 agaccaatga cttacaaggc agctgtagat cttagccact ttttaaaaga aaaggggggga      7859 ctggaagggc taattcactc ccaacgaaga caagatctgc ttttttgcttg tactgggtct      7919 ctctggttag accagatctg agcctgggag ctctctggct aactagggaa cccactgctt      7979
aagcctcaat aaagcttgcc ttgagtgctt caagtagtgt gtgcccgtct gttgtgtgac      8039
tctggtaact agagatccct cagacccttt tagtcagtgt ggaaaatctc tagcagtagt      8099
agttcatgtc atcttattat tcagtattta aacttgcaa agaaatgaat atcagagagt      8159
gagaggaact tgtttattgc agcttataat ggttacaaat aaagcaatag catcacaaat      8219
ttcacaaata aagcatttt ttcactgcat tctagttgtg gtttgtccaa actcatcaat      8279
gtatcttatc atgtctggct ctagctatcc cgcccctaac tccgcccagt tccgcccatt      8339
ctccgcccca tggctgacta attttttttta tttatgcaga ggccgaggcc gcctcggcct      8399
ctgagctatt ccagaagtag tgaggaggct ttttttggagg cctaggcttt tgcgtcgaga      8459
cgtacccaat tcgccctata gtgagtcgta ttacgcgcgc tcactggccg tcgttttaca      8519
acgtcgtgac tgggaaaacc ctggcgttac ccaacttaat cgccttgcag cacatccccc      8579
tttcgccagc tggcgtaata gcgaagaggc ccgcaccgat cgcccttccc aacagttgcg      8639
cagcctgaat ggcgaatggc gcgacgcgcc ctgtagcggc gcattaagcg cggcgggtgt      8699
ggtggttacg cgcagcgtga ccgctacact tgccagcgcc ctagcgcccg ctcctttcgc      8759
tttcttccct tcctttctcg ccacgttcgc cggctttccc cgtcaagctc taaatcgggg      8819
```

```
gctcccttta gggttccgat ttagtgcttt acggcacctc gaccccaaaa aacttgatta      8879
gggtgatggt tcacgtagtg ggccatcgcc ctgatagacg gtttttcgcc ctttgacgtt      8939
ggagtccacg ttctttaata gtggactctt gttccaaact ggaacaacac tcaaccctat      8999
ctcggtctat tctttttgatt tataagggat tttgccgatt tcggcctatt ggttaaaaaa      9059
tgagctgatt taacaaaaat ttaacgcgaa tttttaacaaa atattaacgt ttacaatttc      9119
ccaggtggca cttttcgggg aaatgtgcgc ggaacccta tttgtttatt tttctaaata      9179
cattcaaata tgtatccgct catgagacaa taaccctgat aaatgcttca ataatattga      9239
aaaaggaaga gtatgagtat tcaacatttc cgtgtcgccc ttattccctt ttttgcggca      9299
ttttgccttc ctgtttttgc tcacccagaa acgctggtga aagtaaaaga tgctgaagat      9359
cagttgggtg cacgagtggg ttacatcgaa ctggatctca acagcggtaa gatccttgag      9419
agttttcgcc ccgaagaacg ttttccaatg atgagcactt ttaaagttct gctatgtggc      9479
gcggtattat cccgtattga cgccgggcaa gagcaactcg tcgccgcat acactattct      9539 cagaatgact tggttg                                                      9555
```

<210> SEQ ID NO 9
<211> LENGTH: 239
<212> TYPE: PRT
<213> ORGANISM: Artificial Sequence
<220> FEATURE:
<223> OTHER INFORMATION: [CDS]:4430..5149 from SEQ ID NO 8

<400> SEQUENCE: 9

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
        210                 215                 220
```

```
Val Thr Ala Ala Gly Ile Thr Leu Gly Met Asp Glu Leu Tyr Lys
225                 230                 235
```

```
<210> SEQ ID NO 10
<211> LENGTH: 407
<212> TYPE: DNA
<213> ORGANISM: Artificial Sequence
<220> FEATURE:
<223> OTHER INFORMATION: SFFV promoter

<400> SEQUENCE: 10
gtaacgccat tttgcaaggc atggaaaaat accaaaccaa gaatagagaa gttcagatca        60
agggcgggta catgaaaata gctaacgttg ggccaaacag gatatctgcg gtgagcagtt       120
tcggccccgg cccggggcca agaacagatg gtcaccgcag tttcggcccc ggcccgaggc       180
caagaacaga tggtccccag atatggccca accctcagca gtttcttaag acccatcaga       240
tgtttccagg ctcccccaag gacctgaaat gaccctgcgc cttatttgaa ttaaccaatc       300
agcctgcttc tcgcttctgt tcgcgcgctt ctgcttcccg agctctataa aagagctcac       360
aacccctcac tcggcgcgcc agtcctccga cagactgagt cggccgg                     407

<210> SEQ ID NO 11
<211> LENGTH: 245
<212> TYPE: DNA
<213> ORGANISM: Artificial Sequence
<220> FEATURE:
<223> OTHER INFORMATION: EF-1 alpha promoter

<400> SEQUENCE: 11
tggctccggt gcccgtcagt gggcagagcg cacatcgccc acagtccccg agaagttggg        60
gggaggggtc ggcaattgaa ccggtgccta gagaaggtgg cgcggggtaa actgggaaag       120
tgatgtcgtg tactggctcc gcctttttcc cgagggtggg ggagaaccgt atataagtgc       180
agtagtcgcc gtgaacgttc tttttcgcaa cgggtttgcc gccagaacac aggtgtcgtg       240
acgcg                                                                   245

<210> SEQ ID NO 12
<211> LENGTH: 671
<212> TYPE: DNA
<213> ORGANISM: Artificial Sequence
<220> FEATURE:
<223> OTHER INFORMATION: CMV promoter element

<400> SEQUENCE: 12
ccattgcata cgttgtatcc atatcataat atgtacattt atattggctc atgtccaaca        60
ttaccgccat gttgacattg attattgact agttattaat agtaatcaat tacggggtca       120
ttagttcata gcccatatat ggagttccgc gttacataac ttacggtaaa tggcccgcct       180
ggctgaccgc ccaacgaccc ccgcccattg acgtcaataa tgacgtatgt tcccatagta       240
acgccaatag ggactttcca ttgacgtcaa tgggtggagt atttacggta aactgcccac       300
ttggcagtac atcaagtgta tcatatgcca agtacgcccc ctattgacgt caatgacggt       360
aaatggcccg cctggcatta tgcccagtac atgaccttat gggactttcc tacttggcag       420
tacatctacg tattagtcat cgctattacc atggtgatgc ggttttggca gtacatcaat       480
gggcgtggat agcggtttga ctcacgggga tttccaagtc tccaccccat tgacgtcaat       540
gggagtttgt tttggcacca aaatcaacgg gactttccaa aatgtcgtaa caactccgcc       600
ccattgacgc aaatgggcgg taggcgtgta cggtgggagg tctatataag cagagctcgt       660
```

-continued

```
ttagtgaacc g                                                          671

<210> SEQ ID NO 13
<211> LENGTH: 232
<212> TYPE: DNA
<213> ORGANISM: Artificial Sequence
<220> FEATURE:
<223> OTHER INFORMATION: RSV promoter element

<400> SEQUENCE: 13
ttaatgtagt cttatgcaat actcttgtag tcttgcaaca tggtaacgat gagttagcaa      60
catgccttac aaggagagaa aaagcaccgt gcatgccgat tggtggaagt aaggtggtac     120
gatcgtgcct tattaggaag gcaacagacg ggtctgacat ggattggacg aaccactgaa     180
ttgccgcatt gcagagatat tgtatttaag tgcctagctc gatacaataa ac              232

<210> SEQ ID NO 14
<211> LENGTH: 454
<212> TYPE: DNA
<213> ORGANISM: Artificial Sequence
<220> FEATURE:
<223> OTHER INFORMATION: HIV U3 promoter element

<400> SEQUENCE: 14
ttggaagggc taattcactc ccaaagaaga caagatatcc ttgatctgtg gatctaccac      60
acacaaggct acttccctga ttagcagaac tacacaccag ggccaggggt cagatatcca     120
ctgacctttg gatggtgcta caagctagta ccagttgagc cagataaggt agaagaggcc     180
aataaaggag agaacaccag cttgttacac cctgtgagcc tgcatgggat ggatgacccg     240
gagagagaag tgttagagtg gaggtttgac agccgcctag catttcatca cgtggcccga     300
gagctgcatc cggagtactt caagaactgc tgatatcgag cttgctacaa gggactttcc     360
gctggggact ttccagggag gcgtggcctg ggcgggactg gggagtggcg agccctcaga     420
tcctgcatat aagcagctgc tttttgcctg tact                                  454

<210> SEQ ID NO 15
<211> LENGTH: 589
<212> TYPE: DNA
<213> ORGANISM: Artificial Sequence
<220> FEATURE:
<223> OTHER INFORMATION: WPRE element

<400> SEQUENCE: 15
aatcaacctc tggattacaa aatttgtgaa agattgactg gtattcttaa ctatgttgct      60 cctttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccact      240 ggttggggca ttgccaccac ctgtcagctc ctttccggga ctttcgcttt ccccctccct     300
attgccacgg cggaactcat cgccgcctgc cttgcccgct gctggacagg gctcggctg      360 ttgggcactg acaattccgt ggtgttgtcg gggaagctga cgtcctttcc atggctgctc     420
gcctgtgttg ccacctggat tctgcgcggg acgtccttct gctacgtccc ttcggccctc     480
aatccagcgg accttccttc ccgcggcctg ctgccggctc tgcggcctct tccgcgtctt     540
cgccttcgcc ctcagacgag tcggatctcc ctttgggccg cctccccgc                  589

<210> SEQ ID NO 16
<211> LENGTH: 10469
```

```
<212> TYPE: DNA
<213> ORGANISM: Artificial Sequence
<220> FEATURE:
<223> OTHER INFORMATION: pCCL.PPT.NFATenhsyn.humanIL12.PGK.CAR.wPRE
<220> FEATURE:
<221> NAME/KEY: promoter
<222> LOCATION: 1785..2455
<223> OTHER INFORMATION: /note="CMV promoter"
<220> FEATURE:
<221> NAME/KEY: LTR
<222> LOCATION: 2456..2636
<223> OTHER INFORMATION: /note="5B4 LTR truncated"
<220> FEATURE:
<221> NAME/KEY: misc_signal
<222> LOCATION: 2683..2808
<223> OTHER INFORMATION: /note="packaging signal of HIV-1"
<220> FEATURE:
<221> NAME/KEY: misc_signal
<222> LOCATION: 3301..3534
<223> OTHER INFORMATION: /note="RRE: rev response element of HIV-1"
<220> FEATURE:
<221> NAME/KEY: misc_signal
<222> LOCATION: 3302..3543
<223> OTHER INFORMATION: /note="PRE of HIV-1"
<220> FEATURE:
<221> NAME/KEY: terminator
<222> LOCATION: 4027..4150
<223> OTHER INFORMATION: /note="cPPT/CTScPPT/CTS: central polypurine
      tract and central termination sequence of HIV-1"
<220> FEATURE:
<221> NAME/KEY: promoter
<222> LOCATION: 4174..4417
<223> OTHER INFORMATION: /note="NFATenhsyn"
<220> FEATURE:
<221> NAME/KEY: CDS
<222> LOCATION: 4430..6052
<223> OTHER INFORMATION: /gene="sc IL2 humanized codon usage"
      /transl_table=1
<220> FEATURE:
<221> NAME/KEY: promoter
<222> LOCATION: 6072..6587
<223> OTHER INFORMATION: /note="PGK promoter"
<220> FEATURE:
<221> NAME/KEY: gene
<222> LOCATION: 6619..8073
<223> OTHER INFORMATION: /gene="placeholder for CAR"
      /n=any nucleotide
<220> FEATURE:
<221> NAME/KEY: LTR
<222> LOCATION: 7861..8094
<223> OTHER INFORMATION: /note="3B4 LTR (delta U3)"
<220> FEATURE:
<221> NAME/KEY: misc_signal
<222> LOCATION: 8100..8688
<223> OTHER INFORMATION: /note="WPRE"

<400> SEQUENCE: 16
agtactcacc agtcacagaa aagcatctta cggatggcat gacagtaaga gaattatgca        60
gtgctgccat aaccatgagt gataacactg cggccaactt acttctgaca acgatcggag       120
gaccgaagga gctaaccgct tttttgcaca acatggggga tcatgtaact cgccttgatc       180
gttgggaacc ggagctgaat gaagccatac caaacgacga gcgtgacacc acgatgcctg       240
tagcaatggc aacaacgttg cgcaaactat taactggcga actacttact ctagcttccc       300
ggcaacaatt aatagactgg atggaggcgg ataaagttgc aggaccactt ctgcgctcgg       360
cccttccggc tggctggttt attgctgata atctggagc cggtgagcgt gggtctcgcg       420
gtatcattgc agcactgggg ccagatggta agccctcccg tatcgtagtt atctacacga       480
cggggagtca ggcaactatg gatgaacgaa atagacagat cgctgagata ggtgcctcac       540
tgattaagca ttggtaactg tcagaccaag tttactcata tatactttag attgatttaa       600
aacttcattt ttaatttaaa aggatctagg tgaagatcct ttttgataat ctcatgacca       660
```

-continued

```
aaatccctta acgtgagttt tcgttccact gagcgtcaga ccccgtagaa aagatcaaag    720
gatcttcttg agatcctttt tttctgcgcg taatctgctg cttgcaaaca aaaaaaccac    780
cgctaccagc ggtggtttgt ttgccggatc aagagctacc aactcttttt ccgaaggtaa    840
ctggcttcag cagagcgcag ataccaaata ctgttcttct agtgtagccg tagttaggcc    900
accacttcaa gaactctgta gcaccgccta catacctcgc tctgctaatc ctgttaccag    960
tggctgctgc cagtggcgat aagtcgtgtc ttaccgggtt ggactcaaga cgatagttac   1020
cggataaggc gcagcggtcg ggctgaacgg ggggttcgtg cacacagccc agcttggagc   1080
gaacgaccta caccgaactg agatacctac agcgtgagct atgagaaagc gccacgcttc   1140
ccgaagggag aaaggcggac aggtatccgg taagcggcag ggtcggaaca ggagagcgca   1200
cgagggagct tccaggggga aacgcctggt atctttatag tcctgtcggg tttcgccacc   1260
tctgacttga gcgtcgattt ttgtgatgct cgtcagggg gcggagccta tggaaaaacg   1320
ccagcaacgc ggccttttta cggttcctgg ccttttgctg gccttttgct cacatgttct   1380
ttcctgcgtt atcccctgat tctgtggata accgtattac cgcctttgag tgagctgata   1440
ccgctcgccg cagccgaacg accgagcgca gcgagtcagt gagcgaggaa gcggaagagc   1500
gcccaatacg caaaccgcct ctccccgcgc gttggccgat tcattaatgc agctggcacg   1560
acaggtttcc cgactggaaa gcgggcagtg agcgcaacgc aattaatgtg agttagctca   1620
ctcattaggc accccaggct ttacacttta tgcttccggc tcgtatgttg tgtggaattg   1680
tgagcggata acaatttcac acaggaaaca gctatgacca tgattacgcc aagcgcgcaa   1740
ttaaccctca ctaaagggaa caaaagctgg agctgcaagc ttggccattg catacgttgt   1800
atccatatca taatatgtac atttatattg gctcatgtcc aacattaccg ccatgttgac   1860
attgattatt gactagttat taatagtaat caattacggg gtcattagtt catagcccat   1920
atatggagtt ccgcgttaca taacttacgg taaatggccc gcctggctga ccgcccaacg   1980
acccccgccc attgacgtca ataatgacgt atgttcccat agtaacgcca atagggactt   2040
tccattgacg tcaatgggtg gagtatttac ggtaaactgc ccacttggca gtacatcaag   2100
tgtatcatat gccaagtacg cccctattg acgtcaatga cggtaaatgg cccgcctggc   2160
attatgccca gtacatgacc ttatgggact ttcctacttg gcagtacatc tacgtattag   2220
tcatcgctat taccatggtg atgcggtttt ggcagtacat caatgggcgt ggatagcggt   2280
ttgactcacg gggatttcca agtctccacc ccattgacgt caatgggagt ttgttttggc   2340
accaaaatca acgggacttt ccaaaatgtc gtaacaactc cgccccattg acgcaaatgg   2400
gcggtaggcg tgtacggtgg gaggtctata taagcagagc tcgtttagtg aaccggggtc   2460
tctctggtta gaccagatct gagcctggga gctctctggc taactaggga acccactgct   2520
taagcctcaa taaagcttgc cttgagtgct tcaagtagtg tgtgcccgtc tgttgtgtga   2580
ctctggtaac tagagatccc tcagaccctt ttagtcagtg tggaaaatct ctagcagtgg   2640
cgcccgaaca gggacttgaa agcgaaaggg aaaccagagg agctctctcg acgcaggact   2700
cggcttgctg aagcgcgcac ggcaagaggc gaggggcggc gactggtgag tacgccaaaa   2760
attttgacta gcggaggcta gaaggagaga gatgggtgcg agagcgtcag tattaagcgg   2820
gggagaatta gatcgcgatg ggaaaaaatt cggttaaggc cagggggaaa gaaaaaatat   2880
aaattaaaac atatagtatg ggcaagcagg gagctagaac gattcgcagt taatcctggc   2940
ctgttagaaa catcagaagg ctgtagacaa atactgggac agctacaacc atcccttcag   3000
```

```
acaggatcag aagaacttag atcattatat aatacagtag caaccctcta ttgtgtgcat        3060
caaaggatag agataaaaga caccaaggaa gctttagaca agatagagga agagcaaaac        3120
aaaagtaaga ccaccgcaca gcaagcggcc gctgatcttc agacctggag gaggagatat        3180
gagggacaat tggagaagtg aattatataa atataaagta gtaaaaattg aaccattagg        3240
agtagcaccc accaaggcaa agagaagagt ggtgcagaga gaaaaaagag cagtgggaat        3300
aggagctttg ttccttgggt tcttgggagc agcaggaagc actatgggcg cagcctcaat        3360
gacgctgacg gtacaggcca gacaattatt gtctggtata gtgcagcagc agaacaattt        3420
gctgagggct attgaggcgc aacagcatct gttgcaactc acagtctggg gcatcaagca        3480
gctccaggca agaatcctgg ctgtggaaag atacctaaag gatcaacagc tcctggggat        3540
ttggggttgc tctggaaaac tcatttgcac cactgctgtg ccttggaatg ctagttggag        3600
taataaatct ctggaacaga tttggaatca cacgacctgg atggagtggg acagagaaat        3660
taacaattac acaagcttaa tacactcctt aattgaagaa tcgcaaaacc agcaagaaaa        3720
gaatgaacaa gaattattgg aattagataa atgggcaagt ttgtggaatt ggtttaacat        3780
aacaaattgg ctgtggtata taaaattatt cataatgata gtaggaggct tggtaggttt        3840
aagaatagtt tttgctgtac tttctatagt gaatagagtt aggcagggat attcaccatt        3900
atcgtttcag acccacctcc caaccccgag gggacccgac aggcccgaag gaatagaaga        3960
agaaggtgga gagagagaca gagacagatc cattcgatta gtgaacggat ctcgacggta        4020
tcggttaact tttaaagaa aagggggggat tggggggtac agtgcagggg aaagaatagt        4080
agacataata gcaacagaca tacaaactaa agaattacaa aaacaaatta caaaaattca        4140
aaattttatc gatcacgaga ctagcctcga gcgtggagga aaaactgttt catacagaag        4200
gcgtggagga aaaactgttt catacagaag gcgtggagga aaaactgttt catacagaag        4260
gcgtggagga aaaactgttt catacagaag gcgtggagga aaaactgttt catacagaag        4320
gcgtggagga aaaactgttt catacagaag gcgtctgcag gagactctag agggtatata        4380
```

```
atggtttaaa cttaagcttg gtaccgggcc cccgaagacg cgtgccacc atg tgt cac        4438
                                                         Met Cys His
                                                          1
```

```
cag cag ctg gtc atc agc tgg ttc agc ctg gtg ttc ctg gcc tct cct        4486
Gln Gln Leu Val Ile Ser Trp Phe Ser Leu Val Phe Leu Ala Ser Pro
  5               10                  15
```

```
ctg gtg gcc atc tgg gag ctg aag aaa gac gtg tac gtg gtg gaa ctg        4534
Leu Val Ala Ile Trp Glu Leu Lys Lys Asp Val Tyr Val Val Glu Leu
20               25                  30                  35
```

```
gac tgg tat ccc gat gct cct ggc gag atg gtg gtg ctg acc tgc gat        4582
Asp Trp Tyr Pro Asp Ala Pro Gly Glu Met Val Val Leu Thr Cys Asp
             40                  45                  50
```

```
acc cct gaa gag gac ggc atc acc tgg aca ctg gat cag tct agc gag        4630
Thr Pro Glu Glu Asp Gly Ile Thr Trp Thr Leu Asp Gln Ser Ser Glu
         55                  60                  65
```

```
gtg ctc ggc agc ggc aag acc ctg acc atc caa gtg aaa gag ttt ggc        4678
Val Leu Gly Ser Gly Lys Thr Leu Thr Ile Gln Val Lys Glu Phe Gly
         70                  75                  80
```

```
gac gcc ggc cag tac acc tgt cac aaa ggc gga gaa gtg ctg agc cac        4726
Asp Ala Gly Gln Tyr Thr Cys His Lys Gly Gly Glu Val Leu Ser His
         85                  90                  95
```

```
agc ctg ctg ctg ctc cac aag aaa gag gat ggc att tgg agc acc gac        4774
Ser Leu Leu Leu Leu His Lys Lys Glu Asp Gly Ile Trp Ser Thr Asp
100                 105                 110                 115
```

```
atc ctg aag gac cag aaa gag ccc aag aac aag acc ttc ctg aga tgc        4822
```

-continued

```
Ile Leu Lys Asp Gln Lys Glu Pro Lys Asn Lys Thr Phe Leu Arg Cys
            120                 125                 130 gag gcc aag aac tac agc ggc cgg ttc aca tgt tgg tgg ctg acc acc    4870
Glu Ala Lys Asn Tyr Ser Gly Arg Phe Thr Cys Trp Trp Leu Thr Thr
            135                 140                 145 atc agc acc gac ctg acc ttc agc gtg aag tcc agc aga ggc agc agt    4918
Ile Ser Thr Asp Leu Thr Phe Ser Val Lys Ser Ser Arg Gly Ser Ser
            150                 155                 160 gat cct cag ggc gtt aca tgt ggc gcc gct aca ctg tct gcc gaa aga    4966
Asp Pro Gln Gly Val Thr Cys Gly Ala Ala Thr Leu Ser Ala Glu Arg
        165                 170                 175 gtg cgg ggc gac aac aaa gaa tac gag tac agc gtg gaa tgc caa gag    5014
Val Arg Gly Asp Asn Lys Glu Tyr Glu Tyr Ser Val Glu Cys Gln Glu
180                 185                 190                 195 gac agc gcc tgt cca gcc gcc gaa gag tct ctg cct atc gaa gtg atg    5062
Asp Ser Ala Cys Pro Ala Ala Glu Glu Ser Leu Pro Ile Glu Val Met
                200                 205                 210 gtg gac gcc gtg cac aag ctg aag tac gag aac tac acc tcc agc ttt    5110
Val Asp Ala Val His Lys Leu Lys Tyr Glu Asn Tyr Thr Ser Ser Phe
            215                 220                 225 ttc atc cgg gac atc atc aag ccc gat cct cca aag aac ctg cag ctg    5158
Phe Ile Arg Asp Ile Ile Lys Pro Asp Pro Pro Lys Asn Leu Gln Leu
            230                 235                 240 aag cct ctg aag aac agc aga cag gtg gaa gtg tcc tgg gag tac ccc    5206
Lys Pro Leu Lys Asn Ser Arg Gln Val Glu Val Ser Trp Glu Tyr Pro
        245                 250                 255 gac acc tgg tct aca ccc cac agc tac ttc agc ctg acc ttt tgc gtg    5254
Asp Thr Trp Ser Thr Pro His Ser Tyr Phe Ser Leu Thr Phe Cys Val
260                 265                 270                 275 caa gtg cag ggc aag tcc aag cgc gag aaa aag gac cgg gtg ttc acc    5302
Gln Val Gln Gly Lys Ser Lys Arg Glu Lys Lys Asp Arg Val Phe Thr
                280                 285                 290 gac aag acc agc gcc acc gtg atc tgc aga aag aac gcc agc atc agc    5350
Asp Lys Thr Ser Ala Thr Val Ile Cys Arg Lys Asn Ala Ser Ile Ser
            295                 300                 305 gtc aga gcc cag gac cgc tac tac agc agc tct tgg agc gaa tgg gcc    5398
Val Arg Ala Gln Asp Arg Tyr Tyr Ser Ser Ser Trp Ser Glu Trp Ala
        310                 315                 320 agc gtg cca tgt tct ggt ggc gga gga tct ggc gga ggt gga agc ggc    5446
Ser Val Pro Cys Ser Gly Gly Gly Gly Ser Gly Gly Gly Gly Ser Gly
        325                 330                 335 gga ggc gga tct aga aat ctg cct gtg gcc act cct gat cct ggc atg    5494
Gly Gly Gly Ser Arg Asn Leu Pro Val Ala Thr Pro Asp Pro Gly Met
340                 345                 350                 355 ttc cct tgt ctg cac cac agc cag aac ctg ctg aga gcc gtg tcc aac    5542
Phe Pro Cys Leu His His Ser Gln Asn Leu Leu Arg Ala Val Ser Asn
            360                 365                 370 atg ctg cag aag gcc aga cag acc ctg gaa ttc tac ccc tgc acc agc    5590
Met Leu Gln Lys Ala Arg Gln Thr Leu Glu Phe Tyr Pro Cys Thr Ser
            375                 380                 385 gag gaa atc gac cac gag gac atc acc aag gat aag acc agt acc gtg    5638
Glu Glu Ile Asp His Glu Asp Ile Thr Lys Asp Lys Thr Ser Thr Val
            390                 395                 400 gaa gcc tgc ctg cct ctg gaa ctg acc aag aac gag agc tgc ctg aac    5686
Glu Ala Cys Leu Pro Leu Glu Leu Thr Lys Asn Glu Ser Cys Leu Asn
        405                 410                 415 agc cgg gaa acc agc ttc atc acc aac ggc tct tgc ctg gcc agc aga    5734
Ser Arg Glu Thr Ser Phe Ile Thr Asn Gly Ser Cys Leu Ala Ser Arg
420                 425                 430                 435
```

-continued

```
aag acc tcc ttc atg atg gcc ctg tgc ctg agc agc atc tac gag gac    5782
Lys Thr Ser Phe Met Met Ala Leu Cys Leu Ser Ser Ile Tyr Glu Asp
                440                 445                 450 ctg aag atg tac cag gtg gaa ttc aag acc atg aac gcc aag ctg ctg    5830
Leu Lys Met Tyr Gln Val Glu Phe Lys Thr Met Asn Ala Lys Leu Leu
                455                 460                 465 atg gac ccc aag cgg cag atc ttc ctg gac cag aat atg ctg gcc gtg    5878
Met Asp Pro Lys Arg Gln Ile Phe Leu Asp Gln Asn Met Leu Ala Val
                470                 475                 480 atc gac gag ctg atg cag gcc ctg aac ttc aac agc gag aca gtg ccc    5926
Ile Asp Glu Leu Met Gln Ala Leu Asn Phe Asn Ser Glu Thr Val Pro
                485                 490                 495 cag aag tct agc ctg gaa gaa ccc gac ttc tac aag acc aag atc aag    5974
Gln Lys Ser Ser Leu Glu Glu Pro Asp Phe Tyr Lys Thr Lys Ile Lys
500                 505                 510                 515 ctg tgc atc ctg ctg cac gcc ttc cgc atc aga gcc gtg acc atc gat    6022
Leu Cys Ile Leu Leu His Ala Phe Arg Ile Arg Ala Val Thr Ile Asp
                520                 525                 530 aga gtg atg agc tac ctg aac gcc tcc tga tgtacaagta atcgaattcc      6072
Arg Val Met Ser Tyr Leu Asn Ala Ser
                535                 540 cacggggttg gggttgcgcc tttttccaagg cagccctggg tttgcgcagg gacgcggctg   6132
ctctgggcgt ggttccggga aacgcagcgg cgccgaccct gggtctcgca cattcttcac   6192
gtccgttcgc agcgtcaccc ggatcttcgc cgctacccct gtgggccccc cggcgacgct   6252
tcctgctccg cccctaagtc gggaaggttc cttgcggttc gcggcgtgcc ggacgtgaca   6312
aacggaagcc gcacgtctca ctagtaccct cgcagacgga cagcgccagg gagcaatggc   6372
agcgcgccga ccgcgatggg ctgtggccaa tagcggctgc tcagcggggc gcgccgagag   6432
cagcggccgg gaaggggcgg tgcgggaggc ggggtgtggg gcggtagtgt gggccctgtt   6492
cctgcccgcg cggtgttccg cattctgcaa gcctccggag cgcacgtcgg cagtcggctc   6552
cctcgttgac cgaatcaccg acctctctcc caggggggat ccaccggtca cgtggctagc   6612
gccaccnnnn nnnnnnnnnn nnnnnnnnnn nnnnnnnnnn nnnnnnnnnn nnnnnnnnnn   6672
nnnnnnnnnn nnnnnnnnnn nnnnnnnnnn nnnnnnnnnn nnnnnnnnnn nnnnnnnnnn   6732
nnnnnnnnnn nnnnnnnnnn nnnnnnnnnn nnnnnnnnnn nnnnnnnnnn nnnnnnnnnn   6792
nnnnnnnnnn nnnnnnnnnn nnnnnnnnnn nnnnnnnnnn nnnnnnnnnn nnnnnnnnnn   6852
nnnnnnnnnn nnnnnnnnnn nnnnnnnnnn nnnnnnnnnn nnnnnnnnnn nnnnnnnnnn   6912
nnnnnnnnnn nnnnnnnnnn nnnnnnnnnn nnnnnnnnnn nnnnnnnnnn nnnnnnnnnn   6972
nnnnnnnnnn nnnnnnnnnn nnnnnnnnnn nnnnnnnnnn nnnnnnnnnn nnnnnnnnnn   7032
nnnnnnnnnn nnnnnnnnnn nnnnnnnnnn nnnnnnnnnn nnnnnnnnnn nnnnnnnnnn   7092
nnnnnnnnnn nnnnnnnnnn nnnnnnnnnn nnnnnnnnnn nnnnnnnnnn nnnnnnnnnn   7152
nnnnnnnnnn nnnnnnnnnn nnnnnnnnnn nnnnnnnnnn nnnnnnnnnn nnnnnnnnnn   7212
nnnnnnnnnn nnnnnnnnnn nnnnnnnnnn nnnnnnnnnn nnnnnnnnnn nnnnnnnnnn   7272
nnnnnnnnnn nnnnnnnnnn nnnnnnnnnn nnnnnnnnnn nnnnnnnnnn nnnnnnnnnn   7332
nnnnnnnnnn nnnnnnnnnn nnnnnnnnnn nnnnnnnnnn nnnnnnnnnn nnnnnnnnnn   7392
nnnnnnnnnn nnnnnnnnnn nnnnnnnnnn nnnnnnnnnn nnnnnnnnnn nnnnnnnnnn   7452
nnnnnnnnnn nnnnnnnnnn nnnnnnnnnn nnnnnnnnnn nnnnnnnnnn nnnnnnnnnn   7512
nnnnnnnnnn nnnnnnnnnn nnnnnnnnnn nnnnnnnnnn nnnnnnnnnn nnnnnnnnnn   7572
nnnnnnnnnn nnnnnnnnnn nnnnnnnnnn nnnnnnnnnn nnnnnnnnnn nnnnnnnnnn   7632
```

-continued

```
nnnnnnnnnn nnnnnnnnnn nnnnnnnnnn nnnnnnnnnn nnnnnnnnnn nnnnnnnnnn      7692
nnnnnnnnnn nnnnnnnnnn nnnnnnnnnn nnnnnnnnnn nnnnnnnnnn nnnnnnnnnn      7752
nnnnnnnnnn nnnnnnnnnn nnnnnnnnnn nnnnnnnnnn nnnnnnnnnn nnnnnnnnnn      7812
nnnnnnnnnn nnnnnnnnnn nnnnnnnnnn nnnnnnnnnn nnnnnnnnnn nnnnnnnnnn      7872
nnnnnnnnnn nnnnnnnnnn nnnnnnnnnn nnnnnnnnnn nnnnnnnnnn nnnnnnnnnn      7932
nnnnnnnnnn nnnnnnnnnn nnnnnnnnnn nnnnnnnnnn nnnnnnnnnn nnnnnnnnnn      7992
nnnnnnnnnn nnnnnnnnnn nnnnnnnnnn nnnnnnnnnn nnnnnnnnnn nnnnnnnnnn      8052
nnnnnnnnnn nnnnnnnnnn ntaggatccg ccggcggccg cgtcgacaat caacctctgg      8112
attacaaaat ttgtgaaaga ttgactggta ttcttaacta tgttgctcct tttacgctat      8172
gtggatacgc tgctttaatg cctttgtatc atgctattgc ttcccgtatg gctttcattt      8232
tctcctcctt gtataaatcc tggttgctgt ctctttatga ggagttgtgg cccgttgtca      8292
ggcaacgtgg cgtggtgtgc actgtgtttg ctgacgcaac ccccactggt tggggcattg      8352
ccaccacctg tcagctcctt tccgggactt tcgctttccc cctccctatt gccacggcgg      8412
aactcatcgc cgcctgcctt gcccgctgct ggacaggggc tcggctgttg ggcactgaca      8472
attccgtggt gttgtcgggg aagctgacgt cctttccatg gctgctcgcc tgtgttgcca      8532
cctggattct gcgcgggacg tccttctgct acgtcccttc ggccctcaat ccagcggacc      8592
ttccttcccg cggcctgctg ccggctctgc ggcctcttcc gcgtcttcgc cttcgccctc      8652
agacgagtcg gatctccctt tgggccgcct ccccgcctgg aattcgagct cggtaccttt      8712
aagaccaatg acttacaagg cagctgtaga tcttagccac tttttaaaag aaaaggggg      8772 actggaaggg ctaattcact cccaacgaag acaagatctg cttttttgctt gtactgggtc      8832 tctctggtta gaccagatct gagcctggga gctctctggc taactaggga acccactgct      8892
taagcctcaa taaagcttgc cttgagtgct tcaagtagtg tgtgcccgtc tgttgtgtga      8952
ctctggtaac tagagatccc tcagaccctt ttagtcagtg tggaaaatct ctagcagtag      9012
tagttcatgt catcttatta ttcagtattt ataacttgca aagaaatgaa tatcagagag      9072
tgagaggaac ttgtttattg cagcttataa tggttacaaa taaagcaata gcatcacaaa      9132
tttcacaaat aaagcatttt tttcactgca ttctagttgt ggtttgtcca aactcatcaa      9192
tgtatcttat catgtctggc tctagctatc ccgcccctaa ctccgcccag ttccgcccat      9252
tctccgcccc atggctgact aattttttttt atttatgcag aggccgaggc cgcctcggcc      9312
tctgagctat tccagaagta gtgaggaggc tttttttggag gcctaggctt ttgcgtcgag      9372
acgtacccaa ttcgccctat agtgagtcgt attacgcgcg ctcactggcc gtcgttttac      9432
aacgtcgtga ctgggaaaac cctggcgtta cccaacttaa tcgccttgca gcacatcccc      9492
ctttcgccag ctggcgtaat agcgaagagg cccgcaccga tcgcccttcc caacagttgc      9552
gcagcctgaa tggcgaatgg cgcgacgcgc cctgtagcgg cgcattaagc gcggcgggtg      9612
tggtggttac gcgcagcgtg accgctacac ttgccagcgc cctagcgccc gctcctttcg      9672
ctttcttccc ttcctttctc gccacgttcg ccggctttcc ccgtcaagct ctaaatcggg      9732
ggctcccttt agggttccga tttagtgctt tacggcacct cgacccccaa aaaacttgatt      9792 agggtgatgg ttcacgtagt gggccatcgc cctgatagac ggtttttcgc cctttgacgt      9852
tggagtccac gttctttaat agtggactct tgttccaaac tggaacaaca ctcaacccta      9912
tctcggtcta ttcttttgat ttataaggga ttttgccgat ttcggcctat tggttaaaaa      9972
```

-continued

```
atgagctgat ttaacaaaaa tttaacgcga attttaacaa aatattaacg tttacaattt    10032
cccaggtggc actttcgggg gaaatgtgcg cggaacccct atttgtttat ttttctaaat    10092
acattcaaat atgtatccgc tcatgagaca ataaccctga taaatgcttc aataatattg    10152
aaaaaggaag agtatgagta ttcaacattt ccgtgtcgcc cttattccct tttttgcggc    10212
attttgcctt cctgtttttg ctcacccaga aacgctggtg aaagtaaaag atgctgaaga    10272
tcagttgggt gcacgagtgg gttacatcga actggatctc aacagcggta agatccttga    10332 gagtttttcgc cccgaagaac gttttccaat gatgagcact tttaaagttc tgctatgtgg    10392
cgcggtatta tcccgtattg acgccgggca agagcaactc ggtcgccgca tacactattc    10452
tcagaatgac ttggttg                                                    10469
```

<210> SEQ ID NO 17
<211> LENGTH: 540
<212> TYPE: PRT
<213> ORGANISM: Artificial Sequence
<220> FEATURE:
<223> OTHER INFORMATION: [CDS]:4430..6052 from SEQ ID NO 16

<400> SEQUENCE: 17

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270
```

-continued

```
Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Ser Gly Gly Gly
                325                 330                 335

Gly Ser Gly Gly Gly Gly Ser Arg Asn Leu Pro Val Ala Thr Pro Asp
                340                 345                 350

Pro Gly Met Phe Pro Cys Leu His His Ser Gln Asn Leu Leu Arg Ala
        355                 360                 365

Val Ser Asn Met Leu Gln Lys Ala Arg Gln Thr Leu Glu Phe Tyr Pro
    370                 375                 380

Cys Thr Ser Glu Glu Ile Asp His Glu Asp Ile Thr Lys Asp Lys Thr
385                 390                 395                 400

Ser Thr Val Glu Ala Cys Leu Pro Leu Glu Leu Thr Lys Asn Glu Ser
                405                 410                 415

Cys Leu Asn Ser Arg Glu Thr Ser Phe Ile Thr Asn Gly Ser Cys Leu
                420                 425                 430

Ala Ser Arg Lys Thr Ser Phe Met Met Ala Leu Cys Leu Ser Ser Ile
        435                 440                 445

Tyr Glu Asp Leu Lys Met Tyr Gln Val Glu Phe Lys Thr Met Asn Ala
    450                 455                 460

Lys Leu Leu Met Asp Pro Lys Arg Gln Ile Phe Leu Asp Gln Asn Met
465                 470                 475                 480

Leu Ala Val Ile Asp Glu Leu Met Gln Ala Leu Asn Phe Asn Ser Glu
                485                 490                 495

Thr Val Pro Gln Lys Ser Ser Leu Glu Glu Pro Asp Phe Tyr Lys Thr
                500                 505                 510

Lys Ile Lys Leu Cys Ile Leu Leu His Ala Phe Arg Ile Arg Ala Val
        515                 520                 525

Thr Ile Asp Arg Val Met Ser Tyr Leu Asn Ala Ser
    530                 535                 540
```

```
<210> SEQ ID NO 18
<211> LENGTH: 9380
<212> TYPE: DNA
<213> ORGANISM: Artificial Sequence
<220> FEATURE:
<223> OTHER INFORMATION: pCCL.PPT.NFATenhsyn.humanIL18.PGK.CAR.wPRE
<220> FEATURE:
<221> NAME/KEY: promoter
<222> LOCATION: 1785..2455
<223> OTHER INFORMATION: /note="CMV promoter"
<220> FEATURE:
<221> NAME/KEY: LTR
<222> LOCATION: 2456..2636
<223> OTHER INFORMATION: /note="5B4 LTR truncated"
<220> FEATURE:
<221> NAME/KEY: misc_signal
<222> LOCATION: 2683..2808
<223> OTHER INFORMATION: /note="packaging signal of HIV-1"
<220> FEATURE:
<221> NAME/KEY: misc_signal
<222> LOCATION: 3301..3534
<223> OTHER INFORMATION: /note="RRE: rev response element of HIV-1"
<220> FEATURE:
<221> NAME/KEY: terminator
<222> LOCATION: 4030..4147
<223> OTHER INFORMATION: /note="cPPT/CTS, central polypurine tract and
      central termination sequence of HIV-1"
```

```
<220> FEATURE:
<221> NAME/KEY: promoter
<222> LOCATION: 4174..4417
<223> OTHER INFORMATION: /note="NFATenhsyn"
<220> FEATURE:
<221> NAME/KEY: CDS
<222> LOCATION: 4430..4963
<223> OTHER INFORMATION: /gene="signal peptide and human IL18"
        /transl_table=1
<220> FEATURE:
<221> NAME/KEY: gene
<222> LOCATION: 5530..6984
<223> OTHER INFORMATION: /note="placeholder for CAR"
        /n=any nucleotide
<220> FEATURE:
<221> NAME/KEY: misc_signal
<222> LOCATION: 7011..7599
<223> OTHER INFORMATION: /note="WPRE"

<400> SEQUENCE: 18
agtactcacc agtcacagaa aagcatctta cggatggcat gacagtaaga gaattatgca        60
gtgctgccat aaccatgagt gataacactg cggccaactt acttctgaca acgatcggag       120
gaccgaagga gctaaccgct tttttgcaca acatgggga tcatgtaact cgccttgatc       180
gttgggaacc ggagctgaat gaagccatac caaacgacga gcgtgacacc acgatgcctg       240
tagcaatggc aacaacgttg cgcaaactat taactggcga actacttact ctagcttccc       300
ggcaacaatt aatagactgg atggaggcgg ataaagttgc aggaccactt ctgcgctcgg       360
cccttccggc tggctggttt attgctgata atctggagc cggtgagcgt gggtctcgcg       420
gtatcattgc agcactgggg ccagatggta agccctcccg tatcgtagtt atctacacga       480
cggggagtca ggcaactatg gatgaacgaa atagacagat cgctgagata ggtgcctcac       540
tgattaagca ttggtaactg tcagaccaag tttactcata tatactttag attgatttaa       600
aacttcattt ttaatttaaa aggatctagg tgaagatcct ttttgataat ctcatgacca       660 aaatcccctta acgtgagttt tcgttccact gagcgtcaga ccccgtagaa aagatcaaag       720
gatcttcttg agatcctttt tttctgcgcg taatctgctg cttgcaaaca aaaaaaccac       780
cgctaccagc ggtggtttgt ttgccggatc aagagctacc aactcttttt ccgaaggtaa       840
ctggcttcag cagagcgcag ataccaaata ctgttcttct agtgtagccg tagttaggcc       900
accacttcaa gaactctgta gcaccgccta catacctcgc tctgctaatc ctgttaccag       960
tggctgctgc cagtggcgat aagtcgtgtc ttaccgggtt ggactcaaga cgatagttac      1020
cggataaggc gcagcggtcg ggctgaacgg ggggttcgtg cacacagccc agcttggagc      1080
gaacgaccta caccgaactg agatacctac agcgtgagct atgagaaagc gccacgcttc      1140
ccgaagggag aaaggcggac aggtatccgg taagcggcag ggtcggaaca ggagagcgca      1200
cgagggagct tccaggggga aacgcctggt atctttatag tcctgtcggg tttcgccacc      1260
tctgacttga gcgtcgattt ttgtgatgct cgtcagggg gcggagccta tggaaaaacg      1320
ccagcaacgc ggcctttta cggttcctgg ccttttgctg gccttttgct cacatgttct      1380
ttcctgcgtt atcccctgat tctgtggata accgtattac cgcctttgag tgagctgata      1440
ccgctcgccg cagccgaacg accgagcgca gcgagtcagt gagcgaggaa gcggaagagc      1500
gcccaatacg caaaccgcct ctccccgcgc gttggccgat tcattaatgc agctggcacg      1560
acaggtttcc cgactggaaa gcgggcagtg agcgcaacgc aattaatgtg agttagctca      1620
ctcattaggc accccaggct ttacacttta tgcttccggc tcgtatgttg tgtggaattg      1680
tgagcggata acaatttcac acaggaaaca gctatgacca tgattacgcc aagcgcgcaa      1740
```

-continued

```
ttaaccctca ctaaagggaa caaaagctgg agctgcaagc ttggccattg catacgttgt    1800
atccatatca taatatgtac atttatattg gctcatgtcc aacattaccg ccatgttgac    1860
attgattatt gactagttat taatagtaat caattacggg gtcattagtt catagcccat    1920
atatggagtt ccgcgttaca taacttacgg taaatggccc gcctggctga ccgcccaacg    1980 accccgccc attgacgtca ataatgacgt atgttcccat agtaacgcca atagggactt     2040
tccattgacg tcaatgggtg gagtatttac ggtaaactgc ccacttggca gtacatcaag    2100
tgtatcatat gccaagtacg cccctattg acgtcaatga cggtaaatgg cccgcctggc     2160
attatgccca gtacatgacc ttatgggact ttcctacttg gcagtacatc tacgtattag    2220
tcatcgctat taccatggtg atgcggtttt ggcagtacat caatgggcgt ggatagcggt    2280
ttgactcacg gggatttcca agtctccacc ccattgacgt caatgggagt ttgttttggc    2340
accaaaatca acgggacttt ccaaaatgtc gtaacaactc cgccccattg acgcaaatgg    2400
gcggtaggcg tgtacggtgg gaggtctata taagcagagc tcgtttagtg aaccggggtc    2460
tctctggtta gaccagatct gagcctggga gctctctggc taactaggga acccactgct    2520
taagcctcaa taaagcttgc cttgagtgct tcaagtagtg tgtgcccgtc tgttgtgtga    2580
ctctggtaac tagagatccc tcagaccctt ttagtcagtg tggaaaatct ctagcagtgg    2640
cgcccgaaca gggacttgaa agcgaaaggg aaaccagagg agctctctcg acgcaggact    2700
cggcttgctg aagcgcgcac ggcaagaggc gaggggcggc gactggtgag tacgccaaaa    2760
attttgacta gcggaggcta gaaggagaga gatgggtgcg agagcgtcag tattaagcgg    2820
gggagaatta gatcgcgatg gaaaaaaatt cggttaaggc caggggggaaa gaaaaaatat    2880 aaattaaaac atatagtatg ggcaagcagg gagctagaac gattcgcagt taatcctggc    2940
ctgttagaaa catcagaagg ctgtagacaa atactgggac agctacaacc atcccttcag    3000
acaggatcag aagaacttag atcattatat aatacagtag caaccctcta ttgtgtgcat    3060
caaaggatag agataaaaga caccaaggaa gctttagaca agatagagga agagcaaaac    3120
aaaagtaaga ccaccgcaca gcaagcggcc gctgatcttc agacctggag gaggagatat    3180
gagggacaat tggagaagtg aattatataa atataaagta gtaaaaattg aaccattagg    3240
agtagcaccc accaaggcaa agagaagagt ggtgcagaga gaaaaaagag cagtgggaat    3300
aggagctttg ttccttgggt tcttgggagc agcaggaagc actatgggcg cagcctcaat    3360
gacgctgacg gtacaggcca gacaattatt gtctggtata gtgcagcagc agaacaattt    3420
gctgagggct attgaggcgc aacagcatct gttgcaactc acagtctggg gcatcaagca    3480
gctccaggca agaatcctgg ctgtggaaag atacctaaag gatcaacagc tcctggggat    3540
ttggggttgc tctggaaaac tcatttgcac cactgctgtg ccttggaatg ctagttggag    3600
taataaatct ctggaacaga tttggaatca cacgacctgg atggagtggg acagagaaat    3660
taacaattac acaagcttaa tacactcctt aattgaagaa tcgcaaaacc agcaagaaaa    3720
gaatgaacaa gaattattgg aattagataa atgggcaagt ttgtggaatt ggtttaacat    3780
aacaaattgg ctgtggtata taaaattatt cataatgata gtaggaggct tggtaggttt    3840
aagaatagtt tttgctgtac tttctatagt gaatagagtt aggcagggat attcaccatt    3900
atcgtttcag acccacctcc caaccccgag gggacccgac aggcccgaag gaatagaaga    3960
agaaggtgga gagagagaca gagacagatc cattcgatta gtgaacggat ctcgacggta    4020
tcggttaact tttaaaagaa aagggggggat tggggggtac agtgcagggg aaagaatagt    4080
agacataata gcaacagaca tacaaactaa agaattacaa aaacaaatta caaaaattca    4140
```

-continued

```
aaattttatc gatcacgaga ctagcctcga gcgtggagga aaaactgttt catacagaag      4200
gcgtggagga aaaactgttt catacagaag gcgtggagga aaaactgttt catacagaag      4260
gcgtggagga aaaactgttt catacagaag gcgtggagga aaaactgttt catacagaag      4320
gcgtggagga aaaactgttt catacagaag gcgtctgcag gagactctag agggtatata      4380
atggtttaaa cttaagcttg gtaccgggcc cccgaagacg cgtgccacc atg gcc tgg      4438
                                                         Met Ala Trp
                                                          1 acc gtt ctc ctc ctc ggc ctc ctc tct cac tgc aca ggc tct gtg acc      4486
Thr Val Leu Leu Leu Gly Leu Leu Ser His Cys Thr Gly Ser Val Thr
      5                  10                  15 tcc tac ttt ggc aag ctt gaa tct aaa tta tca gtc ata aga aat ttg      4534
Ser Tyr Phe Gly Lys Leu Glu Ser Lys Leu Ser Val Ile Arg Asn Leu
20                  25                  30                  35 aat gac caa gtt ctc ttc att gac caa gga aat cgg cct cta ttt gaa      4582
Asn Asp Gln Val Leu Phe Ile Asp Gln Gly Asn Arg Pro Leu Phe Glu
                40                  45                  50 gat atg act gat tct gac tgt aga gat aat gca ccc cgg acc ata ttt      4630
Asp Met Thr Asp Ser Asp Cys Arg Asp Asn Ala Pro Arg Thr Ile Phe
                55                  60                  65 att ata agt atg tat aaa gat agc cag cct aga ggt atg gct gta act      4678
Ile Ile Ser Met Tyr Lys Asp Ser Gln Pro Arg Gly Met Ala Val Thr
            70                  75                  80 atc tct gtg aag tgt gag aaa att tca act ctc tcc tgt gag aac aaa      4726
Ile Ser Val Lys Cys Glu Lys Ile Ser Thr Leu Ser Cys Glu Asn Lys
        85                  90                  95 att att tcc ttt aag gaa atg aat cct cct gat aac atc aag gat aca      4774
Ile Ile Ser Phe Lys Glu Met Asn Pro Pro Asp Asn Ile Lys Asp Thr
100                 105                 110                 115 aaa agt gac atc ata ttc ttt cag aga agt gtc cca gga cat gat aat      4822
Lys Ser Asp Ile Ile Phe Phe Gln Arg Ser Val Pro Gly His Asp Asn
                120                 125                 130 aag atg caa ttt gaa tct tca tca tac gaa gga tac ttt cta gct tgt      4870
Lys Met Gln Phe Glu Ser Ser Ser Tyr Glu Gly Tyr Phe Leu Ala Cys
                135                 140                 145 gaa aaa gag aga gac ctt ttt aaa ctc att ttg aaa aaa gag gat gaa      4918
Glu Lys Glu Arg Asp Leu Phe Lys Leu Ile Leu Lys Lys Glu Asp Glu
            150                 155                 160 ttg ggg gat aga tct ata atg ttc act gtt caa aac gaa gac tag          4963
Leu Gly Asp Arg Ser Ile Met Phe Thr Val Gln Asn Glu Asp
        165                 170                 175 tgtacaagta atcgaattcc cacggggttg gggttgcgcc ttttccaagg cagccctggg      5023
tttgcgcagg gacgcggctg ctctgggcgt ggttccggga aacgcagcgg cgccgaccct      5083
gggtctcgca cattcttcac gtccgttcgc agcgtcaccc ggatcttcgc cgctacccttt     5143 gtgggccccc cggcgacgct tcctgctccg cccctaagtc gggaaggttc cttgcggttc      5203
gcggcgtgcc ggacgtgaca aacggaagcc gcacgtctca ctagtaccct cgcagacgga      5263
cagcgccagg gagcaatggc agcgcgccga ccgcgatggg ctgtggccaa tagcggctgc      5323
tcagcggggc gcgccgagag cagcggccgg gaaggggcgg tgcgggaggc ggggtgtggg      5383
gcggtagtgt gggccctgtt cctgcccgcg cggtgttccg cattctgcaa gcctccggag      5443
cgcacgtcgg cagtcggctc cctcgttgac cgaatcaccg acctctctcc caggggggat      5503
ccaccggtca cgtggctagc gccaccnnnn nnnnnnnnnn nnnnnnnnnn nnnnnnnnnn      5563
nnnnnnnnnn nnnnnnnnnn nnnnnnnnnn nnnnnnnnnn nnnnnnnnnn nnnnnnnnnn      5623
```

-continued

```
nnnnnnnnnn nnnnnnnnnn nnnnnnnnnn nnnnnnnnnn nnnnnnnnnn nnnnnnnnnn      5683
nnnnnnnnnn nnnnnnnnnn nnnnnnnnnn nnnnnnnnnn nnnnnnnnnn nnnnnnnnnn      5743
nnnnnnnnnn nnnnnnnnnn nnnnnnnnnn nnnnnnnnnn nnnnnnnnnn nnnnnnnnnn      5803
nnnnnnnnnn nnnnnnnnnn nnnnnnnnnn nnnnnnnnnn nnnnnnnnnn nnnnnnnnnn      5863
nnnnnnnnnn nnnnnnnnnn nnnnnnnnnn nnnnnnnnnn nnnnnnnnnn nnnnnnnnnn      5923
nnnnnnnnnn nnnnnnnnnn nnnnnnnnnn nnnnnnnnnn nnnnnnnnnn nnnnnnnnnn      5983
nnnnnnnnnn nnnnnnnnnn nnnnnnnnnn nnnnnnnnnn nnnnnnnnnn nnnnnnnnnn      6043
nnnnnnnnnn nnnnnnnnnn nnnnnnnnnn nnnnnnnnnn nnnnnnnnnn nnnnnnnnnn      6103
nnnnnnnnnn nnnnnnnnnn nnnnnnnnnn nnnnnnnnnn nnnnnnnnnn nnnnnnnnnn      6163
nnnnnnnnnn nnnnnnnnnn nnnnnnnnnn nnnnnnnnnn nnnnnnnnnn nnnnnnnnnn      6223
nnnnnnnnnn nnnnnnnnnn nnnnnnnnnn nnnnnnnnnn nnnnnnnnnn nnnnnnnnnn      6283
nnnnnnnnnn nnnnnnnnnn nnnnnnnnnn nnnnnnnnnn nnnnnnnnnn nnnnnnnnnn      6343
nnnnnnnnnn nnnnnnnnnn nnnnnnnnnn nnnnnnnnnn nnnnnnnnnn nnnnnnnnnn      6403
nnnnnnnnnn nnnnnnnnnn nnnnnnnnnn nnnnnnnnnn nnnnnnnnnn nnnnnnnnnn      6463
nnnnnnnnnn nnnnnnnnnn nnnnnnnnnn nnnnnnnnnn nnnnnnnnnn nnnnnnnnnn      6523
nnnnnnnnnn nnnnnnnnnn nnnnnnnnnn nnnnnnnnnn nnnnnnnnnn nnnnnnnnnn      6583
nnnnnnnnnn nnnnnnnnnn nnnnnnnnnn nnnnnnnnnn nnnnnnnnnn nnnnnnnnnn      6643
nnnnnnnnnn nnnnnnnnnn nnnnnnnnnn nnnnnnnnnn nnnnnnnnnn nnnnnnnnnn      6703
nnnnnnnnnn nnnnnnnnnn nnnnnnnnnn nnnnnnnnnn nnnnnnnnnn nnnnnnnnnn      6763
nnnnnnnnnn nnnnnnnnnn nnnnnnnnnn nnnnnnnnnn nnnnnnnnnn nnnnnnnnnn      6823
nnnnnnnnnn nnnnnnnnnn nnnnnnnnnn nnnnnnnnnn nnnnnnnnnn nnnnnnnnnn      6883
nnnnnnnnnn nnnnnnnnnn nnnnnnnnnn nnnnnnnnnn nnnnnnnnnn nnnnnnnnnn      6943
nnnnnnnnnn nnnnnnnnnn nnnnnnnnnn nnnnnnnnnn ntaggatccg ccggcggccg      7003
cgtcgacaat caacctctgg attacaaaat ttgtgaaaga ttgactggta ttcttaacta      7063
tgttgctcct tttacgctat gtggatacgc tgctttaatg cctttgtatc atgctattgc      7123
ttcccgtatg gctttcattt tctcctcctt gtataaatcc tggttgctgt ctctttatga      7183
ggagttgtgg cccgttgtca ggcaacgtgg cgtggtgtgc actgtgtttg ctgacgcaac      7243
ccccactggt tggggcattg ccaccacctg tcagctcctt tccgggactt tcgctttccc      7303
cctccctatt gccacggcgg aactcatcgc cgcctgcctt gcccgctgct ggacaggggc      7363
tcggctgttg ggcactgaca attccgtggt gttgtcgggg aagctgacgt cctttccatg      7423
gctgctcgcc tgtgttgcca cctggattct gcgcgggacg tccttctgct acgtcccttc      7483
ggccctcaat ccagcggacc ttccttcccg cggcctgctg ccggctctgc ggcctcttcc      7543
gcgtcttcgc cttcgccctc agacgagtcg gatctccctt tgggccgcct ccccgcctgg      7603
aattcgagct cggtaccttt aagaccaatg acttacaagg cagctgtaga tcttagccac      7663 ttttttaaaag aaaaggggggg actggaaggg ctaattcact cccaacgaag acaagatctg      7723 cttttttgctt gtactgggtc tctctggtta gaccagatct gagcctggga gctctctggc      7783
taactaggga acccactgct taagcctcaa taaagcttgc cttgagtgct tcaagtagtg      7843
tgtgcccgtc tgttgtgtga ctctggtaac tagagatccc tcagacccctt ttagtcagtg      7903 tggaaaatct ctagcagtag tagttcatgt catcttatta ttcagtattt ataacttgca      7963
aagaaatgaa tatcagagag tgagaggaac ttgtttattg cagcttataa tggttacaaa      8023
```

-continued

```
taaagcaata gcatcacaaa tttcacaaat aaagcatttt tttcactgca ttctagttgt   8083
ggtttgtcca aactcatcaa tgtatcttat catgtctggc tctagctatc ccgcccctaa   8143
ctccgcccag ttccgcccat tctccgcccc atggctgact aattttttt atttatgcag    8203 aggccgaggc cgcctcggcc tctgagctat tccagaagta gtgaggaggc tttttttggag  8263 gcctaggctt ttgcgtcgag acgtacccaa ttcgccctat agtgagtcgt attacgcgcg    8323
ctcactggcc gtcgttttac aacgtcgtga ctgggaaaac cctggcgtta cccaacttaa   8383
tcgccttgca gcacatcccc ctttcgccag ctggcgtaat agcgaagagg cccgcaccga   8443
tcgcccttcc caacagttgc gcagcctgaa tggcgaatgg cgcgacgcgc cctgtagcgg   8503
cgcattaagc gcggcgggtg tggtggttac gcgcagcgtg accgctacac ttgccagcgc   8563
cctagcgccc gctcctttcg ctttcttccc ttcctttctc gccacgttcg ccggctttcc   8623
ccgtcaagct ctaaatcggg ggctcccttt agggttccga tttagtgctt tacggcacct   8683
cgaccccaaa aaacttgatt agggtgatgg ttcacgtagt gggccatcgc cctgatagac   8743
ggtttttcgc cctttgacgt tggagtccac gttctttaat agtggactct gttccaaac   8803 tggaacaaca ctcaacccta tctcggtcta ttcttttgat ttataaggga ttttgccgat   8863
ttcggcctat tggttaaaaa atgagctgat ttaacaaaaa tttaacgcga attttaacaa   8923
aatattaacg tttacaattt cccaggtggc acttttcggg gaaatgtgcg cggaacccct   8983
atttgtttat ttttctaaat acattcaaat atgtatccgc tcatgagaca ataaccctga   9043
taaatgcttc aataatattg aaaaaggaag agtatgagta ttcaacattt ccgtgtcgcc   9103
cttattccct tttttgcggc attttgcctt cctgttttg ctcacccaga aacgctggtg     9163
aaagtaaaag atgctgaaga tcagttgggt gcacgagtgg gttacatcga actggatctc   9223
aacagcggta agatccttga gagttttcgc cccgaagaac gttttccaat gatgagcact   9283
tttaaagttc tgctatgtgg cgcggtatta tcccgtattg acgccgggca agagcaactc   9343
ggtcgccgca tacactattc tcagaatgac ttggttg                             9380
```

<210> SEQ ID NO 19
<211> LENGTH: 177
<212> TYPE: PRT
<213> ORGANISM: Artificial Sequence
<220> FEATURE:
<223> OTHER INFORMATION: [CDS]:4430..4963 from SEQ ID NO 18

<400> SEQUENCE: 19

```
Met Ala Trp Thr Val Leu Leu Leu Gly Leu Leu Ser His Cys Thr Gly
1               5                   10                  15

Ser Val Thr Ser Tyr Phe Gly Lys Leu Glu Ser Lys Leu Ser Val Ile
            20                  25                  30

Arg Asn Leu Asn Asp Gln Val Leu Phe Ile Asp Gln Gly Asn Arg Pro
        35                  40                  45

Leu Phe Glu Asp Met Thr Asp Ser Asp Cys Arg Asp Asn Ala Pro Arg
    50                  55                  60

Thr Ile Phe Ile Ile Ser Met Tyr Lys Asp Ser Gln Pro Arg Gly Met
65                  70                  75                  80

Ala Val Thr Ile Ser Val Lys Cys Glu Lys Ile Ser Thr Leu Ser Cys
                85                  90                  95

Glu Asn Lys Ile Ile Ser Phe Lys Glu Met Asn Pro Pro Asp Asn Ile
            100                 105                 110

Lys Asp Thr Lys Ser Asp Ile Ile Phe Phe Gln Arg Ser Val Pro Gly
```

```
             115                  120                  125

His Asp Asn Lys Met Gln Phe Glu Ser Ser Ser Tyr Glu Gly Tyr Phe
    130                  135                  140

Leu Ala Cys Glu Lys Glu Arg Asp Leu Phe Lys Leu Ile Leu Lys Lys
145                  150                  155                  160

Glu Asp Glu Leu Gly Asp Arg Ser Ile Met Phe Thr Val Gln Asn Glu
                 165                  170                  175

Asp
```

```
<210> SEQ ID NO 20
<211> LENGTH: 9684
<212> TYPE: DNA
<213> ORGANISM: Artificial Sequence
<220> FEATURE:
<223> OTHER INFORMATION: pCCL.PPT.NFATmIL2.EGFP.PGK.CAR.wPRE
<220> FEATURE:
<221> NAME/KEY: misc_signal
<222> LOCATION: 2683..2808
<223> OTHER INFORMATION: /note="HIV-1 packaging signal"
<220> FEATURE:
<221> NAME/KEY: misc_feature
<222> LOCATION: 3302..3543
<223> OTHER INFORMATION: /note="RRE: rev response element of HIV-1"
<220> FEATURE:
<221> NAME/KEY: misc_feature
<222> LOCATION: 4030..4147
<223> OTHER INFORMATION: /note="cPPT/CTScPPT/CTS: central polypurine
      tract and central termination sequence of HIV-1"
<220> FEATURE:
<221> NAME/KEY: promoter
<222> LOCATION: 4178..4414
<223> OTHER INFORMATION: /note="6x NFAT"
<220> FEATURE:
<221> NAME/KEY: promoter
<222> LOCATION: 4421..4540
<223> OTHER INFORMATION: /note="mIL2 promoter including TATA box"
<220> FEATURE:
<221> NAME/KEY: CDS
<222> LOCATION: 4559..5278
<223> OTHER INFORMATION: /note="eGFP"
      /transl_table=1
<220> FEATURE:
<221> NAME/KEY: promoter
<222> LOCATION: 5287..5802
<223> OTHER INFORMATION: /note="PGK promoter"
<220> FEATURE:
<221> NAME/KEY: gene
<222> LOCATION: 5834..7288
<223> OTHER INFORMATION: /gene="placeholder for CAR"
      /n=any nucleotide
<220> FEATURE:
<221> NAME/KEY: misc_signal
<222> LOCATION: 7315..7903
<223> OTHER INFORMATION: /note="wPRE: woodchuck hepatitis virus
      posttranscriptional regulatory element"

<400> SEQUENCE: 20
agtactcacc agtcacagaa aagcatctta cggatggcat gacagtaaga gaattatgca       60
gtgctgccat aaccatgagt gataacactg cggccaactt acttctgaca acgatcggag      120
gaccgaagga gctaaccgct tttttgcaca acatggggga tcatgtaact cgccttgatc      180
gttgggaacc ggagctgaat gaagccatac caaacgacga gcgtgacacc acgatgcctg      240
tagcaatggc aacaacgttg cgcaaactat taactggcga actacttact ctagcttccc      300
ggcaacaatt aatagactgg atggaggcgg ataaagttgc aggaccactt ctgcgctcgg      360
cccttccggc tggctggttt attgctgata aatctggagc cggtgagcgt gggtctcgcg      420
gtatcattgc agcactgggg ccagatggta agccctcccg tatcgtagtt atctacacga      480
```

-continued

```
cggggagtca ggcaactatg gatgaacgaa atagacagat cgctgagata ggtgcctcac      540
tgattaagca ttggtaactg tcagaccaag tttactcata tatactttag attgatttaa      600
aacttcattt ttaatttaaa aggatctagg tgaagatcct ttttgataat ctcatgacca      660
aaatccctta acgtgagttt tcgttccact gagcgtcaga ccccgtagaa aagatcaaag      720
gatcttcttg agatcctttt tttctgcgcg taatctgctg cttgcaaaca aaaaaaccac      780
cgctaccagc ggtggtttgt ttgccggatc aagagctacc aactcttttt ccgaaggtaa      840
ctggcttcag cagagcgcag ataccaaata ctgttcttct agtgtagccg tagttaggcc      900
accacttcaa gaactctgta gcaccgccta catacctcgc tctgctaatc ctgttaccag      960
tggctgctgc cagtggcgat aagtcgtgtc ttaccgggtt ggactcaaga cgatagttac     1020
cggataaggc gcagcggtcg ggctgaacgg ggggttcgtg cacacagccc agcttggagc     1080
gaacgaccta caccgaactg agatacctac agcgtgagct atgagaaagc gccacgcttc     1140
ccgaagggag aaaggcggac aggtatccgg taagcggcag ggtcggaaca ggagagcgca     1200
cgagggagct tccagggggga aacgcctggt atctttatag tcctgtcggg tttcgccacc     1260
tctgacttga gcgtcgattt ttgtgatgct cgtcaggggg gcggagccta tggaaaaacg     1320
ccagcaacgc ggcctttttta cggttcctgg ccttttgctg ccttttgct cacatgttct     1380 ttcctgcgtt atcccctgat tctgtggata accgtattac cgcctttgag tgagctgata     1440
ccgctcgccg cagccgaacg accgagcgca gcgagtcagt gagcgaggaa gcggaagagc     1500
gcccaatacg caaaccgcct ctccccgcgc gttggccgat tcattaatgc agctggcacg     1560
acaggtttcc cgactggaaa gcgggcagtg agcgcaacgc aattaatgtg agttagctca     1620
ctcattaggc accccaggct ttacacttta tgcttccggc tcgtatgttg tgtggaattg     1680
tgagcggata acaatttcac acaggaaaca gctatgacca tgattacgcc aagcgcgcaa     1740
ttaaccctca ctaaagggaa caaaagctgg agctgcaagc ttggccattg catacgttgt     1800
atccatatca taatatgtac atttatattg gctcatgtcc aacattaccg ccatgttgac     1860
attgattatt gactagttat taatagtaat caattacggg gtcattagtt catagcccat     1920
atatggagtt ccgcgttaca taacttacgg taaatggccc gcctggctga ccgcccaacg     1980 accccgccc attgacgtca ataatgacgt atgttcccat agtaacgcca atagggactt     2040
tccattgacg tcaatgggtg gagtatttac ggtaaactgc ccacttggca gtacatcaag     2100
tgtatcatat gccaagtacg cccctattg acgtcaatga cggtaaatgg cccgcctggc     2160
attatgccca gtacatgacc ttatgggact ttcctacttg gcagtacatc tacgtattag     2220
tcatcgctat taccatggtg atgcggtttt ggcagtacat caatgggcgt ggatagcggt     2280
ttgactcacg gggatttcca agtctccacc ccattgacgt caatgggagt ttgttttggc     2340
accaaaatca acgggacttt ccaaaatgtc gtaacaactc cgccccattg acgcaaatgg     2400
gcggtaggcg tgtacggtgg gaggtctata taagcagagc tcgtttagtg aaccggggtc     2460
tctctggtta gaccagatct gagcctggga gctctctggc taactaggga acccactgct     2520
taagcctcaa taaagcttgc cttgagtgct tcaagtagtg tgtgcccgtc tgttgtgtga     2580
ctctggtaac tagagatccc tcagaccctt ttagtcagtg tggaaaatct ctagcagtgg     2640
cgcccgaaca gggacttgaa agcgaaaggg aaaccagagg agctctctcg acgcaggact     2700
cggcttgctg aagcgcgcac ggcaagaggc gaggggcggc gactggtgag tacgccaaaa     2760
attttgacta gcggaggcta gaaggagaga gatgggtgcg agagcgtcag tattaagcgg     2820
gggagaatta gatcgcgatg gaaaaaaatt cggttaaggc caggggggaaa gaaaaaatat     2880
```

-continued

```
aaattaaaac atatagtatg ggcaagcagg gagctagaac gattcgcagt taatcctggc      2940
ctgttagaaa catcagaagg ctgtagacaa atactgggac agctacaacc atcccttcag      3000
acaggatcag aagaacttag atcattatat aatacagtag caaccctcta ttgtgtgcat      3060
caaaggatag agataaaaga caccaaggaa gctttagaca agatagagga agagcaaaac      3120
aaaagtaaga ccaccgcaca gcaagcggcc gctgatcttc agacctggag gaggagatat      3180
gagggacaat tggagaagtg aattatataa atataaagta gtaaaaattg aaccattagg      3240
agtagcaccc accaaggcaa agagaagagt ggtgcagaga gaaaaaagag cagtgggaat      3300
aggagctttg ttccttgggt tcttgggagc agcaggaagc actatgggcg cagcctcaat      3360
gacgctgacg gtacaggcca gacaattatt gtctggtata gtgcagcagc agaacaattt      3420
gctgagggct attgaggcgc aacagcatct gttgcaactc acagtctggg gcatcaagca      3480
gctccaggca agaatcctgg ctgtggaaag atacctaaag gatcaacagc tcctggggat      3540
ttggggttgc tctggaaaac tcatttgcac cactgctgtg ccttggaatg ctagttggag      3600
taataaatct ctggaacaga tttggaatca cacgacctgg atggagtggg acagagaaat      3660
taacaattac acaagcttaa tacactcctt aattgaagaa tcgcaaaacc agcaagaaaa      3720
gaatgaacaa gaattattgg aattagataa atgggcaagt ttgtggaatt ggtttaacat      3780
aacaaattgg ctgtggtata taaaattatt cataatgata gtaggaggct tggtaggttt      3840
aagaatagtt tttgctgtac tttctatagt gaatagagtt aggcagggat attcaccatt      3900
atcgtttcag acccacctcc caaccccgag gggacccgac aggcccgaag gaatagaaga      3960
agaaggtgga gagagagaca gagacagatc cattcgatta gtgaacggat ctcgacggta      4020
tcggttaact tttaaaagaa aaggggggat tggggggtac agtgcagggg aaagaatagt      4080
agacataata gcaacagaca tacaaactaa agaattacaa aaacaaatta caaaaattca      4140
aaattttatc gatcacgaga ctagcctcga cagcgctgat atcgaattag gaggaaaaac      4200
tgtttcatac agaaggcgtc aattaggagg aaaaactgtt tcatacagaa ggcgtcaatt      4260
aggaggaaaa actgtttcat acagaaggcg tcaattggtc ccatcgaatt aggaggaaaa      4320
actgtttcat acagaaggcg tcaattagga ggaaaaactg tttcatacag aaggcgtcaa      4380
ttaggaggaa aaactgtttc atacagaagg cgtcaattgg tcccgggaca ttttgacacc      4440
cccataatat ttttccagaa ttaacagtat aaattgcatc tcttgttcaa gagttcccta      4500
tcactctctt taatcactac tcacagtaac ctcaactcct ggatccacgc gtgccacc      4558 atg gtg agc aag ggc gag gag ctg ttc acc ggg gtg gtg ccc atc ctg      4606
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      4654
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc      4702
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc      4750
Cys Thr Thr Gly Lys Leu Pro Val Pro Trp Pro Thr Leu Val Thr Thr
    50                  55                  60 ctg acc tac ggc gtg cag tgc ttc agc cgc tac ccc gac cac atg aag      4798
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag      4846
Gln His Asp Phe Phe Lys Ser Ala Met Pro Glu Gly Tyr Val Gln Glu
```

-continued

```
                    85                  90                  95 cgc acc atc ttc ttc aag gac gac ggc aac tac aag acc cgc gcc gag    4894
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc    4942
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac    4990
Ile Asp Phe Lys Glu Asp Gly Asn Ile Leu Gly His Lys Leu Glu Tyr
        130                 135                 140 aac tac aac agc cac aac gtc tat atc atg gcc gac aag cag aag aac    5038
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc    5086
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc    5134
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg    5182
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc    5230
Ser Lys Asp Pro Asn Glu Lys Arg Asp His Met Val Leu Leu Glu Phe
        210                 215                 220 gtg acc gcc gcc ggg atc act ctc ggc atg gac gag ctg tac aag taa    5278
Val Thr Ala Ala Gly Ile Thr Leu Gly Met Asp Glu Leu Tyr Lys
225                 230                 235 tcgaattccc acggggttgg ggttgcgcct tttccaaggc agccctgggt ttgcgcaggg    5338
acgcggctgc tctgggcgtg gttccgggaa acgcagcggc gccgaccctg ggtctcgcac    5398
attcttcacg tccgttcgca gcgtcacccg gatcttcgcc gctacccttg tgggcccccc    5458
ggcgacgctt cctgctccgc ccctaagtcg ggaaggttcc ttgcggttcg cggcgtgccg    5518
gacgtgacaa acggaagccg cacgtctcac tagtaccctc gcagacggac agcgccaggg    5578
agcaatggca gcgcgccgac cgcgatgggc tgtggccaat agcggctgct cagcggggcg    5638
cgccgagagc agcggccggg aagggggcggt gcgggaggcg gggtgtgggg cggtagtgtg    5698
ggccctgttc ctgcccgcgc ggtgttccgc attctgcaag cctccggagc gcacgtcggc    5758
agtcggctcc ctcgttgacc gaatcaccga cctctctccc caggggatc caccggtcac     5818 gtggctagcg ccaccnnnnn nnnnnnnnnn nnnnnnnnnn nnnnnnnnnn nnnnnnnnnn    5878
nnnnnnnnnn nnnnnnnnnn nnnnnnnnnn nnnnnnnnnn nnnnnnnnnn nnnnnnnnnn    5938
nnnnnnnnnn nnnnnnnnnn nnnnnnnnnn nnnnnnnnnn nnnnnnnnnn nnnnnnnnnn    5998
nnnnnnnnnn nnnnnnnnnn nnnnnnnnnn nnnnnnnnnn nnnnnnnnnn nnnnnnnnnn    6058
nnnnnnnnnn nnnnnnnnnn nnnnnnnnnn nnnnnnnnnn nnnnnnnnnn nnnnnnnnnn    6118
nnnnnnnnnn nnnnnnnnnn nnnnnnnnnn nnnnnnnnnn nnnnnnnnnn nnnnnnnnnn    6178
nnnnnnnnnn nnnnnnnnnn nnnnnnnnnn nnnnnnnnnn nnnnnnnnnn nnnnnnnnnn    6238
nnnnnnnnnn nnnnnnnnnn nnnnnnnnnn nnnnnnnnnn nnnnnnnnnn nnnnnnnnnn    6298
nnnnnnnnnn nnnnnnnnnn nnnnnnnnnn nnnnnnnnnn nnnnnnnnnn nnnnnnnnnn    6358
nnnnnnnnnn nnnnnnnnnn nnnnnnnnnn nnnnnnnnnn nnnnnnnnnn nnnnnnnnnn    6418
nnnnnnnnnn nnnnnnnnnn nnnnnnnnnn nnnnnnnnnn nnnnnnnnnn nnnnnnnnnn    6478
nnnnnnnnnn nnnnnnnnnn nnnnnnnnnn nnnnnnnnnn nnnnnnnnnn nnnnnnnnnn    6538
```

-continued

```
nnnnnnnnnn nnnnnnnnnn nnnnnnnnnn nnnnnnnnnn nnnnnnnnnn nnnnnnnnnn   6598
nnnnnnnnnn nnnnnnnnnn nnnnnnnnnn nnnnnnnnnn nnnnnnnnnn nnnnnnnnnn   6658
nnnnnnnnnn nnnnnnnnnn nnnnnnnnnn nnnnnnnnnn nnnnnnnnnn nnnnnnnnnn   6718
nnnnnnnnnn nnnnnnnnnn nnnnnnnnnn nnnnnnnnnn nnnnnnnnnn nnnnnnnnnn   6778
nnnnnnnnnn nnnnnnnnnn nnnnnnnnnn nnnnnnnnnn nnnnnnnnnn nnnnnnnnnn   6838
nnnnnnnnnn nnnnnnnnnn nnnnnnnnnn nnnnnnnnnn nnnnnnnnnn nnnnnnnnnn   6898
nnnnnnnnnn nnnnnnnnnn nnnnnnnnnn nnnnnnnnnn nnnnnnnnnn nnnnnnnnnn   6958
nnnnnnnnnn nnnnnnnnnn nnnnnnnnnn nnnnnnnnnn nnnnnnnnnn nnnnnnnnnn   7018
nnnnnnnnnn nnnnnnnnnn nnnnnnnnnn nnnnnnnnnn nnnnnnnnnn nnnnnnnnnn   7078
nnnnnnnnnn nnnnnnnnnn nnnnnnnnnn nnnnnnnnnn nnnnnnnnnn nnnnnnnnnn   7138
nnnnnnnnnn nnnnnnnnnn nnnnnnnnnn nnnnnnnnnn nnnnnnnnnn nnnnnnnnnn   7198
nnnnnnnnnn nnnnnnnnnn nnnnnnnnnn nnnnnnnnnn nnnnnnnnnn nnnnnnnnnn   7258
nnnnnnnnnn nnnnnnnnnn nnnnnnnnnn taggatccgc cggcggccgc gtcgacaatc   7318
aacctctgga ttacaaaatt tgtgaaagat tgactggtat tcttaactat gttgctcctt   7378
ttacgctatg tggatacgct gctttaatgc ctttgtatca tgctattgct tcccgtatgg   7438
ctttcatttt ctcctccttg tataaatcct ggttgctgtc tctttatgag gagttgtggc   7498
ccgttgtcag gcaacgtggc gtggtgtgca ctgtgtttgc tgacgcaacc cccactggtt   7558
ggggcattgc caccacctgt cagctccttt ccgggacttt cgctttcccc ctccctattg   7618
ccacggcgga actcatcgcc gcctgccttg cccgctgctg gacaggggct cggctgttgg   7678
gcactgacaa ttccgtggtg ttgtcgggga agctgacgtc ctttccatgg ctgctcgcct   7738
gtgttgccac ctggattctg cgcgggacgt ccttctgcta cgtcccttcg ccctcaatc   7798 cagcggacct tccttcccgc ggcctgctgc cggctctgcg gcctcttccg cgtcttcgcc   7858
ttcgccctca gacgagtcgg atctcccttt gggccgcctc cccgcctgga attcgagctc   7918 ggtacctttta agaccaatga cttacaaggc agctgtagat cttagccact tttttaaaaga   7978 aaagggggga ctggaagggc taattcactc ccaacgaaga caagatctgc tttttgcttg   8038
tactgggtct ctctggttag accagatctg agcctgggag ctctctggct aactagggaa   8098
cccactgctt aagcctcaat aaagcttgcc ttgagtgctt caagtagtgt gtgcccgtct   8158
gttgtgtgac tctggtaact agagatccct cagacccttt tagtcagtgt ggaaaatctc   8218
tagcagtagt agttcatgtc atcttattat tcagtattta aacttgcaa agaaatgaat   8278 atcagagagt gagaggaact tgtttattgc agcttataat ggttacaaat aaagcaatag   8338
catcacaaat ttcacaaata aagcattttt ttcactgcat tctagttgtg gtttgtccaa   8398
actcatcaat gtatcttatc atgtctggct ctagctatcc cgcccctaac tccgcccagt   8458
tccgcccatt ctccgcccca tggctgacta attttttttta tttatgcaga ggccgaggcc   8518
gcctcggcct ctgagctatt ccagaagtag tgaggaggct ttttttggagg cctaggcttt   8578 tgcgtcgaga cgtacccaat tcgccctata gtgagtcgta ttacgcgcgc tcactggccg   8638
tcgttttaca acgtcgtgac tgggaaaacc ctggcgttac ccaacttaat cgccttgcag   8698
cacatccccc tttcgccagc tggcgtaata gcgaagaggc ccgcaccgat cgcccttccc   8758
aacagttgcg cagcctgaat ggcgaatggc gcgacgcgcc ctgtagcggc gcattaagcg   8818
cggcgggtgt ggtggttacg cgcagcgtga ccgctacact tgccagcgcc ctagcgcccg   8878
```

-continued

```
ctcctttcgc tttcttccct tcctttctcg ccacgttcgc cggctttccc cgtcaagctc   8938
taaatcgggg gctcccttta gggttccgat ttagtgcttt acggcacctc gaccccaaaa   8998
aacttgatta gggtgatggt tcacgtagtg ggccatcgcc ctgatagacg gtttttcgcc   9058
ctttgacgtt ggagtccacg ttctttaata gtggactctt gttccaaact ggaacaacac   9118
tcaaccctat ctcggtctat tcttttgatt tataagggat tttgccgatt tcggcctatt   9178
ggttaaaaaa tgagctgatt taacaaaaat ttaacgcgaa ttttaacaaa atattaacgt   9238
ttacaatttc ccaggtggca cttttcgggg aaatgtgcgc ggaacccta tttgtttatt     9298 tttctaaata cattcaaata tgtatccgct catgagacaa taaccctgat aaatgcttca   9358
ataatattga aaaaggaaga gtatgagtat tcaacatttc cgtgtcgccc ttattcccctt   9418 ttttgcggca ttttgccttc ctgttttttgc tcacccagaa acgctggtga agtaaaaga    9478 tgctgaagat cagttgggtg cacgagtggg ttacatcgaa ctggatctca acagcggtaa   9538
gatccttgag agttttcgcc ccgaagaacg ttttccaatg atgagcactt ttaaagttct     9598
gctatgtggc gcggtattat cccgtattga cgccgggcaa gagcaactcg gtcgccgcat   9658
acactattct cagaatgact tggttg                                          9684
```

<210> SEQ ID NO 21
<211> LENGTH: 239
<212> TYPE: PRT
<213> ORGANISM: Artificial Sequence
<220> FEATURE:
<223> OTHER INFORMATION: [CDS]:4559..5278 from SEQ ID NO 20

<400> SEQUENCE: 21

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220
```

-continued

```
Val Thr Ala Ala Gly Ile Thr Leu Gly Met Asp Glu Leu Tyr Lys
225                 230                 235

<210> SEQ ID NO 22
<211> LENGTH: 10598
<212> TYPE: DNA
<213> ORGANISM: Artificial Sequence
<220> FEATURE:
<223> OTHER INFORMATION: pCCL.PPT.NFATmIL2.humanIL12.PGK.CAR.wPRE
<220> FEATURE:
<221> NAME/KEY: misc_signal
<222> LOCATION: 2683..2808
<223> OTHER INFORMATION: /note="HIV-1 psi: packaging signal of human
      immunodeficiency virus type 1"
<220> FEATURE:
<221> NAME/KEY: misc_signal
<222> LOCATION: 3302..3543
<223> OTHER INFORMATION: /note="RRE: rev response element of HIV-1"
<220> FEATURE:
<221> NAME/KEY: misc_feature
<222> LOCATION: 4030..4147
<223> OTHER INFORMATION: /note="cPPT/CTScPPT/CTS: central polypurine
      tract and central termination sequence of HIV-1"
<220> FEATURE:
<221> NAME/KEY: promoter
<222> LOCATION: 4178..4414
<223> OTHER INFORMATION: /note="6 x NFAT"
<220> FEATURE:
<221> NAME/KEY: promoter
<222> LOCATION: 4421..4540
<223> OTHER INFORMATION: /note="mIL2 promoter"
<220> FEATURE:
<221> NAME/KEY: CDS
<222> LOCATION: 4559..6181
<223> OTHER INFORMATION: /gene="sc Il12 humanized codon usage"
      /transl_table=1
<220> FEATURE:
<221> NAME/KEY: promoter
<222> LOCATION: 6201..6716
<223> OTHER INFORMATION: /note="PGK promoter"
<220> FEATURE:
<221> NAME/KEY: gene
<222> LOCATION: 6748..8202
<223> OTHER INFORMATION: /gene="placeholder for CAR"
      /n=any nucleotide
<220> FEATURE:
<221> NAME/KEY: misc_signal
<222> LOCATION: 8229..8817
<223> OTHER INFORMATION: /note="wPRE: woodchuck hepatitis virus
      posttranscriptional regulatory element"

<400> SEQUENCE: 22
agtactcacc agtcacagaa aagcatctta cggatggcat gacagtaaga gaattatgca        60
gtgctgccat aaccatgagt gataacactg cggccaactt acttctgaca acgatcggag       120
gaccgaagga gctaaccgct tttttgcaca acatgggggga tcatgtaact cgccttgatc       180
gttgggaacc ggagctgaat gaagccatac caaacgacga gcgtgacacc acgatgcctg       240
tagcaatggc aacaacgttg cgcaaactat taactggcga actacttact ctagcttccc       300
ggcaacaatt aatagactgg atggaggcgg ataaagttgc aggaccactt ctgcgctcgg       360
cccttccggc tggctggttt attgctgata atctggagc cggtgagcgt gggtctcgcg       420
gtatcattgc agcactgggg ccagatggta agccctcccg tatcgtagtt atctacacga       480
cggggagtca ggcaactatg gatgaacgaa atagacagat cgctgagata ggtgcctcac       540
tgattaagca ttggtaactg tcagaccaag tttactcata tatactttag attgatttaa       600
aacttcattt ttaatttaaa aggatctagg tgaagatcct ttttgataat ctcatgacca       660
aaatccctta acgtgagttt tcgttccact gagcgtcaga ccccgtagaa aagatcaaag       720
```

-continued

```
gatcttcttg agatcctttt tttctgcgcg taatctgctg cttgcaaaca aaaaaaccac      780
cgctaccagc ggtggtttgt ttgccggatc aagagctacc aactcttttt ccgaaggtaa      840
ctggcttcag cagagcgcag ataccaaata ctgttcttct agtgtagccg tagttaggcc      900
accacttcaa gaactctgta gcaccgccta catacctcgc tctgctaatc ctgttaccag      960
tggctgctgc cagtggcgat aagtcgtgtc ttaccgggtt ggactcaaga cgatagttac     1020
cggataaggc gcagcggtcg ggctgaacgg ggggttcgtg cacacagccc agcttggagc     1080
gaacgaccta caccgaactg agatacctac agcgtgagct atgagaaagc gccacgcttc     1140
ccgaagggag aaaggcggac aggtatccgg taagcggcag ggtcggaaca ggagagcgca     1200
cgagggagct tccaggggga aacgcctggt atctttatag tcctgtcggg tttcgccacc     1260
tctgacttga gcgtcgattt ttgtgatgct cgtcaggggg gcggagccta tggaaaaacg     1320
ccagcaacgc ggccttttta cggttcctgg ccttttgctg gcctttttgct cacatgttct     1380 ttcctgcgtt atccctgat tctgtggata accgtattac cgcctttgag tgagctgata     1440
ccgctcgccg cagccgaacg accgagcgca gcgagtcagt gagcgaggaa gcggaagagc     1500
gcccaatacg caaaccgcct ctccccgcgc gttggccgat tcattaatgc agctggcacg     1560
acaggtttcc cgactggaaa gcgggcagtg agcgcaacgc aattaatgtg agttagctca     1620
ctcattaggc accccaggct ttacacttta tgcttccggc tcgtatgttg tgtggaattg     1680
tgagcggata acaatttcac acaggaaaca gctatgacca tgattacgcc aagcgcgcaa     1740
ttaaccctca ctaaagggaa caaaagctgg agctgcaagc ttggccattg catacgttgt     1800
atccatatca taatatgtac atttatattg gctcatgtcc aacattaccg ccatgttgac     1860
attgattatt gactagttat taatagtaat caattacggg gtcattagtt catagcccat     1920
atatggagtt ccgcgttaca taacttacgg taaatggccc gcctggctga ccgcccaacg     1980
acccccgccc attgacgtca ataatgacgt atgttcccat agtaacgcca atagggactt     2040
tccattgacg tcaatgggtg gagtatttac ggtaaactgc ccacttggca gtacatcaag     2100
tgtatcatat gccaagtacg ccccctattg acgtcaatga cggtaaatgg cccgcctggc     2160
attatgccca gtacatgacc ttatgggact ttcctacttg gcagtacatc tacgtattag     2220
tcatcgctat taccatggtg atgcggtttt ggcagtacat caatgggcgt ggatagcggt     2280
ttgactcacg gggatttcca agtctccacc ccattgacgt caatgggagt ttgttttggc     2340
accaaaatca acgggacttt ccaaaatgtc gtaacaactc cgccccattg acgcaaatgg     2400
gcggtaggcg tgtacggtgg gaggtctata taagcagagc tcgtttagtg aaccggggtc     2460
tctctggtta gaccagatct gagcctggga gctctctggc taactaggga acccactgct     2520
taagcctcaa taaagcttgc cttgagtgct tcaagtagtg tgtgcccgtc tgttgtgtga     2580
ctctggtaac tagagatccc tcagaccctt ttagtcagtg tggaaaatct ctagcagtgg     2640
cgcccgaaca gggacttgaa agcgaaaggg aaaccagagg agctctctcg acgcaggact     2700
cggcttgctg aagcgcgcac ggcaagaggc gaggggcggc gactggtgag tacgccaaaa     2760
attttgacta gcggaggcta gaaggagaga gatgggtgcg agagcgtcag tattaagcgg     2820
gggagaatta gatcgcgatg gaaaaaaatt cggttaaggc cagggggaaa gaaaaaatat     2880
aaattaaaac atatagtatg ggcaagcagg gagctagaac gattcgcagt taatcctggc     2940
ctgttagaaa catcagaagg ctgtagacaa atactgggac agctacaacc atcccttcag     3000
acaggatcag aagaacttag atcattatat aatacagtag caaccctcta ttgtgtgcat     3060
caaaggatag agataaaaga caccaaggaa gctttagaca agatagagga gagcaaaac     3120
```

-continued

```
aaaagtaaga ccaccgcaca gcaagcggcc gctgatcttc agacctggag gaggagatat    3180
gagggacaat tggagaagtg aattatataa atataaagta gtaaaaattg aaccattagg    3240
agtagcaccc accaaggcaa agagaagagt ggtgcagaga gaaaaaagag cagtgggaat    3300
aggagctttg ttccttgggt tcttgggagc agcaggaagc actatgggcg cagcctcaat    3360
gacgctgacg gtacaggcca gacaattatt gtctggtata gtgcagcagc agaacaattt    3420
gctgagggct attgaggcgc aacagcatct gttgcaactc acagtctggg gcatcaagca    3480
gctccaggca agaatcctgg ctgtggaaag atacctaaag gatcaacagc tcctggggat    3540
ttggggttgc tctggaaaac tcatttgcac cactgctgtg ccttggaatg ctagttggag    3600
taataaatct ctggaacaga tttggaatca cacgacctgg atggagtggg acagagaaat    3660
taacaattac acaagcttaa tacactcctt aattgaagaa tcgcaaaacc agcaagaaaa    3720
gaatgaacaa gaattattgg aattagataa atgggcaagt ttgtggaatt ggtttaacat    3780
aacaaattgg ctgtggtata taaaattatt cataatgata gtaggaggct tggtaggttt    3840
aagaatagtt tttgctgtac tttctatagt gaatagagtt aggcagggat attcaccatt    3900
atcgtttcag acccacctcc caaccccgag gggacccgac aggcccgaag gaatagaaga    3960
agaaggtgga gagagagaca gagacagatc cattcgatta gtgaacggat ctcgacggta    4020
tcggttaact tttaaaagaa aaggggggat tggggggtac agtgcagggg aaagaatagt    4080
agacataata gcaacagaca tacaaactaa agaattacaa aaacaaatta caaaaattca    4140
aaattttatc gatcacgaga ctagcctcga cagcgctgat atcgaattag gaggaaaaac    4200
tgtttcatac agaaggcgtc aattaggagg aaaaactgtt tcatacagaa ggcgtcaatt    4260
aggaggaaaa actgtttcat acagaaggcg tcaattggtc ccatcgaatt aggaggaaaa    4320
actgtttcat acagaaggcg tcaattagga ggaaaaactg tttcatacag aaggcgtcaa    4380
ttaggaggaa aaactgtttc atacagaagg cgtcaattgg tcccgggaca ttttgacacc    4440
cccataatat ttttccagaa ttaacagtat aaattgcatc tcttgttcaa gagttcccta    4500
tcactctctt taatcactac tcacagtaac ctcaactcct ggatccacgc gtgccacc      4558
```

```
atg tgt cac cag cag ctg gtc atc agc tgg ttc agc ctg gtg ttc ctg      4606
Met Cys His Gln Gln Leu Val Ile Ser Trp Phe Ser Leu Val Phe Leu
1               5                   10                  15 gcc tct cct ctg gtg gcc atc tgg gag ctg aag aaa gac gtg tac gtg      4654
Ala Ser Pro Leu Val Ala Ile Trp Glu Leu Lys Lys Asp Val Tyr Val
                20                  25                  30 gtg gaa ctg gac tgg tat ccc gat gct cct ggc gag atg gtg gtg ctg      4702
Val Glu Leu Asp Trp Tyr Pro Asp Ala Pro Gly Glu Met Val Val Leu
            35                  40                  45 acc tgc gat acc cct gaa gag gac ggc atc acc tgg aca ctg gat cag      4750
Thr Cys Asp Thr Pro Glu Glu Asp Gly Ile Thr Trp Thr Leu Asp Gln
        50                  55                  60 tct agc gag gtg ctc ggc agc ggc aag acc ctg acc atc caa gtg aaa      4798
Ser Ser Glu Val Leu Gly Ser Gly Lys Thr Leu Thr Ile Gln Val Lys
65                  70                  75                  80 gag ttt ggc gac gcc ggc cag tac acc tgt cac aaa ggc gga gaa gtg      4846
Glu Phe Gly Asp Ala Gly Gln Tyr Thr Cys His Lys Gly Gly Glu Val
                    85                  90                  95 ctg agc cac agc ctg ctg ctg ctc cac aag aaa gag gat ggc att tgg      4894
Leu Ser His Ser Leu Leu Leu Leu His Lys Lys Glu Asp Gly Ile Trp
                100                 105                 110 agc acc gac atc ctg aag gac cag aaa gag ccc aag aac aag acc ttc      4942
Ser Thr Asp Ile Leu Lys Asp Gln Lys Glu Pro Lys Asn Lys Thr Phe
```

-continued

```
                    115                     120                     125 ctg aga tgc gag gcc aag aac tac agc ggc cgg ttc aca tgt tgg tgg      4990
Leu Arg Cys Glu Ala Lys Asn Tyr Ser Gly Arg Phe Thr Cys Trp Trp
    130                 135                 140 ctg acc acc atc agc acc gac ctg acc ttc agc gtg aag tcc agc aga      5038
Leu Thr Thr Ile Ser Thr Asp Leu Thr Phe Ser Val Lys Ser Ser Arg
145                 150                 155                 160 ggc agc agt gat cct cag ggc gtt aca tgt ggc gcc gct aca ctg tct      5086
Gly Ser Ser Asp Pro Gln Gly Val Thr Cys Gly Ala Ala Thr Leu Ser
                165                 170                 175 gcc gaa aga gtg cgg ggc gac aac aaa gaa tac gag tac agc gtg gaa      5134
Ala Glu Arg Val Arg Gly Asp Asn Lys Glu Tyr Glu Tyr Ser Val Glu
                180                 185                 190 tgc caa gag gac agc gcc tgt cca gcc gcc gaa gag tct ctg cct atc      5182
Cys Gln Glu Asp Ser Ala Cys Pro Ala Ala Glu Glu Ser Leu Pro Ile
            195                 200                 205 gaa gtg atg gtg gac gcc gtg cac aag ctg aag tac gag aac tac acc      5230
Glu Val Met Val Asp Ala Val His Lys Leu Lys Tyr Glu Asn Tyr Thr
    210                 215                 220 tcc agc ttt ttc atc cgg gac atc atc aag ccc gat cct cca aag aac      5278
Ser Ser Phe Phe Ile Arg Asp Ile Ile Lys Pro Asp Pro Pro Lys Asn
225                 230                 235                 240 ctg cag ctg aag cct ctg aag aac agc aga cag gtg gaa gtg tcc tgg      5326
Leu Gln Leu Lys Pro Leu Lys Asn Ser Arg Gln Val Glu Val Ser Trp
                245                 250                 255 gag tac ccc gac acc tgg tct aca ccc cac agc tac ttc agc ctg acc      5374
Glu Tyr Pro Asp Thr Trp Ser Thr Pro His Ser Tyr Phe Ser Leu Thr
                260                 265                 270 ttt tgc gtg caa gtg cag ggc aag tcc aag cgc gag aaa aag gac cgg      5422
Phe Cys Val Gln Val Gln Gly Lys Ser Lys Arg Glu Lys Lys Asp Arg
            275                 280                 285 gtg ttc acc gac aag acc agc gcc acc gtg atc tgc aga aag aac gcc      5470
Val Phe Thr Asp Lys Thr Ser Ala Thr Val Ile Cys Arg Lys Asn Ala
    290                 295                 300 agc atc agc gtc aga gcc cag gac cgc tac tac agc agc tct tgg agc      5518
Ser Ile Ser Val Arg Ala Gln Asp Arg Tyr Tyr Ser Ser Ser Trp Ser
305                 310                 315                 320 gaa tgg gcc agc gtg cca tgt tct ggt ggc gga gga tct ggc gga ggt      5566
Glu Trp Ala Ser Val Pro Cys Ser Gly Gly Gly Gly Ser Gly Gly Gly
                325                 330                 335 gga agc ggc gga ggc gga tct aga aat ctg cct gtg gcc act cct gat      5614
Gly Ser Gly Gly Gly Gly Ser Arg Asn Leu Pro Val Ala Thr Pro Asp
                340                 345                 350 cct ggc atg ttc cct tgt ctg cac cac agc cag aac ctg ctg aga gcc      5662
Pro Gly Met Phe Pro Cys Leu His His Ser Gln Asn Leu Leu Arg Ala
                355                 360                 365 gtg tcc aac atg ctg cag aag gcc aga cag acc ctg gaa ttc tac ccc      5710
Val Ser Asn Met Leu Gln Lys Ala Arg Gln Thr Leu Glu Phe Tyr Pro
    370                 375                 380 tgc acc agc gag gaa atc gac cac gag gac atc acc aag gat aag acc      5758
Cys Thr Ser Glu Glu Ile Asp His Glu Asp Ile Thr Lys Asp Lys Thr
385                 390                 395                 400 agt acc gtg gaa gcc tgc ctg cct ctg gaa ctg acc aag aac gag agc      5806
Ser Thr Val Glu Ala Cys Leu Pro Leu Glu Leu Thr Lys Asn Glu Ser
                405                 410                 415 tgc ctg aac agc cgg gaa acc agc ttc atc acc aac ggc tct tgc ctg      5854
Cys Leu Asn Ser Arg Glu Thr Ser Phe Ile Thr Asn Gly Ser Cys Leu
                420                 425                 430 gcc agc aga aag acc tcc ttc atg atg gcc ctg tgc ctg agc agc atc      5902
```

-continued

```
Ala Ser Arg Lys Thr Ser Phe Met Met Ala Leu Cys Leu Ser Ser Ile
        435             440             445 tac gag gac ctg aag atg tac cag gtg gaa ttc aag acc atg aac gcc      5950
Tyr Glu Asp Leu Lys Met Tyr Gln Val Glu Phe Lys Thr Met Asn Ala
    450             455             460 aag ctg ctg atg gac ccc aag cgg cag atc ttc ctg gac cag aat atg      5998
Lys Leu Leu Met Asp Pro Lys Arg Gln Ile Phe Leu Asp Gln Asn Met
465             470             475             480 ctg gcc gtg atc gac gag ctg atg cag gcc ctg aac ttc aac agc gag      6046
Leu Ala Val Ile Asp Glu Leu Met Gln Ala Leu Asn Phe Asn Ser Glu
                485             490             495 aca gtg ccc cag aag tct agc ctg gaa gaa ccc gac ttc tac aag acc      6094
Thr Val Pro Gln Lys Ser Ser Leu Glu Glu Pro Asp Phe Tyr Lys Thr
            500             505             510 aag atc aag ctg tgc atc ctg ctg cac gcc ttc cgc atc aga gcc gtg      6142
Lys Ile Lys Leu Cys Ile Leu Leu His Ala Phe Arg Ile Arg Ala Val
            515             520             525 acc atc gat aga gtg atg agc tac ctg aac gcc tcc tga tgtacaagta      6191
Thr Ile Asp Arg Val Met Ser Tyr Leu Asn Ala Ser
    530             535             540 atcgaattcc cacggggttg gggttgcgcc ttttccaagg cagccctggg tttgcgcagg      6251
gacgcggctg ctctgggcgt ggttccggga aacgcagcgg cgccgaccct gggtctcgca      6311
cattcttcac gtccgttcgc agcgtcaccc ggatcttcgc cgctacccct gtgggccccc      6371
cggcgacgct tcctgctccg cccctaagtc gggaaggttc cttgcggttc gcggcgtgcc      6431
ggacgtgaca aacggaagcc gcacgtctca ctagtaccct cgcagacgga cagcgccagg      6491
gagcaatggc agcgcgccga ccgcgatggg ctgtggccaa tagcggctgc tcagcggggc      6551
gcgccgagag cagcggccgg gaaggggcgg tgcgggaggc ggggtgtggg gcggtagtgt      6611
gggccctgtt cctgcccgcg cggtgttccg cattctgcaa gcctccggag cgcacgtcgg      6671
cagtcggctc cctcgttgac cgaatcaccg acctctctcc ccaggggggat ccaccggtca      6731 cgtggctagc gccaccnnnn nnnnnnnnnn nnnnnnnnnn nnnnnnnnnn nnnnnnnnnn      6791
nnnnnnnnnn nnnnnnnnnn nnnnnnnnnn nnnnnnnnnn nnnnnnnnnn nnnnnnnnnn      6851
nnnnnnnnnn nnnnnnnnnn nnnnnnnnnn nnnnnnnnnn nnnnnnnnnn nnnnnnnnnn      6911
nnnnnnnnnn nnnnnnnnnn nnnnnnnnnn nnnnnnnnnn nnnnnnnnnn nnnnnnnnnn      6971
nnnnnnnnnn nnnnnnnnnn nnnnnnnnnn nnnnnnnnnn nnnnnnnnnn nnnnnnnnnn      7031
nnnnnnnnnn nnnnnnnnnn nnnnnnnnnn nnnnnnnnnn nnnnnnnnnn nnnnnnnnnn      7091
nnnnnnnnnn nnnnnnnnnn nnnnnnnnnn nnnnnnnnnn nnnnnnnnnn nnnnnnnnnn      7151
nnnnnnnnnn nnnnnnnnnn nnnnnnnnnn nnnnnnnnnn nnnnnnnnnn nnnnnnnnnn      7211
nnnnnnnnnn nnnnnnnnnn nnnnnnnnnn nnnnnnnnnn nnnnnnnnnn nnnnnnnnnn      7271
nnnnnnnnnn nnnnnnnnnn nnnnnnnnnn nnnnnnnnnn nnnnnnnnnn nnnnnnnnnn      7331
nnnnnnnnnn nnnnnnnnnn nnnnnnnnnn nnnnnnnnnn nnnnnnnnnn nnnnnnnnnn      7391
nnnnnnnnnn nnnnnnnnnn nnnnnnnnnn nnnnnnnnnn nnnnnnnnnn nnnnnnnnnn      7451
nnnnnnnnnn nnnnnnnnnn nnnnnnnnnn nnnnnnnnnn nnnnnnnnnn nnnnnnnnnn      7511
nnnnnnnnnn nnnnnnnnnn nnnnnnnnnn nnnnnnnnnn nnnnnnnnnn nnnnnnnnnn      7571
nnnnnnnnnn nnnnnnnnnn nnnnnnnnnn nnnnnnnnnn nnnnnnnnnn nnnnnnnnnn      7631
nnnnnnnnnn nnnnnnnnnn nnnnnnnnnn nnnnnnnnnn nnnnnnnnnn nnnnnnnnnn      7691
nnnnnnnnnn nnnnnnnnnn nnnnnnnnnn nnnnnnnnnn nnnnnnnnnn nnnnnnnnnn      7751
```

-continued

```
nnnnnnnnnn nnnnnnnnnn nnnnnnnnnn nnnnnnnnnn nnnnnnnnnn nnnnnnnnnn      7811
nnnnnnnnnn nnnnnnnnnn nnnnnnnnnn nnnnnnnnnn nnnnnnnnnn nnnnnnnnnn      7871
nnnnnnnnnn nnnnnnnnnn nnnnnnnnnn nnnnnnnnnn nnnnnnnnnn nnnnnnnnnn      7931
nnnnnnnnnn nnnnnnnnnn nnnnnnnnnn nnnnnnnnnn nnnnnnnnnn nnnnnnnnnn      7991
nnnnnnnnnn nnnnnnnnnn nnnnnnnnnn nnnnnnnnnn nnnnnnnnnn nnnnnnnnnn      8051
nnnnnnnnnn nnnnnnnnnn nnnnnnnnnn nnnnnnnnnn nnnnnnnnnn nnnnnnnnnn      8111
nnnnnnnnnn nnnnnnnnnn nnnnnnnnnn nnnnnnnnnn nnnnnnnnnn nnnnnnnnnn      8171
nnnnnnnnnn nnnnnnnnnn nnnnnnnnnn ntaggatccg ccggcggccg cgtcgacaat      8231
caacctctgg attacaaaat ttgtgaaaga ttgactggta ttcttaacta tgttgctcct      8291
tttacgctat gtggatacgc tgctttaatg cctttgtatc atgctattgc ttcccgtatg      8351
gctttcattt tctcctcctt gtataaatcc tggttgctgt ctctttatga ggagttgtgg      8411
cccgttgtca ggcaacgtgg cgtggtgtgc actgtgtttg ctgacgcaac ccccactggt      8471
tggggcattg ccaccacctg tcagctcctt tccgggactt tcgctttccc cctccctatt      8531
gccacggcgg aactcatcgc cgcctgcctt gcccgctgct ggacaggggc tcggctgttg      8591
ggcactgaca attccgtggt gttgtcgggg aagctgacgt cctttccatg gctgctcgcc      8651
tgtgttgcca cctggattct gcgcgggacg tccttctgct acgtcccttc ggccctcaat      8711
ccagcggacc ttccttcccg cggcctgctg ccggctctgc ggcctcttcc gcgtcttcgc      8771
cttcgccctc agacgagtcg gatctccctt tgggccgcct cccgcctgg aattcgagct      8831 cggtaccttt aagaccaatg acttacaagg cagctgtaga tcttagccac tttttaaaag      8891 aaaaggggg actggaaggg ctaattcact cccaacgaag acaagatctg cttttttgctt      8951 gtactgggtc tctctggtta gaccagatct gagcctggga gctctctggc taactaggga      9011
acccactgct taagcctcaa taaagcttgc cttgagtgct tcaagtagtg tgtgcccgtc      9071
tgttgtgtga ctctggtaac tagagatccc tcagaccctt ttagtcagtg tggaaaatct      9131
ctagcagtag tagttcatgt catcttatta ttcagtattt ataacttgca aagaaatgaa      9191
tatcagagag tgagaggaac ttgtttattg cagcttataa tggttacaaa taaagcaata      9251
gcatcacaaa tttcacaaat aaagcatttt tttcactgca ttctagttgt ggtttgtcca      9311
aactcatcaa tgtatcttat catgtctggc tctagctatc ccgcccctaa ctccgcccag      9371
ttccgcccat tctccgcccc atggctgact aatttttttt atttatgcag aggccgaggc      9431
cgcctcggcc tctgagctat tccagaagta gtgaggaggc tttttttggag gcctaggctt      9491 ttgcgtcgag acgtacccaa ttcgccctat agtgagtcgt attacgcgcg ctcactggcc      9551
gtcgttttac aacgtcgtga ctgggaaaac cctggcgtta cccaacttaa tcgccttgca      9611
gcacatcccc ctttcgccag ctggcgtaat agcgaagagg cccgcaccga tcgcccttcc      9671
caacagttgc gcagcctgaa tggcgaatgg cgcgacgcgc cctgtagcgg cgcattaagc      9731
gcggcgggtg tggtggttac gcgcagcgtg accgctacac ttgccagcgc cctagcgccc      9791
gctcctttcg ctttcttccc ttcctttctc gccacgttcg ccggctttcc ccgtcaagct      9851
ctaaatcggg ggctcccttt agggttccga tttagtgctt tacggcacct cgaccccaaa      9911
aaacttgatt agggtgatgg ttcacgtagt gggccatcgc cctgatagac ggtttttcgc      9971
cctttgacgt tggagtccac gttctttaat agtggactct tgttccaaac tggaacaaca     10031 ctcaaccccta tctcggtcta ttcttttgat ttataaggga ttttgccgat ttcggcctat     10091
tggttaaaaa atgagctgat ttaacaaaaa tttaacgcga attttaacaa aatattaacg     10151
```

```
tttacaattt cccaggtggc acttttcggg gaaatgtgcg cggaacccct atttgtttat   10211
ttttctaaat acattcaaat atgtatccgc tcatgagaca ataaccctga taaatgcttc   10271
aataatattg aaaaaggaag agtatgagta ttcaacattt ccgtgtcgcc cttattccct   10331
tttttgcggc attttgcctt cctgtttttg ctcacccaga aacgctggtg aaagtaaaag   10391
atgctgaaga tcagttgggt gcacgagtgg gttacatcga actggatctc aacagcggta   10451
agatccttga gagtttttcgc cccgaagaac gttttccaat gatgagcact tttaaagttc   10511
tgctatgtgg cgcggtatta tcccgtattg acgccgggca agagcaactc ggtcgccgca   10571
tacactattc tcagaatgac ttggttg                                      10598
```

<210> SEQ ID NO 23
<211> LENGTH: 540
<212> TYPE: PRT
<213> ORGANISM: Artificial Sequence
<220> FEATURE:
<223> OTHER INFORMATION: [CDS]:4559..6181 from SEQ ID NO 22

<400> SEQUENCE: 23

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
```

-continued

```
              275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Ser Gly Gly Gly
                325                 330                 335

Gly Ser Gly Gly Gly Gly Ser Arg Asn Leu Pro Val Ala Thr Pro Asp
                340                 345                 350

Pro Gly Met Phe Pro Cys Leu His His Ser Gln Asn Leu Leu Arg Ala
                355                 360                 365

Val Ser Asn Met Leu Gln Lys Ala Arg Gln Thr Leu Glu Phe Tyr Pro
    370                 375                 380

Cys Thr Ser Glu Glu Ile Asp His Glu Asp Ile Thr Lys Asp Lys Thr
385                 390                 395                 400

Ser Thr Val Glu Ala Cys Leu Pro Leu Glu Leu Thr Lys Asn Glu Ser
                405                 410                 415

Cys Leu Asn Ser Arg Glu Thr Ser Phe Ile Thr Asn Gly Ser Cys Leu
                420                 425                 430

Ala Ser Arg Lys Thr Ser Phe Met Met Ala Leu Cys Leu Ser Ser Ile
                435                 440                 445

Tyr Glu Asp Leu Lys Met Tyr Gln Val Glu Phe Lys Thr Met Asn Ala
    450                 455                 460

Lys Leu Leu Met Asp Pro Lys Arg Gln Ile Phe Leu Asp Gln Asn Met
465                 470                 475                 480

Leu Ala Val Ile Asp Glu Leu Met Gln Ala Leu Asn Phe Asn Ser Glu
                485                 490                 495

Thr Val Pro Gln Lys Ser Ser Leu Glu Glu Pro Asp Phe Tyr Lys Thr
                500                 505                 510

Lys Ile Lys Leu Cys Ile Leu Leu His Ala Phe Arg Ile Arg Ala Val
                515                 520                 525

Thr Ile Asp Arg Val Met Ser Tyr Leu Asn Ala Ser
    530                 535                 540
```

```
<210> SEQ ID NO 24
<211> LENGTH: 9476
<212> TYPE: DNA
<213> ORGANISM: Artificial Sequence
<220> FEATURE:
<223> OTHER INFORMATION: pCCL.PPT.NFN:Benhsyn.EGFP.PGK.CAR.wPRE
<220> FEATURE:
<221> NAME/KEY: misc_signal
<222> LOCATION: 2683..2808
<223> OTHER INFORMATION: /note="HIV-1 psi packaging signal of human
      immunodeficiency virus type 1"
<220> FEATURE:
<221> NAME/KEY: misc_feature
<222> LOCATION: 3301..3534
<223> OTHER INFORMATION: /note="RRE: Rev response element (RRE) of HIV-1
      allows for Rev-dependent mRNA export from the nucleus to the
      cytoplasm"
<220> FEATURE:
<221> NAME/KEY: misc_feature
<222> LOCATION: 4030..4147
<223> OTHER INFORMATION: /note="cPPT/CTS: central polypurine tract and
      central termination sequence of HIV-1"
<220> FEATURE:
<221> NAME/KEY: promoter
<222> LOCATION: 4172..4275
<223> OTHER INFORMATION: /function="NFN:Benhsyn"
<220> FEATURE:
<221> NAME/KEY: misc_feature
```

-continued

```
<222> LOCATION: 4284..4338
<223> OTHER INFORMATION: /note="promoter section enhsyn"
<220> FEATURE:
<221> NAME/KEY: CDS
<222> LOCATION: 4351..5070
<223> OTHER INFORMATION: /gene="eGFP"
      /transl_table=1
<220> FEATURE:
<221> NAME/KEY: gene
<222> LOCATION: 5626..7080
<223> OTHER INFORMATION: /gene="CAR"
      /n=any nucleotide
<220> FEATURE:
<221> NAME/KEY: misc_feature
<222> LOCATION: 7107..7695
<223> OTHER INFORMATION: /note="WPRE: woodchuck hepatitis virus
      posttranscriptional regulatory element"

<400> SEQUENCE: 24
agtactcacc agtcacagaa aagcatctta cggatggcat gacagtaaga gaattatgca        60
gtgctgccat aaccatgagt gataacactg cggccaactt acttctgaca acgatcggag       120
gaccgaagga gctaaccgct tttttgcaca acatgggggga tcatgtaact cgccttgatc       180
gttgggaacc ggagctgaat gaagccatac caaacgacga gcgtgacacc acgatgcctg       240
tagcaatggc aacaacgttg cgcaaactat taactggcga actacttact ctagcttccc       300
ggcaacaatt aatagactgg atggaggcgg ataaagttgc aggaccactt ctgcgctcgg       360
cccttccggc tggctggttt attgctgata aatctggagc cggtgagcgt gggtctcgcg       420
gtatcattgc agcactgggg ccagatggta gccctcccg tatcgtagtt atctacacga       480
cggggagtca ggcaactatg gatgaacgaa atagacagat cgctgagata ggtgcctcac       540
tgattaagca ttggtaactg tcagaccaag tttactcata tatactttag attgatttaa       600
aacttcattt ttaatttaaa aggatctagg tgaagatcct ttttgataat ctcatgacca       660
aaatccctta acgtgagttt tcgttccact gagcgtcaga ccccgtagaa aagatcaaag       720
gatcttcttg agatcctttt tttctgcgcg taatctgctg cttgcaaaca aaaaaaccac       780
cgctaccagc ggtggtttgt ttgccggatc aagagctacc aactcttttt ccgaaggtaa       840
ctggcttcag cagagcgcag ataccaaata ctgttcttct agtgtagccg tagttaggcc       900
accacttcaa gaactctgta gcaccgccta cataccttcgc tctgctaatc ctgttaccag       960
tggctgctgc cagtggcgat aagtcgtgtc ttaccgggtt ggactcaaga cgatagttac      1020
cggataaggc gcagcggtcg ggctgaacgg ggggttcgtg cacacagccc agcttggagc      1080
gaacgaccta caccgaactg agatacctac agcgtgagct atgagaaagc gccacgcttc      1140
ccgaagggag aaaggcggac aggtatccgg taagcggcag ggtcggaaca ggagagcgca      1200
cgagggagct ccaggggga aacgcctggt atctttatag tcctgtcggg tttcgccacc      1260
tctgacttga gcgtcgattt ttgtgatgct cgtcagggg gcggagccta tggaaaaacg      1320
ccagcaacgc ggcctttttta cggttcctgg cctttgctg gccttttgct cacatgttct      1380
ttcctgcgtt atcccctgat tctgtggata accgtattac cgcctttgag tgagctgata      1440
ccgctcgccg cagccgaacg accgagcgca gcgagtcagt gagcgaggaa gcggaagagc      1500
gcccaatacg caaaccgcct ctccccgcgc gttggccgat tcattaatgc agctggcacg      1560
acaggtttcc cgactggaaa gcgggcagtg agcgcaacgc aattaatgtg agttagctca      1620
ctcattaggc accccaggct ttacacttta tgcttccggc tcgtatgttg tgtggaattg      1680
tgagcggata acaatttcac acaggaaaca gctatgacca tgattacgcc aagcgcgcaa      1740
ttaaccctca ctaaagggaa caaaagctgg agctgcaagc ttggccattg catacgttgt      1800
```

```
atccatatca taatatgtac atttatattg gctcatgtcc aacattaccg ccatgttgac    1860
attgattatt gactagttat taatagtaat caattacggg gtcattagtt catagcccat    1920
atatggagtt ccgcgttaca taacttacgg taaatggccc gcctggctga ccgcccaacg    1980
accccgcccc attgacgtca ataatgacgt atgttcccat agtaacgcca atagggactt    2040
tccattgacg tcaatgggtg gagtatttac ggtaaactgc ccacttggca gtacatcaag    2100
tgtatcatat gccaagtacg cccctattg acgtcaatga cggtaaatgg cccgcctggc    2160
attatgccca gtacatgacc ttatgggact ttcctacttg gcagtacatc tacgtattag    2220
tcatcgctat taccatggtg atgcggtttt ggcagtacat caatgggcgt ggatagcggt    2280
ttgactcacg gggatttcca agtctccacc ccattgacgt caatgggagt ttgttttggc    2340
accaaaatca acgggacttt ccaaaatgtc gtaacaactc cgccccattg acgcaaatgg    2400
gcggtaggcg tgtacggtgg gaggtctata taagcagagc tcgtttagtg aaccggggtc    2460
tctctggtta gaccagatct gagcctggga gctctctggc taactaggga acccactgct    2520
taagcctcaa taaagcttgc cttgagtgct tcaagtagtg tgtgcccgtc tgttgtgtga    2580
ctctggtaac tagagatccc tcagacccct ttagtcagtg tggaaaatct ctagcagtgg    2640
cgcccgaaca gggacttgaa agcgaaaggg aaaccagagg agctctctcg acgcaggact    2700
cggcttgctg aagcgcgcac ggcaagaggc gaggggcggc gactggtgag tacgccaaaa    2760
attttgacta gcggaggcta gaaggagaga gatgggtgcg agagcgtcag tattaagcgg    2820
gggagaatta gatcgcgatg ggaaaaaatt cggttaaggc caggggaaa gaaaaaatat     2880 aaattaaaac atatagtatg ggcaagcagg gagctagaac gattcgcagt taatcctggc    2940
ctgttagaaa catcagaagg ctgtagacaa atactgggac agctacaacc atcccttcag    3000
acaggatcag aagaacttag atcattatat aatacagtag caaccctcta ttgtgtgcat    3060
caaaggatag agataaaaga caccaaggaa gctttagaca agatagagga agagcaaaac    3120
aaaagtaaga ccaccgcaca gcaagcggcc gctgatcttc agacctggag gaggagatat    3180
gagggacaat tggagaagtg aattatataa atataaagta gtaaaaattg aaccattagg    3240
agtagcaccc accaaggcaa agagaagagt ggtgcagaga gaaaaaagag cagtgggaat    3300
aggagctttg ttccttgggt tcttgggagc agcaggaagc actatgggcg cagcctcaat    3360
gacgctgacg gtacaggcca gacaattatt gtctggtata gtgcagcagc agaacaattt    3420
gctgagggct attgaggcgc aacagcatct gttgcaactc acagtctggg gcatcaagca    3480
gctccaggca agaatcctgg ctgtggaaag atacctaaag gatcaacagc tcctggggat    3540
ttggggttgc tctggaaaac tcatttgcac cactgctgtg ccttggaatg ctagttggag    3600
taataaatct ctggaacaga tttggaatca cacgacctgg atggagtggg acagagaaat    3660
taacaattac acaagcttaa tacactcctt aattgaagaa tcgcaaaacc agcaagaaaa    3720
gaatgaacaa gaattattgg aattagataa atggcaagt ttgtggaatt ggtttaacat     3780
aacaaattgg ctgtggtata taaaattatt cataatgata gtaggaggct tggtaggttt    3840
aagaatagtt tttgctgtac tttctatagt gaatagagtt aggcagggat attcaccatt    3900
atcgtttcag acccacctcc caaccccgag gggacccgac aggcccgaag gaatagaaga    3960
agaaggtgga gagagagaca gagacagatc cattcgatta gtgaacggat ctcgacggta    4020
tcggttaact tttaaaagaa aaggggggat tggggggtac agtgcagggg aaagaatagt    4080
agacataata gcaacagaca tacaaactaa agaattacaa aaacaaatta caaaaattca    4140
```

```
aaattttatc gatcacgaga ctagcctcga ggggaatttc cggggacttt ccgggaattt    4200
ccggggactt tccgggaatt tccgggaatt tccggggact ttccgggaat ttccggggac    4260
tttccgggaa tttccctgca ggagactcta gagggtatat aatggtttaa acttaagctt    4320
ggtaccgggc ccccgaagac gcgtgccacc atg gtg agc aag ggc gag gag ctg    4374
                                    Met Val Ser Lys Gly Glu Glu Leu
                                    1               5 ttc acc ggg gtg gtg ccc atc ctg gtc gag ctg gac ggc gac gta aac    4422
Phe Thr Gly Val Val Pro Ile Leu Val Glu Leu Asp Gly Asp Val Asn
            10              15                  20 ggc cac aag ttc agc gtg tcc ggc gag ggc gag ggc gat gcc acc tac    4470
Gly His Lys Phe Ser Val Ser Gly Glu Gly Glu Gly Asp Ala Thr Tyr
25              30                  35                  40 ggc aag ctg acc ctg aag ttc atc tgc acc acc ggc aag ctg ccc gtg    4518
Gly Lys Leu Thr Leu Lys Phe Ile Cys Thr Thr Gly Lys Leu Pro Val
                45                  50                  55 ccc tgg ccc acc ctc gtg acc acc ctg acc tac ggc gtg cag tgc ttc    4566
Pro Trp Pro Thr Leu Val Thr Thr Leu Thr Tyr Gly Val Gln Cys Phe
            60                  65                  70 agc cgc tac ccc gac cac atg aag cag cac gac ttc ttc aag tcc gcc    4614
Ser Arg Tyr Pro Asp His Met Lys Gln His Asp Phe Phe Lys Ser Ala
            75                  80                  85 atg ccc gaa ggc tac gtc cag gag cgc acc atc ttc ttc aag gac gac    4662
Met Pro Glu Gly Tyr Val Gln Glu Arg Thr Ile Phe Phe Lys Asp Asp
        90                  95                  100 ggc aac tac aag acc cgc gcc gag gtg aag ttc gag ggc gac acc ctg    4710
Gly Asn Tyr Lys Thr Arg Ala Glu Val Lys Phe Glu Gly Asp Thr Leu
105                 110                 115                 120 gtg aac cgc atc gag ctg aag ggc atc gac ttc aag gag gac ggc aac    4758
Val Asn Arg Ile Glu Leu Lys Gly Ile Asp Phe Lys Glu Asp Gly Asn
                125                 130                 135 atc ctg ggg cac aag ctg gag tac aac tac aac agc cac aac gtc tat    4806
Ile Leu Gly His Lys Leu Glu Tyr Asn Tyr Asn Ser His Asn Val Tyr
            140                 145                 150 atc atg gcc gac aag cag aag aac ggc atc aag gtg aac ttc aag atc    4854
Ile Met Ala Asp Lys Gln Lys Asn Gly Ile Lys Val Asn Phe Lys Ile
            155                 160                 165 cgc cac aac atc gag gac ggc agc gtg cag ctc gcc gac cac tac cag    4902
Arg His Asn Ile Glu Asp Gly Ser Val Gln Leu Ala Asp His Tyr Gln
        170                 175                 180 cag aac acc ccc atc ggc gac ggc ccc gtg ctg ctg ccc gac aac cac    4950
Gln Asn Thr Pro Ile Gly Asp Gly Pro Val Leu Leu Pro Asp Asn His
185                 190                 195                 200 tac ctg agc acc cag tcc gcc ctg agc aaa gac ccc aac gag aag cgc    4998
Tyr Leu Ser Thr Gln Ser Ala Leu Ser Lys Asp Pro Asn Glu Lys Arg
                205                 210                 215 gat cac atg gtc ctg ctg gag ttc gtg acc gcc gcc ggg atc act ctc    5046
Asp His Met Val Leu Leu Glu Phe Val Thr Ala Ala Gly Ile Thr Leu
                220                 225                 230 ggc atg gac gag ctg tac aag taa tcgaattccc acggggttgg ggttgcgcct    5100
Gly Met Asp Glu Leu Tyr Lys
                235 tttccaaggc agccctgggt ttgcgcaggg acgcggctgc tctgggcgtg gttccgggaa    5160 acgcagcggc gccgaccctg ggtctcgcac attcttcacg tccgttcgca gcgtcacccg    5220 gatcttcgcc gctaccttg tgggcccccc ggcgacgctt cctgctccgc ccctaagtcg    5280 ggaaggttcc ttgcggttcg cggcgtgccg gacgtgacaa acggaagccg cacgtctcac    5340 tagtaccctc gcagacggac agcgccaggg agcaatggca gcgcgccgac cgcgatgggc    5400
```

```
tgtggccaat agcggctgct cagcggggcg cgccgagagc agcggccggg aagggcggt   5460 gcgggaggcg gggtgtgggg cggtagtgtg ggccctgttc ctgcccgcgc ggtgttccgc   5520
attctgcaag cctccggagc gcacgtcggc agtcggctcc ctcgttgacc gaatcaccga   5580
cctctctccc caggggatc caccggtcac gtggctagcg ccaccnnnnn nnnnnnnnnn   5640
nnnnnnnnnn nnnnnnnnnn nnnnnnnnnn nnnnnnnnnn nnnnnnnnnn nnnnnnnnnn   5700
nnnnnnnnnn nnnnnnnnnn nnnnnnnnnn nnnnnnnnnn nnnnnnnnnn nnnnnnnnnn   5760
nnnnnnnnnn nnnnnnnnnn nnnnnnnnnn nnnnnnnnnn nnnnnnnnnn nnnnnnnnnn   5820
nnnnnnnnnn nnnnnnnnnn nnnnnnnnnn nnnnnnnnnn nnnnnnnnnn nnnnnnnnnn   5880
nnnnnnnnnn nnnnnnnnnn nnnnnnnnnn nnnnnnnnnn nnnnnnnnnn nnnnnnnnnn   5940
nnnnnnnnnn nnnnnnnnnn nnnnnnnnnn nnnnnnnnnn nnnnnnnnnn nnnnnnnnnn   6000
nnnnnnnnnn nnnnnnnnnn nnnnnnnnnn nnnnnnnnnn nnnnnnnnnn nnnnnnnnnn   6060
nnnnnnnnnn nnnnnnnnnn nnnnnnnnnn nnnnnnnnnn nnnnnnnnnn nnnnnnnnnn   6120
nnnnnnnnnn nnnnnnnnnn nnnnnnnnnn nnnnnnnnnn nnnnnnnnnn nnnnnnnnnn   6180
nnnnnnnnnn nnnnnnnnnn nnnnnnnnnn nnnnnnnnnn nnnnnnnnnn nnnnnnnnnn   6240
nnnnnnnnnn nnnnnnnnnn nnnnnnnnnn nnnnnnnnnn nnnnnnnnnn nnnnnnnnnn   6300
nnnnnnnnnn nnnnnnnnnn nnnnnnnnnn nnnnnnnnnn nnnnnnnnnn nnnnnnnnnn   6360
nnnnnnnnnn nnnnnnnnnn nnnnnnnnnn nnnnnnnnnn nnnnnnnnnn nnnnnnnnnn   6420
nnnnnnnnnn nnnnnnnnnn nnnnnnnnnn nnnnnnnnnn nnnnnnnnnn nnnnnnnnnn   6480
nnnnnnnnnn nnnnnnnnnn nnnnnnnnnn nnnnnnnnnn nnnnnnnnnn nnnnnnnnnn   6540
nnnnnnnnnn nnnnnnnnnn nnnnnnnnnn nnnnnnnnnn nnnnnnnnnn nnnnnnnnnn   6600
nnnnnnnnnn nnnnnnnnnn nnnnnnnnnn nnnnnnnnnn nnnnnnnnnn nnnnnnnnnn   6660
nnnnnnnnnn nnnnnnnnnn nnnnnnnnnn nnnnnnnnnn nnnnnnnnnn nnnnnnnnnn   6720
nnnnnnnnnn nnnnnnnnnn nnnnnnnnnn nnnnnnnnnn nnnnnnnnnn nnnnnnnnnn   6780
nnnnnnnnnn nnnnnnnnnn nnnnnnnnnn nnnnnnnnnn nnnnnnnnnn nnnnnnnnnn   6840
nnnnnnnnnn nnnnnnnnnn nnnnnnnnnn nnnnnnnnnn nnnnnnnnnn nnnnnnnnnn   6900
nnnnnnnnnn nnnnnnnnnn nnnnnnnnnn nnnnnnnnnn nnnnnnnnnn nnnnnnnnnn   6960
nnnnnnnnnn nnnnnnnnnn nnnnnnnnnn nnnnnnnnnn nnnnnnnnnn nnnnnnnnnn   7020
nnnnnnnnnn nnnnnnnnnn nnnnnnnnnn nnnnnnnnnn nnnnnnnnnn nnnnnnnnnn   7080
taggatccgc cggcggccgc gtcgacaatc aacctctgga ttacaaaatt tgtgaaagat   7140
tgactggtat tcttaactat gttgctcctt ttacgctatg tggatacgct gctttaatgc   7200
ctttgtatca tgctattgct tcccgtatgg ctttcatttt ctcctccttg tataaatcct   7260
ggttgctgtc tctttatgag gagttgtggc ccgttgtcag gcaacgtggc gtggtgtgca   7320
ctgtgtttgc tgacgcaacc cccactggtt ggggcattgc caccacctgt cagctccttt   7380
ccgggacttt cgctttcccc ctccctattg ccacggcgga actcatcgcc gcctgccttg   7440
cccgctgctg gacaggggct cggctgttgg gcactgacaa ttccgtggtg ttgtcggga   7500 agctgacgtc ctttccatgg ctgctcgcct gtgttgccac ctggattctg cgcgggacgt   7560
ccttctgcta cgtcccttcg gccctcaatc cagcggacct tccttcccgc ggcctgctgc   7620
cggctctgcg gcctcttccg cgtcttcgcc ttcgccctca gacgagtcgg atctcccttt   7680
gggccgcctc cccgcctgga attcgagctc ggtacctttta agaccaatga cttacaaggc   7740
```

-continued

```
agctgtagat cttagccact tttaaaaga aaagggggga ctggaagggc taattcactc      7800
ccaacgaaga caagatctgc tttttgcttg tactgggtct ctctggttag accagatctg      7860
agcctgggag ctctctggct aactagggaa cccactgctt aagcctcaat aaagcttgcc      7920
ttgagtgctt caagtagtgt gtgcccgtct gttgtgtgac tctggtaact agagatccct      7980
cagacccttt tagtcagtgt ggaaaatctc tagcagtagt agttcatgtc atcttattat      8040
tcagtattta aacttgcaa agaaatgaat atcagagagt gagaggaact tgtttattgc      8100
agcttataat ggttacaaat aaagcaatag catcacaaat ttcacaaata aagcattttt      8160
ttcactgcat tctagttgtg gtttgtccaa actcatcaat gtatcttatc atgtctggct      8220
ctagctatcc cgcccctaac tccgcccagt tccgcccatt ctccgcccca tggctgacta      8280
atttttttta tttatgcaga ggccgaggcc gcctcggcct ctgagctatt ccagaagtag      8340
tgaggaggct ttttttggagg cctaggcttt tgcgtcgaga cgtacccaat tcgccctata      8400
gtgagtcgta ttacgcgcgc tcactggccg tcgttttaca acgtcgtgac tgggaaaacc      8460
ctggcgttac ccaacttaat cgccttgcag cacatccccc tttcgccagc tggcgtaata      8520
gcgaagaggc ccgcaccgat cgcccttccc aacagttgcg cagcctgaat ggcgaatggc      8580
gcgacgcgcc ctgtagcggc gcattaagcg cggcgggtgt ggtggttacg cgcagcgtga      8640
ccgctacact tgccagcgcc ctagcgcccg ctcctttcgc tttcttccct tcctttctcg      8700
ccacgttcgc cggctttccc cgtcaagctc taaatcgggg gctccctta gggttccgat      8760 ttagtgcttt acggcacctc gaccccaaaa aacttgatta gggtgatggt tcacgtagtg      8820
ggccatcgcc ctgatagacg gttttttcgcc ctttgacgtt ggagtccacg ttctttaata      8880
gtggactctt gttccaaact ggaacaacac tcaaccctat ctcggtctat tcttttgatt      8940
tataagggat tttgccgatt tcggcctatt ggttaaaaaa tgagctgatt taacaaaaat      9000
ttaacgcgaa ttttaacaaa atattaacgt ttacaatttc ccaggtggca cttttcgggg      9060
aaatgtgcgc ggaacccta tttgtttatt tttctaaata cattcaaata tgtatccgct      9120
catgagacaa taaccctgat aaatgcttca ataatattga aaaggaaga gtatgagtat      9180 tcaacatttc cgtgtcgccc ttattccctt ttttgcggca ttttgccttc ctgttttgc       9240 tcacccagaa acgctggtga aagtaaaaga tgctgaagat cagttgggtg cacgagtggg      9300
ttacatcgaa ctggatctca acagcggtaa gatccttgag agttttcgcc ccgaagaacg      9360
ttttccaatg atgagcactt ttaaagttct gctatgtggc gcggtattat cccgtattga      9420
cgccgggcaa gagcaactcg gtcgccgcat acactattct cagaatgact tggttg         9476
```

```
<210> SEQ ID NO 25
<211> LENGTH: 239
<212> TYPE: PRT
<213> ORGANISM: Artificial Sequence
<220> FEATURE:
<223> OTHER INFORMATION: [CDS]:4351..5070 from SEQ ID NO 24

<400> SEQUENCE: 25

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60
```

```
Leu Thr Tyr Gly Val Gln Cys Phe Ser Arg Tyr Pro Asp His Met Lys
65              70              75              80

Gln His Asp Phe Phe Lys Ser Ala Met Pro Glu Gly Tyr Val Gln Glu
                85              90              95

Arg Thr Ile Phe Phe Lys Asp Asp Gly Asn Tyr Lys Thr Arg Ala Glu
            100             105             110

Val Lys Phe Glu Gly Asp Thr Leu Val Asn Arg Ile Glu Leu Lys Gly
        115             120             125

Ile Asp Phe Lys Glu Asp Gly Asn Ile Leu Gly His Lys Leu Glu Tyr
    130             135             140

Asn Tyr Asn Ser His Asn Val Tyr Ile Met Ala Asp Lys Gln Lys Asn
145             150             155             160

Gly Ile Lys Val Asn Phe Lys Ile Arg His Asn Ile Glu Asp Gly Ser
            165             170             175

Val Gln Leu Ala Asp His Tyr Gln Gln Asn Thr Pro Ile Gly Asp Gly
        180             185             190

Pro Val Leu Leu Pro Asp Asn His Tyr Leu Ser Thr Gln Ser Ala Leu
    195             200             205

Ser Lys Asp Pro Asn Glu Lys Arg Asp His Met Val Leu Leu Glu Phe
    210             215             220

Val Thr Ala Ala Gly Ile Thr Leu Gly Met Asp Glu Leu Tyr Lys
225             230             235
```

```
<210> SEQ ID NO 26
<211> LENGTH: 7705
<212> TYPE: DNA
<213> ORGANISM: Artificial Sequence
<220> FEATURE:
<223> OTHER INFORMATION: pCAS.NFATenhsyn.EGFP.PGK.CAR.PRE SIN
<220> FEATURE:
<221> NAME/KEY: promoter
<222> LOCATION: 446..1116
<223> OTHER INFORMATION: /note="CMV promoter"
<220> FEATURE:
<221> NAME/KEY: misc_feature
<222> LOCATION: 1117..1137
<223> OTHER INFORMATION: /note="part of R element"
<220> FEATURE:
<221> NAME/KEY: misc_feature
<222> LOCATION: 1138..1217
<223> OTHER INFORMATION: /note="U5 element"
<220> FEATURE:
<221> NAME/KEY: misc_feature
<222> LOCATION: 1218..1236
<223> OTHER INFORMATION: /note="PBS"
<220> FEATURE:
<221> NAME/KEY: promoter
<222> LOCATION: 1504..1747
<223> OTHER INFORMATION: /note="promoter NFATenhsyn"
<220> FEATURE:
<221> NAME/KEY: CDS
<222> LOCATION: 1760..2479
<223> OTHER INFORMATION: /gene="eGFP"
        /transl_table=1
<220> FEATURE:
<221> NAME/KEY: gene
<222> LOCATION: 3035..4489
<223> OTHER INFORMATION: /note="CAR"
        /n=any nucleotide
<220> FEATURE:
<221> NAME/KEY: misc_feature
<222> LOCATION: 4732..5135
<223> OTHER INFORMATION: /note="WPRE: woodchuck hepatitis virus
        posttranscriptional regulatory element"
<220> FEATURE:
<221> NAME/KEY: misc_feature
<222> LOCATION: 5220..5273
```

-continued

```
<223> OTHER INFORMATION: /note="dU3 element"
<220> FEATURE:
<221> NAME/KEY: misc_feature
<222> LOCATION: 5274..5294
<223> OTHER INFORMATION: /note="part of R element"

<400> SEQUENCE: 26
```

```
ctgcctcgcg cgtttcggtg atgacggtga aaacctctga cacatgcagc tcccggagac      60
ggtcacagct tgtctgtaag cggatgccgg gagcagacaa gcccgtcagg gcgcgtcagc     120
gggtgttggc gggtgtcggg gcgcagccat gacccagtca cgtagcgata gttactatgc     180
ggcatcagag cagattgtac tgagagtgca ccatatgcgg tgtgaaatac cgcacagatg     240
cgtaaggaga aaataccgca tcaggcgcca ttcgccattc aggctgcgca actgttggga     300
agggcgatcg gtgcgggcct cttcgctatt acgccagctg cgaaagggg gatgtgctgc      360 aaggcgatta agttgggtaa cgccaggtt ttcccagtca cgacgttgta aaacgacggc      420
cagtgaatta gtactctagc ttaagccatt gcatacgttg tatccatatc ataatatgta     480
catttatatt ggctcatgtc caacattacc gccatgttga cattgattat tgactagtta     540
ttaatagtaa tcaattacgg ggtcattagt tcatagccca tatatggagt tccgcgttac     600
ataacttacg gtaaatggcc cgcctggctg accgcccaac gacccccgcc cattgacgtc     660
aataatgacg tatgttccca tagtaacgcc aatagggact ttccattgac gtcaatgggt     720
ggagtattta cggtaaactg cccacttggc agtacatcaa gtgtatcata tgccaagtac     780
gccccctatt gacgtcaatg acggtaaatg gcccgcctgg cattatgccc agtacatgac     840
cttatgggac tttcctactt ggcagtacat ctacgtatta gtcatcgcta ttaccatggt     900
gatgcggttt tggcagtaca tcaatgggcg tggatagcgg tttgactcac ggggatttcc     960
aagtctccac cccattgacg tcaatgggag tttgttttgg caccaaaatc aacgggactt    1020
tccaaaatgt cgtaacaact ccgccccatt gacgcaaatg ggcggtaggc gtgtacggtg    1080
ggaggtctat ataagcagag ctcgtttagt gaaccggcca tttgaccatt caccacattg    1140
gtgtgcacct gggttgatgg ccggaccgtt gattccctga cgactacgag cacctgcatg    1200
aagcagaagg cttcatttgg tgaccccgac gtgatagtta gggaatagtg tcggccaca     1260 gacggcgtgg cgatcctgtc tccatccgtc tcgtctatcg ggaggcgagt cgatgacccc    1320
tggtggaggg ggctgcggct tagggaggca gaagctgagt accgtcggag ggagctccag    1380
ggcccggagc gactgacccc tgccgagaac tcagagggtc gtcggaagac ggagagtgag    1440
cccgacgacc accccaggca cgtctttggt cggcctgcgg atcaagcagg cccgctcga     1500 gcgtggagga aaaactgttt catacagaag gcgtggagga aaaactgttt catacagaag    1560
gcgtggagga aaaactgttt catacagaag gcgtggagga aaaactgttt catacagaag    1620
gcgtggagga aaaactgttt catacagaag gcgtggagga aaaactgttt catacagaag    1680
gcgtctgcag gagactctag agggtatata atggtttaaa cttaagcttg gtaccgggcc    1740
cccgaagacg cgtgccacc atg gtg agc aag ggc gag gag ctg ttc acc ggg    1792
                     Met Val Ser Lys Gly Glu Glu Leu Phe Thr Gly
                      1               5                  10 gtg gtg ccc atc ctg gtc gag ctg gac ggc gac gta aac ggc cac aag    1840
Val Val Pro Ile Leu Val Glu Leu Asp Gly Asp Val Asn Gly His Lys
             15                  20                  25 ttc agc gtg tcc ggc gag ggc gag ggc gat gcc acc tac ggc aag ctg    1888
Phe Ser Val Ser Gly Glu Gly Glu Gly Asp Ala Thr Tyr Gly Lys Leu
         30                  35                  40 acc ctg aag ttc atc tgc acc acc ggc aag ctg ccc gtg ccc tgg ccc    1936
```

-continued

```
Thr Leu Lys Phe Ile Cys Thr Thr Gly Lys Leu Pro Val Pro Trp Pro
    45                  50                  55 acc ctc gtg acc acc ctg acc tac ggc gtg cag tgc ttc agc cgc tac        1984
Thr Leu Val Thr Thr Leu Thr Tyr Gly Val Gln Cys Phe Ser Arg Tyr
60                  65                  70                  75 ccc gac cac atg aag cag cac gac ttc ttc aag tcc gcc atg ccc gaa        2032
Pro Asp His Met Lys Gln His Asp Phe Phe Lys Ser Ala Met Pro Glu
                80                  85                  90 ggc tac gtc cag gag cgc acc atc ttc ttc aag gac gac ggc aac tac        2080
Gly Tyr Val Gln Glu Arg Thr Ile Phe Phe Lys Asp Asp Gly Asn Tyr
            95                  100                 105 aag acc cgc gcc gag gtg aag ttc gag ggc gac acc ctg gtg aac cgc        2128
Lys Thr Arg Ala Glu Val Lys Phe Glu Gly Asp Thr Leu Val Asn Arg
        110                 115                 120 atc gag ctg aag ggc atc gac ttc aag gag gac ggc aac atc ctg ggg        2176
Ile Glu Leu Lys Gly Ile Asp Phe Lys Glu Asp Gly Asn Ile Leu Gly
        125                 130                 135 cac aag ctg gag tac aac tac aac agc cac aac gtc tat atc atg gcc        2224
His Lys Leu Glu Tyr Asn Tyr Asn Ser His Asn Val Tyr Ile Met Ala
140                 145                 150                 155 gac aag cag aag aac ggc atc aag gtg aac ttc aag atc cgc cac aac        2272
Asp Lys Gln Lys Asn Gly Ile Lys Val Asn Phe Lys Ile Arg His Asn
                160                 165                 170 atc gag gac ggc agc gtg cag ctc gcc gac cac tac cag cag aac acc        2320
Ile Glu Asp Gly Ser Val Gln Leu Ala Asp His Tyr Gln Gln Asn Thr
            175                 180                 185 ccc atc ggc gac ggc ccc gtg ctg ctg ccc gac aac cac tac ctg agc        2368
Pro Ile Gly Asp Gly Pro Val Leu Leu Pro Asp Asn His Tyr Leu Ser
            190                 195                 200 acc cag tcc gcc ctg agc aaa gac ccc aac gag aag cgc gat cac atg        2416
Thr Gln Ser Ala Leu Ser Lys Asp Pro Asn Glu Lys Arg Asp His Met
        205                 210                 215 gtc ctg ctg gag ttc gtg acc gcc gcc ggg atc act ctc ggc atg gac        2464
Val Leu Leu Glu Phe Val Thr Ala Ala Gly Ile Thr Leu Gly Met Asp
220                 225                 230                 235 gag ctg tac aag taa tcgaattccc acggggttgg ggttgcgcct tttccaaggc        2519
Glu Leu Tyr Lys agccctgggt tgcgcaggg acgcggctgc tctgggcgtg gttccgggaa acgcagcggc         2579
gccgaccctg ggtctcgcac attcttcacg tccgttcgca gcgtcacccg gatcttcgcc         2639
gctacccttg tgggcccccc ggcgacgctt cctgctccgc ccctaagtcg ggaaggttcc         2699
ttgcggttcg cggcgtgccg gacgtgacaa acggaagccg cacgtctcac tagtaccctc         2759
gcagacggac agcgccaggg agcaatggca gcgcgccgac cgcgatgggc tgtggccaat         2819
agcggctgct cagcgggggcg cgccgagagc agcggccggg aagggggcggt gcgggaggcg        2879 gggtgtgggg cggtagtgtg ggccctgttc ctgcccgcgc ggtgttccgc attctgcaag         2939
cctccggagc gcacgtcggc agtcggctcc ctcgttgacc gaatcaccga cctctctccc         2999 caggggggatc caccggtcac gtggctagcg ccaccnnnnn nnnnnnnnnn nnnnnnnnnn         3059
nnnnnnnnnn nnnnnnnnnn nnnnnnnnnn nnnnnnnnnn nnnnnnnnnn nnnnnnnnnn         3119
nnnnnnnnnn nnnnnnnnnn nnnnnnnnnn nnnnnnnnnn nnnnnnnnnn nnnnnnnnnn         3179
nnnnnnnnnn nnnnnnnnnn nnnnnnnnnn nnnnnnnnnn nnnnnnnnnn nnnnnnnnnn         3239
nnnnnnnnnn nnnnnnnnnn nnnnnnnnnn nnnnnnnnnn nnnnnnnnnn nnnnnnnnnn         3299
nnnnnnnnnn nnnnnnnnnn nnnnnnnnnn nnnnnnnnnn nnnnnnnnnn nnnnnnnnnn         3359
nnnnnnnnnn nnnnnnnnnn nnnnnnnnnn nnnnnnnnnn nnnnnnnnnn nnnnnnnnnn         3419
```

-continued

```
nnnnnnnnnn nnnnnnnnnn nnnnnnnnnn nnnnnnnnnn nnnnnnnnnn nnnnnnnnnn    3479
nnnnnnnnnn nnnnnnnnnn nnnnnnnnnn nnnnnnnnnn nnnnnnnnnn nnnnnnnnnn    3539
nnnnnnnnnn nnnnnnnnnn nnnnnnnnnn nnnnnnnnnn nnnnnnnnnn nnnnnnnnnn    3599
nnnnnnnnnn nnnnnnnnnn nnnnnnnnnn nnnnnnnnnn nnnnnnnnnn nnnnnnnnnn    3659
nnnnnnnnnn nnnnnnnnnn nnnnnnnnnn nnnnnnnnnn nnnnnnnnnn nnnnnnnnnn    3719
nnnnnnnnnn nnnnnnnnnn nnnnnnnnnn nnnnnnnnnn nnnnnnnnnn nnnnnnnnnn    3779
nnnnnnnnnn nnnnnnnnnn nnnnnnnnnn nnnnnnnnnn nnnnnnnnnn nnnnnnnnnn    3839
nnnnnnnnnn nnnnnnnnnn nnnnnnnnnn nnnnnnnnnn nnnnnnnnnn nnnnnnnnnn    3899
nnnnnnnnnn nnnnnnnnnn nnnnnnnnnn nnnnnnnnnn nnnnnnnnnn nnnnnnnnnn    3959
nnnnnnnnnn nnnnnnnnnn nnnnnnnnnn nnnnnnnnnn nnnnnnnnnn nnnnnnnnnn    4019
nnnnnnnnnn nnnnnnnnnn nnnnnnnnnn nnnnnnnnnn nnnnnnnnnn nnnnnnnnnn    4079
nnnnnnnnnn nnnnnnnnnn nnnnnnnnnn nnnnnnnnnn nnnnnnnnnn nnnnnnnnnn    4139
nnnnnnnnnn nnnnnnnnnn nnnnnnnnnn nnnnnnnnnn nnnnnnnnnn nnnnnnnnnn    4199
nnnnnnnnnn nnnnnnnnnn nnnnnnnnnn nnnnnnnnnn nnnnnnnnnn nnnnnnnnnn    4259
nnnnnnnnnn nnnnnnnnnn nnnnnnnnnn nnnnnnnnnn nnnnnnnnnn nnnnnnnnnn    4319
nnnnnnnnnn nnnnnnnnnn nnnnnnnnnn nnnnnnnnnn nnnnnnnnnn nnnnnnnnnn    4379
nnnnnnnnnn nnnnnnnnnn nnnnnnnnnn nnnnnnnnnn nnnnnnnnnn nnnnnnnnnn    4439
nnnnnnnnnn nnnnnnnnnn nnnnnnnnnn nnnnnnnnnn nnnnnnnnnn taggatccgc    4499
cggcggccgc gtcgacggat cccccgggct gcaggaattc gagcatctta ccgccattta    4559
tacccatatt tgttctgttt ttcttgattt gggtatacat ttaaatgtta ataaaacaaa    4619
atggtggggc aatcatttac atttttaggg atatgtaatt actagttcag gtgtattgcc    4679
acaagacaaa catgttaaga aactttcccg ttatttacgc tctgttcctg ttaatcaacc    4739
tctggattac aaaatttgtg aaagattgac tgatattctt aactatgttg ctccttttac    4799
gctgtgtgga tatgctgctt taatgcctct gtatcatgct attgcttccc gtacggcttt    4859
cgttttctcc tccttgtata aatcctggtt gctgtctctt tatgaggagt tgtggcccgt    4919
tgtccgtcaa cgtggcgtgg tgtgctctgt gtttgctgac gcaacccca ctggctgggg    4979 cattgccacc acctgtcaac tcctttctgg gactttcgct ttcccctcc cgatcgccac    5039 ggcagaactc atcgccgcct gccttgcccg ctgctggaca ggggctaggt tgctgggcac    5099
tgataattcc gtggtgttgt cggggaagct gacgtccttt cgaattcgaa agcttttaaa    5159
tatcgatgcg atgtacgggc cagatatacg cgtatctgag gggactaggg tgtgtttagg    5219
cgaaaagcgg ggcttcggtt gtacgcggtt aggagtcccc ttaggatata gtagtttcgc    5279
ttttgcatag ggagggggaa atgtagtctt atgcaatact cttgtacgta gtgcctagct    5339
cgatacaata aacgccattt gaccattcac cacattggtg tgcacctggg ttgatggccg    5399
gaccgttgat tccctgacga ctacgagcac ctgcatgaag cagaaggctt cattctcgag    5459
agctttggcg taatcatggt catagctgtt tcctgtgtga aattgttatc cgctcacaat    5519
tccacacaac atacgagccg gaagcataaa gtgtaaagcc tggggtgcct aatgagtgag    5579
ctaactcaca ttaattgcgt tgcgctcact gcccgctttc cagtcgggaa acctgtcgtg    5639
ccagctgcat taatgaatcg gccaacgcgc ggggagaggc ggtttgcgta ttgggcgctc    5699
ttccgcttcc tcgctcactg actcgctgcg ctcggtcgtt cggctgcggc gagcggtatc    5759
```

-continued

```
agctcactca aaggcggtaa tacggttatc cacagaatca ggggataacg caggaaagaa    5819
catgtgagca aaaggccagc aaaaggccag gaaccgtaaa aaggccgcgt tgctggcgtt    5879
tttccatagg ctccgccccc ctgacgagca tcacaaaaat cgacgctcaa gtcagaggtg    5939
gcgaaacccg acaggactat aaagatacca ggcgtttccc cctggaagct ccctcgtgcg    5999
ctctcctgtt ccgaccctgc cgcttaccgg atacctgtcc gcctttctcc cttcgggaag    6059
cgtggcgctt tctcaatgct cacgctgtag gtatctcagt tcggtgtagg tcgttcgctc    6119
caagctgggc tgtgtgcacg aaccccccgt tcagcccgac cgctgcgcct tatccggtaa    6179
ctatcgtctt gagtccaacc cggtaagaca cgacttatcg ccactggcag cagccactgg    6239
taacaggatt agcagagcga ggtatgtagg cggtgctaca gagttcttga agtggtggcc    6299
taactacggc tacactagaa ggacagtatt tggtatctgc gctctgctga gccagttac    6359 cttcggaaaa agagttggta gctcttgatc cggcaaacaa accaccgctg gtagcggtgg    6419
tttttttgtt tgcaagcagc agattacgcg cagaaaaaaa ggatctcaag aagatccttt    6479
gatcttttct acggggtctg acgctcagtg gaacgaaaac tcacgttaag ggattttggt    6539
catgagatta tcaaaaagga tcttcaccta gatccttta aattaaaaat gaagttttaa    6599
atcaatctaa agtatatatg agtaaacttg gtctgacagt taccaatgct taatcagtga    6659
ggcacctatc tcagcgatct gtctatttcg ttcatccata gttgcctgac tccccgtcgt    6719
gtagataact acgatacggg agggcttacc atctggcccc agtgctgcaa tgataccgcg    6779
agacccacgc tcaccggctc cagatttatc agcaataaac cagccagccg gaagggccga    6839
gcgcagaagt ggtcctgcaa ctttatccgc ctccatccag tctattaatt gttgccggga    6899
agctagagta agtagttcgc cagttaatag tttgcgcaac gttgttgcca ttgctgctgg    6959
catcgtggtg tcacgctcgt cgtttggtat ggcttcattc agctccggtt cccaacgatc    7019
aaggcgagtt acatgatccc ccatgttgtg caaaaaagcg gttagctcct tcggtcctcc    7079
gatcgttgtc agaagtaagt tggccgcagt gttatcactc atggttatgg cagcactgca    7139
taattctctt actgtcatgc catccgtaag atgcttttct gtgactggtg agtactcaac    7199
caagtcattc tgagaatagt gtatgcggcg accgagttgc tcttgcccgg cgtcaatacg    7259
ggataatacc gcgccacata gcagaacttt aaaagtgctc atcattggaa aacgttcttc    7319
ggggcgaaaa ctctcaagga tcttaccgct gttgagatcc agttcgatgt aacccactcg    7379
tgcacccaac tgatcttcag catcttttac tttcaccagc gtttctgggt gagcaaaaac    7439
aggaaggcaa aatgccgcaa aaaagggaat aagggcgaca cggaaatgtt gaatactcat    7499
actcttcctt tttcaatatt attgaagcat ttatcagggt tattgtctca tgagcggata    7559
catatttgaa tgtatttaga aaataaaca aataggggtt ccgcgcacat ttccccgaaa    7619
agtgccacct gacgtctaag aaaccattat tatcatgaca ttaacctata aaaataggcg    7679
tatcacgagg ccctttcgtc ttcaag    7705
```

<210> SEQ ID NO 27
<211> LENGTH: 239
<212> TYPE: PRT
<213> ORGANISM: Artificial Sequence
<220> FEATURE:
<223> OTHER INFORMATION: [CDS]:1760..2479 from SEQ ID NO 26

<400> SEQUENCE: 27

```
Met Val Ser Lys Gly Glu Glu Leu Phe Thr Gly Val Val Pro Ile Leu
1               5                   10                  15
```

```
Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 28
<211> LENGTH: 7626
<212> TYPE: DNA
<213> ORGANISM: Artificial Sequence
<220> FEATURE:
<223> OTHER INFORMATION: pCAS.NFN:Benhsyn.EGFP.PGK.CAR.PRE SIN
<220> FEATURE:
<221> NAME/KEY: promoter
<222> LOCATION: 1496..1668
<223> OTHER INFORMATION: /note="promoter NFN:Benhsyn"
<220> FEATURE:
<221> NAME/KEY: CDS
<222> LOCATION: 1681..2400
<223> OTHER INFORMATION: /gene="eGFP"
     /transl_table=1
<220> FEATURE:
<221> NAME/KEY: gene
<222> LOCATION: 2956..4410
<223> OTHER INFORMATION: /gene="CAR"
     /n=any nucleotide
<220> FEATURE:
<221> NAME/KEY: misc_feature
<222> LOCATION: 4460..5062
<223> OTHER INFORMATION: /note="PRE"
<220> FEATURE:
<221> NAME/KEY: misc_feature
<222> LOCATION: 4653..5056
<223> OTHER INFORMATION: /note="WPRE: woodchuck hepatitis virus
     posttranscriptional regulatory element"

<400> SEQUENCE: 28
ctgcctcgcg cgtttcggtg atgacggtga aaacctctga cacatgcagc tcccggagac      60
ggtcacagct tgtctgtaag cggatgccgg gagcagacaa gcccgtcagg gcgcgtcagc     120

-continued

```
gggtgttggc gggtgtcggg gcgcagccat gacccagtca cgtagcgata gttactatgc      180
ggcatcagag cagattgtac tgagagtgca ccatatgcgg tgtgaaatac cgcacagatg      240
cgtaaggaga aaataccgca tcaggcgcca ttcgccattc aggctgcgca actgttggga      300
agggcgatcg gtgcgggcct cttcgctatt acgccagctg gcgaaagggg gatgtgctgc      360
aaggcgatta agttgggtaa cgccagggtt ttcccagtca cgacgttgta aaacgacggc      420
cagtgaatta gtactctagc ttaagccatt gcatacgttg tatccatatc ataatatgta      480
catttatatt ggctcatgtc caacattacc gccatgttga cattgattat tgactagtta      540
ttaatagtaa tcaattacgg ggtcattagt tcatagccca tatatggagt ccgcgttac      600 ataacttacg gtaaatggcc cgcctggctg accgcccaac gacccccgcc cattgacgtc      660
aataatgacg tatgttccca tagtaacgcc aatagggact ttccattgac gtcaatgggt      720
ggagtattta cggtaaactg cccacttggc agtacatcaa gtgtatcata tgccaagtac      780
gccccctatt gacgtcaatg acggtaaatg gcccgcctgg cattatgccc agtacatgac      840
cttatgggac tttcctactt ggcagtacat ctacgtatta gtcatcgcta ttaccatggt      900
gatgcggttt tggcagtaca tcaatgggcg tggatagcgg tttgactcac ggggatttcc      960
aagtctccac cccattgacg tcaatgggag tttgttttgg caccaaaatc aacgggactt     1020
tccaaaatgt cgtaacaact ccgccccatt gacgcaaatg gcggtaggc gtgtacggtg     1080 ggaggtctat ataagcagag ctcgtttagt gaaccggcca tttgaccatt caccacattg     1140
gtgtgcacct gggttgatgg ccggaccgtt gattccctga cgactacgag cacctgcatg     1200
aagcagaagg cttcatttgg tgaccccgac gtgatagtta gggaatagtg tcggccaca     1260 gacggcgtgg cgatcctgtc tccatccgtc tcgtctatcg ggaggcgagt cgatgaccc     1320 tggtggaggg ggctgcggct tagggaggca gaagctgagt accgtcggag ggagctccag     1380
ggcccggagc gactgacccc tgccgagaac tcagagggtc gtcggaagac ggagagtgag     1440
cccgacgacc accccaggca cgtctttggt cggcctgcgg atcaagcagg cccgctcga     1500 ggggaatttc cggggacttt ccgggaattt ccggggactt ccgggaatt ccgggaatt     1560 tccggggact ttccgggaat ttccggggac tttccgggaa tttccctgca ggagactcta     1620
gagggtatat aatggtttaa acttaagctt ggtaccgggc ccccgaagac gcgtgccacc     1680 atg gtg agc aag ggc gag gag ctg ttc acc ggg gtg gtg ccc atc ctg     1728
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc     1776
Val Glu Leu Asp Gly Asp Val Asn Gly His Lys Phe Ser Val Ser Gly
                20                  25                  30 gag ggc gag ggc gat gcc acc tac ggc aag ctg acc ctg aag ttc atc     1824
Glu Gly Glu Gly Asp Ala Thr Tyr Gly Lys Leu Thr Leu Lys Phe Ile
            35                  40                  45 tgc acc acc ggc aag ctg ccc gtg ccc tgg ccc acc ctc gtg acc acc     1872
Cys Thr Thr Gly Lys Leu Pro Val Pro Trp Pro Thr Leu Val Thr Thr
        50                  55                  60 ctg acc tac ggc gtg cag tgc ttc agc cgc tac ccc gac cac atg aag     1920
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     1968
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     2016
Arg Thr Ile Phe Phe Lys Asp Asp Gly Asn Tyr Lys Thr Arg Ala Glu
            100                 105                 110
```

-continued

```
gtg aag ttc gag ggc gac acc ctg gtg aac cgc atc gag ctg aag ggc    2064
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac    2112
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac    2160
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc    2208
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc    2256
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg    2304
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc    2352
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag taa    2400
Val Thr Ala Ala Gly Ile Thr Leu Gly Met Asp Glu Leu Tyr Lys
225                 230                 235 tcgaattccc acggggttgg ggttgcgcct tttccaaggc agccctgggt ttgcgcaggg    2460
acgcggctgc tctgggcgtg gttccgggaa acgcagcggc gccgaccctg ggtctcgcac    2520
attcttcacg tccgttcgca gcgtcacccg gatcttcgcc gctacccttg tgggcccccc    2580
ggcgacgctt cctgctccgc ccctaagtcg ggaaggttcc ttgcggttcg cggcgtgccg    2640
gacgtgacaa acggaagccg cacgtctcac tagtaccctc gcagacggac agcgccaggg    2700
agcaatggca gcgcgccgac cgcgatgggc tgtggccaat agcggctgct cagcggggcg    2760
cgccgagagc agcggccggg aaggggcggt gcgggaggcg gggtgtgggg cggtagtgtg    2820
ggccctgttc ctgcccgcgc ggtgttccgc attctgcaag cctccggagc gcacgtcggc    2880
agtcggctcc ctcgttgacc gaatcaccga cctctctccc caggggggatc caccggtcac    2940 gtggctagcg ccaccnnnnn nnnnnnnnnn nnnnnnnnnn nnnnnnnnnn nnnnnnnnnn    3000
nnnnnnnnnn nnnnnnnnnn nnnnnnnnnn nnnnnnnnnn nnnnnnnnnn nnnnnnnnnn    3060
nnnnnnnnnn nnnnnnnnnn nnnnnnnnnn nnnnnnnnnn nnnnnnnnnn nnnnnnnnnn    3120
nnnnnnnnnn nnnnnnnnnn nnnnnnnnnn nnnnnnnnnn nnnnnnnnnn nnnnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nnnnnnnnnn nnnnnnnnnn nnnnnnnnnn    3300
nnnnnnnnnn nnnnnnnnnn nnnnnnnnnn nnnnnnnnnn nnnnnnnnnn nnnnnnnnnn    3360
nnnnnnnnnn nnnnnnnnnn nnnnnnnnnn nnnnnnnnnn nnnnnnnnnn nnnnnnnnnn    3420
nnnnnnnnnn nnnnnnnnnn nnnnnnnnnn nnnnnnnnnn nnnnnnnnnn nnnnnnnnnn    3480
nnnnnnnnnn nnnnnnnnnn nnnnnnnnnn nnnnnnnnnn nnnnnnnnnn nnnnnnnnnn    3540
nnnnnnnnnn nnnnnnnnnn nnnnnnnnnn nnnnnnnnnn nnnnnnnnnn nnnnnnnnnn    3600
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn nnnnnnnnnn nnnnnnnnnn nnnnnnnnnn    3780
```

-continued

```
nnnnnnnnnn nnnnnnnnnn nnnnnnnnnn nnnnnnnnnn nnnnnnnnnn nnnnnnnnnn      3840
nnnnnnnnnn nnnnnnnnnn nnnnnnnnnn nnnnnnnnnn nnnnnnnnnn nnnnnnnnnn      3900
nnnnnnnnnn nnnnnnnnnn nnnnnnnnnn nnnnnnnnnn nnnnnnnnnn nnnnnnnnnn      3960
nnnnnnnnnn nnnnnnnnnn nnnnnnnnnn nnnnnnnnnn nnnnnnnnnn nnnnnnnnnn      4020
nnnnnnnnnn nnnnnnnnnn nnnnnnnnnn nnnnnnnnnn nnnnnnnnnn nnnnnnnnnn      4080
nnnnnnnnnn nnnnnnnnnn nnnnnnnnnn nnnnnnnnnn nnnnnnnnnn nnnnnnnnnn      4140
nnnnnnnnnn nnnnnnnnnn nnnnnnnnnn nnnnnnnnnn nnnnnnnnnn nnnnnnnnnn      4200
nnnnnnnnnn nnnnnnnnnn nnnnnnnnnn nnnnnnnnnn nnnnnnnnnn nnnnnnnnnn      4260
nnnnnnnnnn nnnnnnnnnn nnnnnnnnnn nnnnnnnnnn nnnnnnnnnn nnnnnnnnnn      4320
nnnnnnnnnn nnnnnnnnnn nnnnnnnnnn nnnnnnnnnn nnnnnnnnnn nnnnnnnnnn      4380
nnnnnnnnnn nnnnnnnnnn nnnnnnnnnn taggatccgc cggcggccgc gtcgacggat      4440
cccccgggct gcaggaattc gagcatctta ccgccattta tacccatatt tgttctgttt      4500
ttcttgattt gggtatacat ttaaatgtta ataaaacaaa atggtggggc aatcatttac      4560
atttttaggg atatgtaatt actagttcag gtgtattgcc acaagacaaa catgttaaga      4620
aactttcccg ttatttacgc tctgttcctg ttaatcaacc tctggattac aaaatttgtg      4680
aaagattgac tgatattctt aactatgttg ctccttttac gctgtgtgga tatgctgctt      4740
taatgcctct gtatcatgct attgcttccc gtacggcttt cgttttctcc tccttgtata      4800
aatcctggtt gctgtctctt tatgaggagt tgtggcccgt tgtccgtcaa cgtggcgtgg      4860
tgtgctctgt gtttgctgac gcaaccccca ctggctgggg cattgccacc acctgtcaac      4920
tcctttctgg gactttcgct ttccccctcc cgatcgccac ggcagaactc atcgccgcct      4980
gccttgcccg ctgctggaca ggggctaggt tgctgggcac tgataattcc gtggtgttgt      5040
cggggaagct gacgtccttt cgaattcgaa agcttttaaa tatcgatgcg atgtacgggc      5100
cagatatacg cgtatctgag gggactaggt tgtgtttagg cgaaaagcgg ggcttcggtt      5160
gtacgcggtt aggagtcccc ttaggatata gtagtttcgc ttttgcatag ggagggggaa      5220
atgtagtctt atgcaatact cttgtacgta gtgcctagct cgatacaata aacgccattt      5280
gaccattcac cacattggtg tgcacctggg ttgatggccg gaccgttgat tccctgacga      5340
ctacgagcac ctgcatgaag cagaaggctt cattctcgag agctttggcg taatcatggt      5400
catagctgtt tcctgtgtga aattgttatc cgctcacaat tccacacaac atacgagccg      5460
gaagcataaa gtgtaaagcc tggggtgcct aatgagtgag ctaactcaca ttaattgcgt      5520
tgcgctcact gcccgctttc cagtcgggaa acctgtcgtg ccagctgcat taatgaatcg      5580
gccaacgcgc ggggagaggc ggtttgcgta ttgggcgctc ttccgcttcc tcgctcactg      5640
actcgctgcg ctcggtcgtt cggctgcggc gagcggtatc agctcactca aaggcggtaa      5700
tacggttatc cacagaatca ggggataacg caggaaagaa catgtgagca aaaggccagc      5760
aaaaggccag gaaccgtaaa aaggccgcgt tgctggcgtt tttccatagg ctccgccccc      5820
ctgacgagca tcacaaaaat cgacgctcaa gtcagaggtg gcgaaacccg acaggactat      5880
aaagatacca ggcgtttccc cctggaagct ccctcgtgcg ctctcctgtt ccgaccctgc      5940
cgcttaccgg atacctgtcc gcctttctcc cttcgggaag cgtggcgctt tctcaatgct      6000
cacgctgtag gtatctcagt tcggtgtagg tcgttcgctc caagctgggc tgtgtgcacg      6060 aacccccgt tcagcccgac cgctgcgcct tatccggtaa ctatcgtctt gagtccaacc      6120
cggtaagaca cgacttatcg ccactggcag cagccactgg taacaggatt agcagagcga      6180
```

-continued

```
ggtatgtagg cggtgctaca gagttcttga agtggtggcc taactacggc tacactagaa    6240
ggacagtatt tggtatctgc gctctgctga agccagttac cttcggaaaa agagttggta    6300
gctcttgatc cggcaaacaa accaccgctg gtagcggtgg tttttttgtt tgcaagcagc    6360
agattacgcg cagaaaaaaa ggatctcaag aagatccttt gatcttttct acggggtctg    6420
acgctcagtg gaacgaaaac tcacgttaag ggattttggt catgagatta tcaaaaagga    6480
tcttcaccta gatccttta aattaaaaat gaagttttaa atcaatctaa agtatatatg    6540
agtaaacttg gtctgacagt taccaatgct taatcagtga ggcacctatc tcagcgatct    6600
gtctatttcg ttcatccata gttgcctgac tccccgtcgt gtagataact acgatacggg    6660
agggcttacc atctggcccc agtgctgcaa tgataccgcg agacccacgc tcaccggctc    6720
cagatttatc agcaataaac cagccagccg aagggccga gcgcagaagt ggtcctgcaa    6780
ctttatccgc ctccatccag tctattaatt gttgccggga gctagagta agtagttcgc    6840 cagttaatag tttgcgcaac gttgttgcca ttgctgctgg catcgtggtg tcacgctcgt    6900
cgtttggtat ggcttcattc agctccggtt cccaacgatc aaggcgagtt acatgatccc    6960
ccatgttgtg caaaaaagcg gttagctcct tcggtcctcc gatcgttgtc agaagtaagt    7020
tggccgcagt gttatcactc atggttatgg cagcactgca taattctctt actgtcatgc    7080
catccgtaag atgcttttct gtgactggtg agtactcaac caagtcattc tgagaatagt    7140
gtatgcggcg accgagttgc tcttgcccgg cgtcaatacg ggataatacc gcgccacata    7200
gcagaacttt aaaagtgctc atcattggaa aacgttcttc ggggcgaaaa ctctcaagga    7260
tcttaccgct gttgagatcc agttcgatgt aacccactcg tgcacccaac tgatcttcag    7320
catcttttac tttcaccagc gtttctgggt gagcaaaaac aggaaggcaa aatgccgcaa    7380
aaaagggaat aagggcgaca cggaaatgtt gaatactcat actcttcctt tttcaatatt    7440
attgaagcat ttatcagggt tattgtctca tgagcggata catatttgaa tgtatttaga    7500
aaaataaaca aataggggtt ccgcgcacat ttccccgaaa agtgccacct gacgtctaag    7560
aaaccattat tatcatgaca ttaacctata aaaataggcg tatcacgagg ccctttcgtc    7620
ttcaag                                                                7626
```

```
<210> SEQ ID NO 29
<211> LENGTH: 239
<212> TYPE: PRT
<213> ORGANISM: Artificial Sequence
<220> FEATURE:
<223> OTHER INFORMATION: [CDS]:1681..2400 from SEQ ID NO 28

<400> SEQUENCE: 29

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95
```

-continued

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235
```

```
<210> SEQ ID NO 30
<211> LENGTH: 239
<212> TYPE: PRT
<213> ORGANISM: Artificial Sequence
<220> FEATURE:
<223> OTHER INFORMATION: [CDS]:4430..5149 from SEQ ID NO 8

<400> SEQUENCE: 30
```

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
            50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220
```

-continued

```
Val Thr Ala Ala Gly Ile Thr Leu Gly Met Asp Glu Leu Tyr Lys
225                 230                 235
```

```
<210> SEQ ID NO 31
<211> LENGTH: 224
<212> TYPE: DNA
<213> ORGANISM: Artificial Sequence
<220> FEATURE:
<223> OTHER INFORMATION: NFN:BmIL2 promoter
<220> FEATURE:
<221> NAME/KEY: TATA_signal
<222> LOCATION: 151..157
<223> OTHER INFORMATION: /note="TATA box"

<400> SEQUENCE: 31
gggaatttcc ggggactttc cgggaatttc cggggacttt ccgggaattt ccgggaattt     60
ccggggactt tccgggaatt tccggggact ttccgggaat ttcccccggg acattttgac    120
acccccataa tattttccca gaattaacag tataaattgc atctcttgtt caagagttcc    180
ctatcactct ctttaatcac tactcacagt aacctcaact cctg                    224

<210> SEQ ID NO 32
<211> LENGTH: 9544
<212> TYPE: DNA
<213> ORGANISM: Artificial Sequence
<220> FEATURE:
<223> OTHER INFORMATION: pCCL.PPT.NFN:BmIL2.EGFP.PGK.CAR.WPRE
<220> FEATURE:
<221> NAME/KEY: misc_signal
<222> LOCATION: 2683..2808
<223> OTHER INFORMATION: /note="HIV-1 psi packaging signal of human
      immunodeficiency virus type 1"
<220> FEATURE:
<221> NAME/KEY: misc_feature
<222> LOCATION: 3301..3535
<223> OTHER INFORMATION: /note="RRE - Rev response element of HIV-1
      allows for Rev-dependent mRNA export from the nucleus to the
      cytoplasm"
<220> FEATURE:
<221> NAME/KEY: misc_feature
<222> LOCATION: 4030..4147
<223> OTHER INFORMATION: /note="cPPT/CTS: central polypurine tract and
      central termination sequence of HIV-1"
<220> FEATURE:
<221> NAME/KEY: promoter
<222> LOCATION: 4178..4281
<223> OTHER INFORMATION: /note="NFN:B"
<220> FEATURE:
<221> NAME/KEY: promoter
<222> LOCATION: 4178..4400
<223> OTHER INFORMATION: /note="NFN:BmIL2"
<220> FEATURE:
<221> NAME/KEY: misc_feature
<222> LOCATION: 4282..4400
<223> OTHER INFORMATION: /note="mIL2"
<220> FEATURE:
<221> NAME/KEY: CDS
<222> LOCATION: 4419..5138
<223> OTHER INFORMATION: /gene="eGFP"
      /transl_table=1
<220> FEATURE:
<221> NAME/KEY: misc_feature
<222> LOCATION: 5694..7148
<223> OTHER INFORMATION: /note="CAR"
<220> FEATURE:
<221> NAME/KEY: misc_feature
<222> LOCATION: 7163..7768
<223> OTHER INFORMATION: /note="PRE"
<220> FEATURE:
<221> NAME/KEY: misc_feature
<222> LOCATION: 7175..7763
<223> OTHER INFORMATION: /note="WPRE: woodchuck hepatitis virus
      posttranscriptional regulatory element"
```

-continued

```
<400> SEQUENCE: 32
agtactcacc agtcacagaa aagcatctta cggatggcat gacagtaaga gaattatgca      60
gtgctgccat aaccatgagt gataacactg cggccaactt acttctgaca acgatcggag     120
gaccgaagga gctaaccgct tttttgcaca acatggggga tcatgtaact cgccttgatc     180
gttgggaacc ggagctgaat gaagccatac caaacgacga gcgtgacacc acgatgcctg     240
tagcaatggc aacaacgttg cgcaaactat taactggcga actacttact ctagcttccc     300
ggcaacaatt aatagactgg atggaggcgg ataaagttgc aggaccactt ctgcgctcgg     360
cccttccggc tggctggttt attgctgata aatctggagc cggtgagcgt gggtctcgcg     420
gtatcattgc agcactgggg ccagatggta agccctcccg tatcgtagtt atctacacga     480
cggggagtca ggcaactatg gatgaacgaa atagacagat cgctgagata ggtgcctcac     540
tgattaagca ttggtaactg tcagaccaag tttactcata tatactttag attgatttaa     600
aacttcattt ttaatttaaa aggatctagg tgaagatcct ttttgataat ctcatgacca     660
aaatccctta acgtgagttt tcgttccact gagcgtcaga ccccgtagaa aagatcaaag     720
gatcttcttg agatcctttt tttctgcgcg taatctgctg cttgcaaaca aaaaaaccac     780
cgctaccagc ggtggtttgt ttgccggatc aagagctacc aactcttttt ccgaaggtaa     840
ctggcttcag cagagcgcag ataccaaata ctgttcttct agtgtagccg tagttaggcc     900
accacttcaa gaactctgta gcaccgccta catacctcgc tctgctaatc ctgttaccag     960
tggctgctgc cagtggcgat aagtcgtgtc ttaccgggtt ggactcaaga cgatagttac    1020
cggataaggc gcagcggtcg ggctgaacgg ggggttcgtg cacacagccc agcttggagc    1080
gaacgaccta caccgaactg agatacctac agcgtgagct atgagaaagc gccacgcttc    1140
ccgaagggag aaaggcggac aggtatccgg taagcggcag ggtcggaaca ggagagcgca    1200
cgagggagct tccaggggga aacgcctggt atctttatag tcctgtcggg tttcgccacc    1260
tctgacttga gcgtcgattt ttgtgatgct cgtcaggggg gcggagccta tggaaaaacg    1320
ccagcaacgc ggcctttttacggttcctgg ccttttgctg gccttttgct cacatgttct    1380
ttcctgcgtt atcccctgat tctgtggata accgtattac cgcctttgag tgagctgata    1440
ccgctcgccg cagccgaacg accgagcgca gcgagtcagt gagcgaggaa gcggaagagc    1500
gcccaatacg caaaccgcct ctccccgcgc gttggccgat tcattaatgc agctggcacg    1560
acaggtttcc cgactggaaa gcgggcagtg agcgcaacgc aattaatgtg agttagctca    1620
ctcattaggc accccaggct ttacacttta tgcttccggc tcgtatgttg tgtggaattg    1680
tgagcggata acaatttcac acaggaaaca gctatgacca tgattacgcc aagcgcgcaa    1740
ttaaccctca ctaaagggaa caaaagctgg agctgcaagc ttggccattg catacgttgt    1800
atccatatca taatatgtac atttatattg gctcatgtcc aacattaccg ccatgttgac    1860
attgattatt gactagttat taatagtaat caattacggg gtcattagtt catagcccat    1920
atatggagtt ccgcgttaca taacttacgg taaatggccc gcctggctga ccgcccaacg    1980
acccccgccc attgacgtca ataatgacgt atgttcccat agtaacgcca atagggactt    2040
tccattgacg tcaatgggtg gagtatttac ggtaaactgc ccacttggca gtacatcaag    2100
tgtatcatat gccaagtacg cccectattg acgtcaatga cggtaaatgg cccgcctggc    2160
attatgccca gtacatgacc ttatgggact ttcctacttg gcagtacatc tacgtattag    2220
tcatcgctat taccatggtg atgcggtttt ggcagtacat caatgggcgt ggatagcggt    2280
ttgactcacg gggatttcca agtctccacc ccattgacgt caatgggagt ttgttttggc    2340
```

-continued

```
accaaaatca acgggacttt ccaaaatgtc gtaacaactc cgccccattg acgcaaatgg     2400
gcggtaggcg tgtacggtgg gaggtctata taagcagagc tcgtttagtg aaccggggtc     2460
tctctggtta gaccagatct gagcctggga gctctctggc taactaggga acccactgct     2520
taagcctcaa taaagcttgc cttgagtgct tcaagtagtg tgtgcccgtc tgttgtgtga     2580
ctctggtaac tagagatccc tcagaccctt ttagtcagtg tggaaaatct ctagcagtgg     2640
cgcccgaaca gggacttgaa agcgaaaggg aaaccagagg agctctctcg acgcaggact     2700
cggcttgctg aagcgcgcac ggcaagaggc gaggggcggc gactggtgag tacgccaaaa     2760
attttgacta gcggaggcta gaaggagaga gatgggtgcg agagcgtcag tattaagcgg     2820
gggagaatta gatcgcgatg gaaaaaatt cggttaaggc cagggggaaa gaaaaaatat     2880
aaattaaaac atatagtatg ggcaagcagg gagctagaac gattcgcagt taatcctggc     2940
ctgttagaaa catcagaagg ctgtagacaa atactgggac agctacaacc atcccttcag     3000
acaggatcag aagaacttag atcattatat aatacagtag caaccctcta ttgtgtgcat     3060
caaaggatag agataaaaga caccaaggaa gctttagaca agatagagga agagcaaaac     3120
aaaagtaaga ccaccgcaca gcaagcggcc gctgatcttc agacctggag gaggagatat     3180
gagggacaat tggagaagtg aattatataa atataaagta gtaaaaattg aaccattagg     3240
agtagcaccc accaaggcaa agagaagagt ggtgcagaga gaaaaaagag cagtgggaat     3300
aggagctttg ttccttgggt tcttgggagc agcaggaagc actatgggcg cagcctcaat     3360
gacgctgacg gtacaggcca gacaattatt gtctggtata gtgcagcagc agaacaattt     3420
gctgagggct attgaggcgc aacagcatct gttgcaactc acagtctggg gcatcaagca     3480
gctccaggca agaatcctgg ctgtggaaag atacctaaag gatcaacagc tcctggggat     3540
ttggggttgc tctggaaaac tcatttgcac cactgctgtg ccttggaatg ctagttggag     3600
taataaatct ctggaacaga tttggaatca cacgacctgg atggagtggg acagagaaat     3660
taacaattac acaagcttaa tacactcctt aattgaagaa tcgcaaaacc agcaagaaaa     3720
gaatgaacaa gaattattgg aattagataa atgggcaagt ttgtggaatt ggtttaacat     3780
aacaaattgg ctgtggtata taaaattatt cataatgata gtaggaggct tggtaggttt     3840
aagaatagtt tttgctgtac tttctatagt gaatagagtt aggcagggat attcaccatt     3900
atcgtttcag acccacctcc caaccccgag gggacccgac aggcccgaag gaatagaaga     3960
agaaggtgga gagagagaca gagacagatc cattcgatta gtgaacggat ctcgacggta     4020
tcggttaact tttaaaagaa aaggggggat tggggggtac agtgcagggg aaagaatagt     4080
agacataata gcaacagaca tacaaactaa agaattacaa aaacaaatta caaaaattca     4140
aaattttatc gatcacgaga ctagcctcga cagcgctggg aatttccggg actttccgg     4200 gaatttccgg ggactttccg ggaatttccg ggaatttccg gggactttcc gggaatttcc     4260
ggggactttc cgggaatttc ccccgggaca ttttgacacc cccataatat ttttccagaa     4320
ttaacagtat aaattgcatc tcttgttcaa gagttcccta tcactctctt taatcactac     4380
tcacagtaac ctcaactcct ggatccacgc gtgccacc atg gtg agc aag ggc gag     4436
                                            Met Val Ser Lys Gly Glu
                                             1               5 gag ctg ttc acc ggg gtg gtg ccc atc ctg gtc gag ctg gac ggc gac     4484
Glu Leu Phe Thr Gly Val Val Pro Ile Leu Val Glu Leu Asp Gly Asp
            10              15              20 gta aac ggc cac aag ttc agc gtg tcc ggc gag ggc gag ggc gat gcc     4532
Val Asn Gly His Lys Phe Ser Val Ser Gly Glu Gly Glu Gly Asp Ala
```

-continued

```
              25                  30                  35 acc tac ggc aag ctg acc ctg aag ttc atc tgc acc acc ggc aag ctg       4580
Thr Tyr Gly Lys Leu Thr Leu Lys Phe Ile Cys Thr Thr Gly Lys Leu
    40                  45                  50 ccc gtg ccc tgg ccc acc ctc gtg acc acc ctg acc tac ggc gtg cag       4628
Pro Val Pro Trp Pro Thr Leu Val Thr Thr Leu Thr Tyr Gly Val Gln
55                  60                  65                  70 tgc ttc agc cgc tac ccc gac cac atg aag cag cac gac ttc ttc aag       4676
Cys Phe Ser Arg Tyr Pro Asp His Met Lys Gln His Asp Phe Phe Lys
                75                  80                  85 tcc gcc atg ccc gaa ggc tac gtc cag gag cgc acc atc ttc ttc aag       4724
Ser Ala Met Pro Glu Gly Tyr Val Gln Glu Arg Thr Ile Phe Phe Lys
            90                  95                  100 gac gac ggc aac tac aag acc cgc gcc gag gtg aag ttc gag ggc gac       4772
Asp Asp Gly Asn Tyr Lys Thr Arg Ala Glu Val Lys Phe Glu Gly Asp
        105                 110                 115 acc ctg gtg aac cgc atc gag ctg aag ggc atc gac ttc aag gag gac       4820
Thr Leu Val Asn Arg Ile Glu Leu Lys Gly Ile Asp Phe Lys Glu Asp
    120                 125                 130 ggc aac atc ctg ggg cac aag ctg gag tac aac tac aac agc cac aac       4868
Gly Asn Ile Leu Gly His Lys Leu Glu Tyr Asn Tyr Asn Ser His Asn
135                 140                 145                 150 gtc tat atc atg gcc gac aag cag aag aac ggc atc aag gtg aac ttc       4916
Val Tyr Ile Met Ala Asp Lys Gln Lys Asn Gly Ile Lys Val Asn Phe
                155                 160                 165 aag atc cgc cac aac atc gag gac ggc agc gtg cag ctc gcc gac cac       4964
Lys Ile Arg His Asn Ile Glu Asp Gly Ser Val Gln Leu Ala Asp His
            170                 175                 180 tac cag cag aac acc ccc atc ggc gac ggc ccc gtg ctg ctg ccc gac       5012
Tyr Gln Gln Asn Thr Pro Ile Gly Asp Gly Pro Val Leu Leu Pro Asp
        185                 190                 195 aac cac tac ctg agc acc cag tcc gcc ctg agc aaa gac ccc aac gag       5060
Asn His Tyr Leu Ser Thr Gln Ser Ala Leu Ser Lys Asp Pro Asn Glu
    200                 205                 210 aag cgc gat cac atg gtc ctg ctg gag ttc gtg acc gcc gcc ggg atc       5108
Lys Arg Asp His Met Val Leu Leu Glu Phe Val Thr Ala Ala Gly Ile
215                 220                 225                 230 act ctc ggc atg gac gag ctg tac aag taa tcgaattccc acggggttgg         5158
Thr Leu Gly Met Asp Glu Leu Tyr Lys
                235 ggttgcgcct tttccaaggc agccctgggt ttgcgcaggg acgcggctgc tctgggcgtg      5218 gttccgggaa acgcagcggc gccgaccctg ggtctcgcac attcttcacg tccgttcgca      5278 gcgtcacccg gatcttcgcc gctacccttg tgggcccccc ggcgacgctt cctgctccgc      5338 ccctaagtcg ggaaggttcc ttgcggttcg cggcgtgccg gacgtgacaa acggaagccg      5398 cacgtctcac tagtaccctc gcagacggac agcgccaggg agcaatggca gcgcgccgac      5458 cgcgatgggc tgtggccaat agcggctgct cagcggggcg cgccgagagc agcggccggg      5518 aaggggcggt gcgggaggcg gggtgtgggg cggtagtgtg ggccctgttc ctgcccgcgc      5578 ggtgttccgc attctgcaag cctccggagc gcacgtcggc agtcggctcc ctcgttgacc      5638 gaatcaccga cctctctccc caggggggatc caccggtcac gtggctagcg ccaccnnnnn      5698 nnnnnnnnnn nnnnnnnnnn nnnnnnnnnn nnnnnnnnnn nnnnnnnnnn nnnnnnnnnn      5758 nnnnnnnnnn nnnnnnnnnn nnnnnnnnnn nnnnnnnnnn nnnnnnnnnn nnnnnnnnnn      5818 nnnnnnnnnn nnnnnnnnnn nnnnnnnnnn nnnnnnnnnn nnnnnnnnnn nnnnnnnnnn      5878 nnnnnnnnnn nnnnnnnnnn nnnnnnnnnn nnnnnnnnnn nnnnnnnnnn nnnnnnnnnn      5938
```

```
nnnnnnnnnn nnnnnnnnnn nnnnnnnnnn nnnnnnnnnn nnnnnnnnnn nnnnnnnnnn    5998
nnnnnnnnnn nnnnnnnnnn nnnnnnnnnn nnnnnnnnnn nnnnnnnnnn nnnnnnnnnn    6058
nnnnnnnnnn nnnnnnnnnn nnnnnnnnnn nnnnnnnnnn nnnnnnnnnn nnnnnnnnnn    6118
nnnnnnnnnn nnnnnnnnnn nnnnnnnnnn nnnnnnnnnn nnnnnnnnnn nnnnnnnnnn    6178
nnnnnnnnnn nnnnnnnnnn nnnnnnnnnn nnnnnnnnnn nnnnnnnnnn nnnnnnnnnn    6238
nnnnnnnnnn nnnnnnnnnn nnnnnnnnnn nnnnnnnnnn nnnnnnnnnn nnnnnnnnnn    6298
nnnnnnnnnn nnnnnnnnnn nnnnnnnnnn nnnnnnnnnn nnnnnnnnnn nnnnnnnnnn    6358
nnnnnnnnnn nnnnnnnnnn nnnnnnnnnn nnnnnnnnnn nnnnnnnnnn nnnnnnnnnn    6418
nnnnnnnnnn nnnnnnnnnn nnnnnnnnnn nnnnnnnnnn nnnnnnnnnn nnnnnnnnnn    6478
nnnnnnnnnn nnnnnnnnnn nnnnnnnnnn nnnnnnnnnn nnnnnnnnnn nnnnnnnnnn    6538
nnnnnnnnnn nnnnnnnnnn nnnnnnnnnn nnnnnnnnnn nnnnnnnnnn nnnnnnnnnn    6598
nnnnnnnnnn nnnnnnnnnn nnnnnnnnnn nnnnnnnnnn nnnnnnnnnn nnnnnnnnnn    6658
nnnnnnnnnn nnnnnnnnnn nnnnnnnnnn nnnnnnnnnn nnnnnnnnnn nnnnnnnnnn    6718
nnnnnnnnnn nnnnnnnnnn nnnnnnnnnn nnnnnnnnnn nnnnnnnnnn nnnnnnnnnn    6778
nnnnnnnnnn nnnnnnnnnn nnnnnnnnnn nnnnnnnnnn nnnnnnnnnn nnnnnnnnnn    6838
nnnnnnnnnn nnnnnnnnnn nnnnnnnnnn nnnnnnnnnn nnnnnnnnnn nnnnnnnnnn    6898
nnnnnnnnnn nnnnnnnnnn nnnnnnnnnn nnnnnnnnnn nnnnnnnnnn nnnnnnnnnn    6958
nnnnnnnnnn nnnnnnnnnn nnnnnnnnnn nnnnnnnnnn nnnnnnnnnn nnnnnnnnnn    7018
nnnnnnnnnn nnnnnnnnnn nnnnnnnnnn nnnnnnnnnn nnnnnnnnnn nnnnnnnnnn    7078
nnnnnnnnnn nnnnnnnnnn nnnnnnnnnn nnnnnnnnnn nnnnnnnnnn nnnnnnnnnn    7138
nnnnnnnnnn taggatccgc cggcggccgc gtcgacaatc aacctctgga ttacaaaatt    7198
tgtgaaagat tgactggtat tcttaactat gttgctcctt ttacgctatg tggatacgct    7258
gctttaatgc ctttgtatca tgctattgct tcccgtatgg ctttcatttt ctcctccttg    7318
tataaatcct ggttgctgtc tctttatgag gagttgtggc ccgttgtcag gcaacgtggc    7378
gtggtgtgca ctgtgtttgc tgacgcaacc cccactggtt ggggcattgc caccacctgt    7438
cagctccttt ccgggacttt cgctttcccc ctccctattg ccacggcgga actcatcgcc    7498
gcctgccttg cccgctgctg gacaggggct cggctgttgg gcactgacaa ttccgtggtg    7558
ttgtcgggga agctgacgtc ctttccatgg ctgctcgcct gtgttgccac ctggattctg    7618
cgcgggacgt ccttctgcta cgtcccttcg gccctcaatc cagcggacct tccttcccgc    7678
ggcctgctgc cggctctgcg gcctcttccg cgtcttcgcc ttcgccctca gacgagtcgg    7738
atctcccttt gggccgcctc cccgcctgga attcgagctc ggtaccttta agaccaatga    7798
cttacaaggc agctgtagat cttagccact ttttaaaaga aaaggggga ctggaagggc     7858 taattcactc ccaacgaaga caagatctgc tttttgcttg tactgggtct ctctggttag    7918
accagatctg agcctgggag ctctctggct aactagggaa cccactgctt aagcctcaat    7978
aaagcttgcc ttgagtgctt caagtagtgt gtgcccgtct gttgtgtgac tctggtaact    8038
agagatccct cagacccttt tagtcagtgt ggaaaatctc tagcagtagt agttcatgtc    8098
atcttattat tcagtattta taacttgcaa agaaatgaat atcagagagt gagaggaact    8158
tgtttattgc agcttataat ggttacaaat aaagcaatag catcacaaat ttcacaaata    8218
aagcattttt ttcactgcat tctagttgtg gtttgtccaa actcatcaat gtatcttatc    8278
```

-continued

```
atgtctggct ctagctatcc cgcccctaac tccgcccagt tccgcccatt ctccgcccca    8338
tggctgacta atttttttta tttatgcaga ggccgaggcc gcctcggcct ctgagctatt    8398
ccagaagtag tgaggaggct ttttggagg cctaggcttt tgcgtcgaga cgtacccaat     8458
tcgccctata gtgagtcgta ttacgcgcgc tcactggccg tcgtttttaca acgtcgtgac   8518 tgggaaaacc ctggcgttac ccaacttaat cgccttgcag cacatccccc tttcgccagc    8578
tggcgtaata gcgaagaggc ccgcaccgat cgcccttccc aacagttgcg cagcctgaat    8638
ggcgaatggc gcgacgcgcc ctgtagcggc gcattaagcg cggcgggtgt ggtggttacg    8698
cgcagcgtga ccgctacact tgccagcgcc ctagcgcccg ctcctttcgc tttcttccct    8758
tcctttctcg ccacgttcgc cggctttccc cgtcaagctc taaatcgggg gctcccttta    8818
gggttccgat ttagtgcttt acggcacctc gaccccaaaa aacttgatta gggtgatggt    8878
tcacgtagtg ggccatcgcc ctgatagacg gttttttcgcc ctttgacgtt ggagtccacg   8938
ttctttaata gtggactctt gttccaaact ggaacaacac tcaaccctat ctcggtctat    8998
tcttttgatt tataagggat tttgccgatt tcggcctatt ggttaaaaaa tgagctgatt    9058
taacaaaaat ttaacgcgaa ttttaacaaa atattaacgt ttacaatttc ccaggtggca    9118
cttttcgggg aaatgtgcgc ggaacccta tttgtttatt tttctaaata cattcaaata     9178
tgtatccgct catgagacaa taaccctgat aaatgcttca ataatattga aaaaggaaga    9238
gtatgagtat tcaacatttc cgtgtcgccc ttattccctt ttttgcggca ttttgccttc    9298 ctgttttttgc tcacccagaa acgctggtga aagtaaaaga tgctgaagat cagttgggtg    9358
cacgagtggg ttacatcgaa ctggatctca acagcggtaa gatccttgag agttttcgcc    9418
ccgaagaacg ttttccaatg atgagcactt ttaaagttct gctatgtggc gcggtattat    9478
cccgtattga cgccgggcaa gagcaactcg gtcgccgcat acactattct cagaatgact    9538
tggttg                                                                9544
```

```
<210> SEQ ID NO 33
<211> LENGTH: 239
<212> TYPE: PRT
<213> ORGANISM: Artificial Sequence
<220> FEATURE:
<223> OTHER INFORMATION: [CDS]:4419..5138 from SEQ ID NO 32

<400> SEQUENCE: 33

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
```

```
      130              135              140

Asn Tyr Asn Ser His Asn Val Tyr Ile Met Ala Asp Lys Gln Lys Asn
145                 150              155              160

Gly Ile Lys Val Asn Phe Lys Ile Arg His Asn Ile Glu Asp Gly Ser
                165              170              175

Val Gln Leu Ala Asp His Tyr Gln Gln Asn Thr Pro Ile Gly Asp Gly
            180              185              190

Pro Val Leu Leu Pro Asp Asn His Tyr Leu Ser Thr Gln Ser Ala Leu
        195              200              205

Ser Lys Asp Pro Asn Glu Lys Arg Asp His Met Val Leu Leu Glu Phe
    210              215              220

Val Thr Ala Ala Gly Ile Thr Leu Gly Met Asp Glu Leu Tyr Lys
225              230              235
```

```
<210> SEQ ID NO 34
<211> LENGTH: 9314
<212> TYPE: DNA
<213> ORGANISM: Artificial Sequence
<220> FEATURE:
<223> OTHER INFORMATION: pCCL.PPT.NFATenhsyn.humanIL21co.PGK.CAR.PRE
<220> FEATURE:
<221> NAME/KEY: enhancer
<222> LOCATION: 1858..2237
<223> OTHER INFORMATION: /note="CMV enhancer"
<220> FEATURE:
<221> NAME/KEY: promoter
<222> LOCATION: 2238..2441
<223> OTHER INFORMATION: /note="CMV promoter"
<220> FEATURE:
<221> NAME/KEY: LTR
<222> LOCATION: 2456..2636
<223> OTHER INFORMATION: /note="5B4LTR"
<220> FEATURE:
<221> NAME/KEY: misc_signal
<222> LOCATION: 2683..2808
<223> OTHER INFORMATION: /note="HIV-1 psi packaging signal"
<220> FEATURE:
<221> NAME/KEY: misc_signal
<222> LOCATION: 3301..3534
<223> OTHER INFORMATION: /note="RRE rev response element fo HIV-1,
      allows fo Rev-dependent mRNA export for nucleus to cytoplasm"
<220> FEATURE:
<221> NAME/KEY: misc_feature
<222> LOCATION: 4030..4147
<223> OTHER INFORMATION: /note="cPPT/CTS central purine tract and
      central termination sequence of HIV-1"
<220> FEATURE:
<221> NAME/KEY: promoter
<222> LOCATION: 4174..4417
<223> OTHER INFORMATION: /note="NFATenhsyn"
<220> FEATURE:
<221> NAME/KEY: gene
<222> LOCATION: 4430..4916
<223> OTHER INFORMATION: /gene="human IL21, codon-optimized"
<220> FEATURE:
<221> NAME/KEY: promoter
<222> LOCATION: 4921..5431
<223> OTHER INFORMATION: /note="hPGK promoter"
<220> FEATURE:
<221> NAME/KEY: gene
<222> LOCATION: 5464..6918
<223> OTHER INFORMATION: /note="placeholder for CAR"
      /n=any nucleotide
<220> FEATURE:
<221> NAME/KEY: misc_signal
<222> LOCATION: 6945..7533
<223> OTHER INFORMATION: /note="WPRE"
<220> FEATURE:
<221> NAME/KEY: LTR
<222> LOCATION: 7620..8046
<223> OTHER INFORMATION: /note="3B4LTR (delta U3), self-inactivating 3B4
      long terminal repeat (LTR) of HIV-1"
```

-continued

```
<400> SEQUENCE: 34
agtactcacc agtcacagaa aagcatctta cggatggcat gacagtaaga gaattatgca      60
gtgctgccat aaccatgagt gataacactg cggccaactt acttctgaca acgatcggag     120
gaccgaagga gctaaccgct tttttgcaca acatggggga tcatgtaact cgccttgatc     180
gttgggaacc ggagctgaat gaagccatac caaacgacga gcgtgacacc acgatgcctg     240
tagcaatggc aacaacgttg cgcaaactat taactggcga actacttact ctagcttccc     300
ggcaacaatt aatagactgg atggaggcgg ataaagttgc aggaccactt ctgcgctcgg     360
cccttccggc tggctggttt attgctgata aatctggagc cggtgagcgt gggtctcgcg     420
gtatcattgc agcactgggg ccagatggta agccctcccg tatcgtagtt atctacacga     480
cggggagtca ggcaactatg gatgaacgaa atagacagat cgctgagata ggtgcctcac     540
tgattaagca ttggtaactg tcagaccaag tttactcata tatactttag attgatttaa     600
aacttcattt ttaatttaaa aggatctagg tgaagatcct ttttgataat ctcatgacca     660
aaatccctta acgtgagttt tcgttccact gagcgtcaga ccccgtagaa aagatcaaag     720
gatcttcttg agatcctttt tttctgcgcg taatctgctg cttgcaaaca aaaaaaccac     780
cgctaccagc ggtggtttgt ttgccggatc aagagctacc aactcttttt ccgaaggtaa     840
ctggcttcag cagagcgcag ataccaaata ctgttcttct agtgtagccg tagttaggcc     900
accacttcaa gaactctgta gcaccgccta catacctcgc tctgctaatc ctgttaccag     960
tggctgctgc cagtggcgat aagtcgtgtc ttaccgggtt ggactcaaga cgatagttac    1020
cggataaggc gcagcggtcg ggctgaacgg ggggttcgtg cacacagccc agcttggagc    1080
gaacgaccta caccgaactg agatacctac agcgtgagct atgagaaagc gccacgcttc    1140
ccgaagggag aaaggcggac aggtatccgg taagcggcag ggtcggaaca ggagagcgca    1200
cgagggagct tccaggggga aacgcctggt atctttatag tcctgtcggg tttcgccacc    1260
tctgacttga gcgtcgattt ttgtgatgct cgtcaggggg gcggagccta tggaaaaacg    1320
ccagcaacgc ggcctttta cggttcctgg ccttttgctg gccttttgct cacatgttct    1380
ttcctgcgtt atcccctgat tctgtggata accgtattac cgcctttgag tgagctgata    1440
ccgctcgccg cagccgaacg accgagcgca gcgagtcagt gagcgaggaa gcggaagagc    1500
gcccaatacg caaaccgcct ctccccgcgc gttggccgat tcattaatgc agctggcacg    1560
acaggtttcc cgactggaaa gcgggcagtg agcgcaacgc aattaatgtg agttagctca    1620
ctcattaggc accccaggct ttacacttta tgcttccggc tcgtatgttg tgtggaattg    1680
tgagcggata acaatttcac acaggaaaca gctatgacca tgattacgcc aagcgcgcaa    1740
ttaaccctca ctaaagggaa caaaagctgg agctgcaagc ttggccattg catacgttgt    1800
atccatatca taatatgtac atttatattg gctcatgtcc aacattaccg ccatgttgac    1860
attgattatt gactagttat taatagtaat caattacggg gtcattagtt catagcccat    1920
atatggagtt ccgcgttaca taacttacgg taaatggccc gcctggctga ccgcccaacg    1980
acccccgccc attgacgtca ataatgacgt atgttcccat agtaacgcca atagggactt    2040
tccattgacg tcaatgggtg gagtatttac ggtaaactgc ccacttggca gtacatcaag    2100
tgtatcatat gccaagtacg cccccctattg acgtcaatga cggtaaatgg cccgcctggc    2160
attatgccca gtacatgacc ttatgggact ttcctacttg gcagtacatc tacgtattag    2220
tcatcgctat taccatggtg atgcggtttt ggcagtacat caatgggcgt ggatagcggt    2280
```

-continued

```
ttgactcacg gggatttcca agtctccacc ccattgacgt caatgggagt ttgttttggc    2340
accaaaatca acgggacttt ccaaaatgtc gtaacaactc cgccccattg acgcaaatgg    2400
gcggtaggcg tgtacggtgg gaggtctata taagcagagc tcgtttagtg aaccggggtc    2460
tctctggtta gaccagatct gagcctggga gctctctggc taactaggga acccactgct    2520
taagcctcaa taaagcttgc cttgagtgct tcaagtagtg tgtgcccgtc tgttgtgtga    2580
ctctggtaac tagagatccc tcagaccctt ttagtcagtg tggaaaatct ctagcagtgg    2640
cgcccgaaca gggacttgaa agcgaaaggg aaaccagagg agctctctcg acgcaggact    2700
cggcttgctg aagcgcgcac ggcaagaggc gaggggcggc gactggtgag tacgccaaaa    2760
attttgacta gcggaggcta aaggagaga gatgggtgcg agagcgtcag tattaagcgg    2820
gggagaatta gatcgcgatg ggaaaaaatt cggttaaggc cagggggaaa gaaaaaatat    2880
aaattaaaac atatagtatg ggcaagcagg gagctagaac gattcgcagt taatcctggc    2940
ctgttagaaa catcagaagg ctgtagacaa atactgggac agctacaacc atcccttcag    3000
acaggatcag aagaacttag atcattatat aatacagtag caaccctcta ttgtgtgcat    3060
caaaggatag agataaaaga caccaaggaa gctttagaca agatagagga agagcaaaac    3120
aaaagtaaga ccaccgcaca gcaagcggcc gctgatcttc agacctggag gaggagatat    3180
gagggacaat tggagaagtg aattatataa atataaagta gtaaaaattg aaccattagg    3240
agtagcaccc accaaggcaa agagaagagt ggtgcagaga gaaaaaagag cagtgggaat    3300
aggagctttg ttccttgggt tcttgggagc agcaggaagc actatgggcg cagcctcaat    3360
gacgctgacg gtacaggcca gacaattatt gtctggtata gtgcagcagc agaacaattt    3420
gctgagggct attgaggcgc aacagcatct gttgcaactc acagtctggg gcatcaagca    3480
gctccaggca agaatcctgg ctgtggaaag atacctaaag gatcaacagc tcctggggat    3540
ttggggttgc tctggaaaac tcatttgcac cactgctgtg ccttggaatg ctagttggag    3600
taataaatct ctggaacaga tttggaatca cacgacctgg atggagtggg acagagaaat    3660
taacaattac acaagcttaa tacactcctt aattgaagaa tcgcaaaacc agcaagaaaa    3720
gaatgaacaa gaattattgg aattagataa atgggcaagt ttgtggaatt ggtttaacat    3780
aacaaattgg ctgtggtata taaaattatt cataatgata gtaggaggct tggtaggttt    3840
aagaatagtt tttgctgtac tttctatagt gaatagagtt aggcagggat attcaccatt    3900
atcgtttcag acccacctcc caaccccgag gggacccgac aggcccgaag gaatagaaga    3960
agaaggtgga gagagagaca gagacagatc cattcgatta gtgaacggat ctcgacggta    4020
tcggttaact tttaaaagaa aaggggggat tggggggtac agtgcagggg aaagaatagt    4080
agacataata gcaacagaca tacaaactaa agaattacaa aaacaaatta caaaaattca    4140
aaattttatc gatcacgaga ctagcctcga gcgtggagga aaaactgttt catacagaag    4200
gcgtggagga aaaactgttt catacagaag gcgtggagga aaaactgttt catacagaag    4260
gcgtggagga aaaactgttt catacagaag gcgtggagga aaaactgttt catacagaag    4320
gcgtggagga aaaactgttt catacagaag gcgtctgcag gagactctag agggtatata    4380
atggtttaaa cttaagcttg gtaccggggcc cccgaagacg cgtgccacca tggaacggat    4440
cgtgatctgc ctgatggtca tcttcctggg caccctggtg cacaagagca gctctcaggg    4500
ccaagaccgg cacatgatcc ggatgagaca gctgatcgac atcgtggacc agctgaagaa    4560
ctacgtgaac gacctggtgc ctgagttcct gcctgctcct gaggacgtgg aaacaaactg    4620
cgagtggagc gccttcagct gcttccagaa ggcccagctg aaaagcgcca acaccggcaa    4680
```

```
caacgagcgg atcatcaacg tgtccatcaa gaagctgaag cggaagcctc ctagcaccaa   4740
cgccggaaga aggcagaagc acagactgac ctgtcctagc tgcgacagct acgagaagaa   4800
gcctccaaaa gagttcctgg aacggttcaa gagcctgctg cagaagatga tccaccagca   4860
cctgagcagc agaacccacg gcagcgagga ttcttgatgt acaagtaatc gaattcccac   4920
ggggttgggg ttgcgccttt tccaaggcag ccctgggttt gcgcagggac gcggctgctc   4980
tgggcgtggt tccgggaaac gcagcggcgc cgacctgggg tctcgcacat tcttcacgtc   5040
cgttcgcagc gtcacccgga tcttcgccgc taccttgtg ggcccccgg cgacgcttcc     5100 tgctccgccc ctaagtcggg aaggttcctt gcggttcgcg gcgtgccgga cgtgacaaac   5160
ggaagccgca cgtctcacta gtaccctcgc agacggacag cgccagggag caatggcagc   5220
gcgccgaccg cgatgggctg tggccaatag cggctgctca gcggggcgcg ccgagagcag   5280
cggccgggaa ggggcggtgc gggaggcggg gtgtggggcg gtagtgtggg ccctgttcct   5340
gcccgcgcgg tgttccgcat tctgcaagcc tccggagcgc acgtcggcag tcggctccct   5400
cgttgaccga atcaccgacc tctctcccca gggggatcca ccggtcacgt ggctagcgcc   5460
accnnnnnnn nnnnnnnnnn nnnnnnnnnn nnnnnnnnnn nnnnnnnnnn nnnnnnnnnn   5520
nnnnnnnnnn nnnnnnnnnn nnnnnnnnnn nnnnnnnnnn nnnnnnnnnn nnnnnnnnnn   5580
nnnnnnnnnn nnnnnnnnnn nnnnnnnnnn nnnnnnnnnn nnnnnnnnnn nnnnnnnnnn   5640
nnnnnnnnnn nnnnnnnnnn nnnnnnnnnn nnnnnnnnnn nnnnnnnnnn nnnnnnnnnn   5700
nnnnnnnnnn nnnnnnnnnn nnnnnnnnnn nnnnnnnnnn nnnnnnnnnn nnnnnnnnnn   5760
nnnnnnnnnn nnnnnnnnnn nnnnnnnnnn nnnnnnnnnn nnnnnnnnnn nnnnnnnnnn   5820
nnnnnnnnnn nnnnnnnnnn nnnnnnnnnn nnnnnnnnnn nnnnnnnnnn nnnnnnnnnn   5880
nnnnnnnnnn nnnnnnnnnn nnnnnnnnnn nnnnnnnnnn nnnnnnnnnn nnnnnnnnnn   5940
nnnnnnnnnn nnnnnnnnnn nnnnnnnnnn nnnnnnnnnn nnnnnnnnnn nnnnnnnnnn   6000
nnnnnnnnnn nnnnnnnnnn nnnnnnnnnn nnnnnnnnnn nnnnnnnnnn nnnnnnnnnn   6060
nnnnnnnnnn nnnnnnnnnn nnnnnnnnnn nnnnnnnnnn nnnnnnnnnn nnnnnnnnnn   6120
nnnnnnnnnn nnnnnnnnnn nnnnnnnnnn nnnnnnnnnn nnnnnnnnnn nnnnnnnnnn   6180
nnnnnnnnnn nnnnnnnnnn nnnnnnnnnn nnnnnnnnnn nnnnnnnnnn nnnnnnnnnn   6240
nnnnnnnnnn nnnnnnnnnn nnnnnnnnnn nnnnnnnnnn nnnnnnnnnn nnnnnnnnnn   6300
nnnnnnnnnn nnnnnnnnnn nnnnnnnnnn nnnnnnnnnn nnnnnnnnnn nnnnnnnnnn   6360
nnnnnnnnnn nnnnnnnnnn nnnnnnnnnn nnnnnnnnnn nnnnnnnnnn nnnnnnnnnn   6420
nnnnnnnnnn nnnnnnnnnn nnnnnnnnnn nnnnnnnnnn nnnnnnnnnn nnnnnnnnnn   6480
nnnnnnnnnn nnnnnnnnnn nnnnnnnnnn nnnnnnnnnn nnnnnnnnnn nnnnnnnnnn   6540
nnnnnnnnnn nnnnnnnnnn nnnnnnnnnn nnnnnnnnnn nnnnnnnnnn nnnnnnnnnn   6600
nnnnnnnnnn nnnnnnnnnn nnnnnnnnnn nnnnnnnnnn nnnnnnnnnn nnnnnnnnnn   6660
nnnnnnnnnn nnnnnnnnnn nnnnnnnnnn nnnnnnnnnn nnnnnnnnnn nnnnnnnnnn   6720
nnnnnnnnnn nnnnnnnnnn nnnnnnnnnn nnnnnnnnnn nnnnnnnnnn nnnnnnnnnn   6780
nnnnnnnnnn nnnnnnnnnn nnnnnnnnnn nnnnnnnnnn nnnnnnnnnn nnnnnnnnnn   6840
nnnnnnnnnn nnnnnnnnnn nnnnnnnnnn nnnnnnnnnn nnnnnnnnnn nnnnnnnnnn   6900
nnnnnnnnnn nnnnnnnnta ggatccgccg gcggccgcgt cgacaatcaa cctctggatt   6960
acaaaatttg tgaaagattg actggtattc ttaactatgt tgctcctttt acgctatgtg   7020
```

-continued

```
gatacgctgc tttaatgcct ttgtatcatg ctattgcttc ccgtatggct ttcattttct    7080
cctccttgta taaatcctgg ttgctgtctc tttatgagga gttgtggccc gttgtcaggc    7140
aacgtggcgt ggtgtgcact gtgtttgctg acgcaacccc cactggttgg ggcattgcca    7200
ccacctgtca gctcctttcc gggactttcg cttttccccct ccctattgcc acggcggaac    7260
tcatcgccgc ctgccttgcc cgctgctgga caggggctcg gctgttgggc actgacaatt    7320
ccgtggtgtt gtcggggaag ctgacgtcct ttccatggct gctcgcctgt gttgccacct    7380
ggattctgcg cgggacgtcc ttctgctacg tcccttcggc cctcaatcca gcggaccttc    7440
cttcccgcgg cctgctgccg gctctgcggc ctcttccgcg tcttcgcctt cgccctcaga    7500
cgagtcggat ctcccttttgg gccgcctccc cgcctggaat tcgagctcgg tacctttaag    7560
accaatgact tacaaggcag ctgtagatct tagccacttt ttaaaagaaa aggggggact    7620
ggaagggcta attcactccc aacgaagaca agatctgctt tttgcttgta ctgggtctct    7680
ctggttagac cagatctgag cctgggagct ctctggctaa ctagggaacc cactgcttaa    7740
gcctcaataa agcttgcctt gagtgcttca agtagtgtgt gcccgtctgt tgtgtgactc    7800
tggtaactag agatccctca gacccttttta gtcagtgtgg aaaatctcta gcagtagtag    7860
ttcatgtcat cttattattc agtatttata acttgcaaag aaatgaatat cagagagtga    7920
gaggaacttg tttattgcag cttataatgg ttacaaataa agcaatagca tcacaaattt    7980
cacaaataaa gcattttttt cactgcattc tagttgtggt ttgtccaaac tcatcaatgt    8040
atcttatcat gtctggctct agctatcccg ccccctaactc cgcccagttc cgcccattct    8100
ccgccccatg gctgactaat tttttttatt tatgcagagg ccgaggccgc ctcggcctct    8160
gagctattcc agaagtagtg aggaggcttt tttggaggcc taggcttttg cgtcgagacg    8220
tacccaattc gccctatagt gagtcgtatt acgcgcgctc actggccgtc gttttacaac    8280
gtcgtgactg ggaaaaccct ggcgttaccc aacttaatcg ccttgcagca catcccccctt    8340 tcgccagctg gcgtaatagc gaagaggccc gcaccgatcg cccttcccaa cagttgcgca    8400
gcctgaatgg cgaatggcgc gacgcgccct gtagcggcgc attaagcgcg gcgggtgtgg    8460
tggttacgcg cagcgtgacc gctacacttg ccagcgccct agcgcccgct cctttcgctt    8520
tcttcccttc ctttctcgcc acgttcgccg gctttccccg tcaagctcta aatcgggggc    8580
tccctttagg gttccgattt agtgctttac ggcacctcga ccccaaaaaa cttgattagg    8640
gtgatggttc acgtagtggg ccatcgccct gatagacggt ttttcgccct ttgacgttgg    8700
agtccacgtt ctttaatagt ggactcttgt tccaaactgg aacaacactc aaccctatct    8760
cggtctattc ttttgattta aagggattt tgccgatttc ggcctattgg ttaaaaaatg    8820
agctgattta acaaaaattt aacgcgaatt ttaacaaaat attaacgttt acaatttccc    8880
aggtggcact tttcggggaa atgtgcgcgg aaccccctatt tgtttatttt tctaaataca    8940
ttcaaatatg tatccgctca tgagacaata accctgataa atgcttcaat aatattgaaa    9000
aaggaagagt atgagtattc aacatttccg tgtcgccctt attcccttttt ttgcggcatt    9060 ttgccttcct gtttttgctc acccagaaac gctggtgaaa gtaaaagatg ctgaagatca    9120
gttgggtgca cgagtgggtt acatcgaact ggatctcaac agcggtaaga tccttgagag    9180
ttttcgcccc gaagaacgtt ttccaatgat gagcactttt aaagttctgc tatgtggcgc    9240
ggtattatcc cgtattgacg ccgggcaaga gcaactcggt cgccgcatac actattctca    9300
gaatgacttg gttg                                                     9314
```

```
<210> SEQ ID NO 35
<211> LENGTH: 9692
<212> TYPE: DNA
<213> ORGANISM: Artificial Sequence
<220> FEATURE:
<223> OTHER INFORMATION: pCCL.PPT.NFATenhsyn.TRAIL.PGK.CAR.PRE
<220> FEATURE:
<221> NAME/KEY: enhancer
<222> LOCATION: 1858..2237
<223> OTHER INFORMATION: /note="CMV enhancer"
<220> FEATURE:
<221> NAME/KEY: promoter
<222> LOCATION: 2238..2441
<223> OTHER INFORMATION: /note="CMV promoter"
<220> FEATURE:
<221> NAME/KEY: LTR
<222> LOCATION: 2456..2636
<223> OTHER INFORMATION: /note="5B4LTR, truncated"
<220> FEATURE:
<221> NAME/KEY: misc_signal
<222> LOCATION: 2683..2808
<223> OTHER INFORMATION: /note="psi packaging signal of HIV-1"
<220> FEATURE:
<221> NAME/KEY: misc_signal
<222> LOCATION: 3301..3534
<223> OTHER INFORMATION: /note="RRE of HIV-1"
<220> FEATURE:
<221> NAME/KEY: misc_signal
<222> LOCATION: 4030..4147
<223> OTHER INFORMATION: /note="cPPT/CTS"
<220> FEATURE:
<221> NAME/KEY: promoter
<222> LOCATION: 4174..4417
<223> OTHER INFORMATION: /note="NFATenhsyn"
<220> FEATURE:
<221> NAME/KEY: gene
<222> LOCATION: 4430..5275
<223> OTHER INFORMATION: /note="TRAIL"
<220> FEATURE:
<221> NAME/KEY: promoter
<222> LOCATION: 5299..5809
<223> OTHER INFORMATION: /note="hPGK promoter"
<220> FEATURE:
<221> NAME/KEY: gene
<222> LOCATION: 5842..7296
<223> OTHER INFORMATION: /note="placeholder for CAR"
     /n=any nucleotide
<220> FEATURE:
<221> NAME/KEY: misc_signal
<222> LOCATION: 7323..7911
<223> OTHER INFORMATION: /note="WPRE"
<220> FEATURE:
<221> NAME/KEY: LTR
<222> LOCATION: 7998..8231
<223> OTHER INFORMATION: /note="3B4LTR (delta U3)"

<400> SEQUENCE: 35
agtactcacc agtcacagaa aagcatctta cggatggcat gacagtaaga gaattatgca        60
gtgctgccat aaccatgagt gataacactg cggccaactt acttctgaca acgatcggag       120
gaccgaagga gctaaccgct tttttgcaca acatggggga tcatgtaact cgccttgatc       180
gttgggaacc ggagctgaat gaagccatac caaacgacga gcgtgacacc acgatgcctg       240
tagcaatggc aacaacgttg cgcaaactat taactggcga actacttact ctagcttccc       300
ggcaacaatt aatagactgg atggaggcgg ataaagttgc aggaccactt ctgcgctcgg       360
cccttccggc tggctggttt attgctgata aatctggagc cggtgagcgt gggtctcgcg       420
gtatcattgc agcactgggg ccagatggta agccctcccg tatcgtagtt atctacacga       480
cggggagtca ggcaactatg gatgaacgaa atagacagat cgctgagata ggtgcctcac       540
tgattaagca ttggtaactg tcagaccaag tttactcata tatactttag attgatttaa       600
aacttcattt ttaatttaaa aggatctagg tgaagatcct ttttgataat ctcatgacca       660
```

-continued

```
aaatcccta  acgtgagttt  tcgttccact  gagcgtcaga  ccccgtagaa  aagatcaaag      720
gatcttcttg  agatccttt   tttctgcgcg  taatctgctg  cttgcaaaca  aaaaaaccac      780
cgctaccagc  ggtggtttgt  ttgccggatc  aagagctacc  aactcttttt  ccgaaggtaa      840
ctggcttcag  cagagcgcag  ataccaaata  ctgttcttct  agtgtagccg  tagttaggcc      900
accacttcaa  gaactctgta  gcaccgccta  catacctcgc  tctgctaatc  ctgttaccag      960
tggctgctgc  cagtggcgat  aagtcgtgtc  ttaccgggtt  ggactcaaga  cgatagttac     1020
cggataaggc  gcagcggtcg  ggctgaacgg  ggggttcgtg  cacacagccc  agcttggagc     1080
gaacgaccta  caccgaactg  agatacctac  agcgtgagct  atgagaaagc  gccacgcttc     1140
ccgaagggag  aaaggcggac  aggtatccgg  taagcggcag  ggtcggaaca  ggagagcgca     1200
cgagggagct  tccaggggga  aacgcctggt  atctttatag  tcctgtcggg  tttcgccacc     1260
tctgacttga  gcgtcgattt  ttgtgatgct  cgtcagggg   gcggagccta  tggaaaaacg     1320
ccagcaacgc  ggcctttta   cggttcctgg  ccttttgctg  gccttttgct  cacatgttct     1380
ttcctgcgtt  atcccctgat  tctgtggata  accgtattac  cgcctttgag  tgagctgata     1440
ccgctcgccg  cagccgaacg  accgagcgca  gcgagtcagt  gagcgaggaa  gcggaagagc     1500
gcccaatacg  caaaccgcct  ctccccgcgc  gttggccgat  tcattaatgc  agctggcacg     1560
acaggtttcc  cgactggaaa  gcgggcagtg  agcgcaacgc  aattaatgtg  agttagctca     1620
ctcattaggc  accccaggct  ttacacttta  tgcttccggc  tcgtatgttg  tgtggaattg     1680
tgagcggata  acaatttcac  acaggaaaca  gctatgacca  tgattacgcc  aagcgcgcaa     1740
ttaaccctca  ctaaagggaa  caaaagctgg  agctgcaagc  ttggccattg  catacgttgt     1800
atccatatca  taatatgtac  atttatattg  gctcatgtcc  aacattaccg  ccatgttgac     1860
attgattatt  gactagttat  taatagtaat  caattacggg  gtcattagtt  catagcccat     1920
atatggagtt  ccgcgttaca  taacttacgg  taaatggccc  gcctggctga  ccgcccaacg     1980
acccccgccc  attgacgtca  ataatgacgt  atgttcccat  agtaacgcca  atagggactt     2040
tccattgacg  tcaatgggtg  gagtatttac  ggtaaactgc  ccacttggca  gtacatcaag     2100
tgtatcatat  gccaagtacg  ccccctattg  acgtcaatga  cggtaaatgg  cccgcctggc     2160
attatgccca  gtacatgacc  ttatgggact  ttcctacttg  gcagtacatc  tacgtattag     2220
tcatcgctat  taccatggtg  atgcggtttt  ggcagtacat  caatgggcgt  ggatagcggt     2280
ttgactcacg  gggatttcca  agtctccacc  ccattgacgt  caatgggagt  ttgttttggc     2340
accaaaatca  acgggacttt  ccaaaatgtc  gtaacaactc  cgccccattg  acgcaaatgg     2400
gcggtaggcg  tgtacggtgg  gaggtctata  taagcagagc  tcgtttagtg  aaccggggtc     2460
tctctggtta  gaccagatct  gagcctggga  gctctctggc  taactaggga  acccactgct     2520
taagcctcaa  taaagcttgc  cttgagtgct  tcaagtagtg  tgtgcccgtc  tgttgtgtga     2580
ctctggtaac  tagagatccc  tcagaccctt  ttagtcagtg  tggaaaatct  ctagcagtgg     2640
cgcccgaaca  gggacttgaa  agcgaaaggg  aaaccagagg  agctctctcg  acgcaggact     2700
cggcttgctg  aagcgcgcac  ggcaagaggc  gaggggcggc  gactggtgag  tacgccaaaa     2760
attttgacta  gcggaggcta  gaaggagaga  gatgggtgcg  agagcgtcag  tattaagcgg     2820
gggagaatta  gatcgcgatg  ggaaaaaatt  cggttaaggc  caggggggaa  gaaaaaatat     2880
aaattaaaac  atatagtatg  ggcaagcagg  gagctagaac  gattcgcagt  taatcctggc     2940
ctgttagaaa  catcagaagg  ctgtagacaa  atactgggac  agctacaacc  atcccttcag     3000
```

```
acaggatcag aagaacttag atcattatat aatacagtag caaccctcta ttgtgtgcat    3060
caaaggatag agataaaaga caccaaggaa gctttagaca agatagagga agagcaaaac    3120
aaaagtaaga ccaccgcaca gcaagcggcc gctgatcttc agacctggag gaggagatat    3180
gagggacaat tggagaagtg aattatataa atataaagta gtaaaaattg aaccattagg    3240
agtagcaccc accaaggcaa agagaagagt ggtgcagaga gaaaaaagag cagtgggaat    3300
aggagctttg ttccttgggt tcttgggagc agcaggaagc actatgggcg cagcctcaat    3360
gacgctgacg gtacaggcca gacaattatt gtctggtata gtgcagcagc agaacaattt    3420
gctgagggct attgaggcgc aacagcatct gttgcaactc acagtctggg gcatcaagca    3480
gctccaggca agaatcctgg ctgtggaaag atacctaaag gatcaacagc tcctggggat    3540
ttggggttgc tctggaaaac tcatttgcac cactgctgtg ccttggaatg ctagttggag    3600
taataaatct ctggaacaga tttggaatca cacgacctgg atggagtggg acagagaaat    3660
taacaattac acaagcttaa tacactcctt aattgaagaa tcgcaaaacc agcaagaaaa    3720
gaatgaacaa gaattattgg aattagataa atgggcaagt ttgtggaatt ggtttaacat    3780
aacaaattgg ctgtggtata taaaattatt cataatgata gtaggaggct tggtaggttt    3840
aagaatagtt tttgctgtac tttctatagt gaatagagtt aggcagggat attcaccatt    3900
atcgtttcag acccacctcc caaccccgag gggacccgac aggcccgaag gaatagaaga    3960
agaaggtgga gagagagaca gagacagatc cattcgatta gtgaacggat ctcgacggta    4020
tcggttaact tttaaaagaa aaggggggat tggggggtac agtgcagggg aaagaatagt    4080
agacataata gcaacagaca tacaaactaa agaattacaa aaacaaatta caaaaattca    4140
aaattttatc gatcacgaga ctagcctcga gcgtggagga aaaactgttt catacagaag    4200
gcgtggagga aaaactgttt catacagaag gcgtggagga aaaactgttt catacagaag    4260
gcgtggagga aaaactgttt catacagaag gcgtggagga aaaactgttt catacagaag    4320
gcgtggagga aaaactgttt catacagaag gcgtctgcag gagactctag agggtatata    4380
atggtttaaa cttaagcttg gtaccgggcc cccgaagacg cgtgccacca tggctatgat    4440
ggaagtgcaa ggcggaccta gcctgggcca gacatgtgtg ctgatcgtga tcttcaccgt    4500
gctgctgcag agcctgtgtg tggccgtgac ctacgtgtac ttcaccaacg agctgaagca    4560
gatgcaggac aagtacagca agagcggaat cgcctgcttc ctgaaagagg acgacagcta    4620
ctgggacccc aacgacgaag agagcatgaa cagcccctgc tggcaagtga agtggcagct    4680
gagacagctc gtgcggaaga tgatcctgcg gaccagcgaa gagacaatca gcaccgtgca    4740
agagaagcag cagaacatca gccctctcgt cagagagcgg ggacctcaga gagtggccgc    4800
tcacattact ggcaccagag gcagaagcaa caccctgagc agcccaaaca gcaagaacga    4860
gaaggccctg ggcagaaaga tcaacagctg ggagagcagc agatccggcc acagctttct    4920
gagcaacctg cacctgagaa acggcgagct ggtcatccac gagaagggct tctactacat    4980
ctacagccag acctacttcc ggttccaaga ggaaatcaaa gagaatacca agaacgacaa    5040
gcagatggtg cagtacatct ataagtacac gagctacccc gatccgatcc tgctgatgaa    5100
gtccgccaga aacagctgct ggtccaagga tgccgagtac ggcctgtata gcatctacca    5160
aggcggcatc ttcgagctga aagagaatga ccggatcttc gtgtccgtga ccaatgagca    5220
cctgatcgac atggaccacg aggccagctt tttcggcgcc tttcttgtgg gctgatgtac    5280
aagtaatcga attcccacgg ggttgggggtt gcgccttttc caaggcagcc ctgggtttgc    5340
gcagggacgc ggctgctctg ggcgtggttc cgggaaacgc agcggcgccg accctgggtc    5400
```

```
tcgcacattc ttcacgtccg ttcgcagcgt cacccggatc ttcgccgcta cccttgtggg    5460 cccccggcg acgcttcctg ctccgcccct aagtcgggaa ggttccttgc ggttcgcggc     5520
gtgccggacg tgacaaacgg aagccgcacg tctcactagt accctcgcag acggacagcg    5580
ccagggagca atggcagcgc gccgaccgcg atgggctgtg gccaatagcg gctgctcagc    5640
ggggcgcgcc gagagcagcg gccgggaagg ggcggtgcgg gaggcggggt gtggggcggt    5700
agtgtgggcc ctgttcctgc ccgcgcggtg ttccgcattc tgcaagcctc cggagcgcac    5760
gtcggcagtc ggctccctcg ttgaccgaat caccgacctc tctccccagg gggatccacc    5820
ggtcacgtgg ctagcgccac cnnnnnnnnn nnnnnnnnnn nnnnnnnnnn nnnnnnnnnn    5880
nnnnnnnnnn nnnnnnnnnn nnnnnnnnnn nnnnnnnnnn nnnnnnnnnn nnnnnnnnnn    5940
nnnnnnnnnn nnnnnnnnnn nnnnnnnnnn nnnnnnnnnn nnnnnnnnnn nnnnnnnnnn    6000
nnnnnnnnnn nnnnnnnnnn nnnnnnnnnn nnnnnnnnnn nnnnnnnnnn nnnnnnnnnn    6060
nnnnnnnnnn nnnnnnnnnn nnnnnnnnnn nnnnnnnnnn nnnnnnnnnn nnnnnnnnnn    6120
nnnnnnnnnn nnnnnnnnnn nnnnnnnnnn nnnnnnnnnn nnnnnnnnnn nnnnnnnnnn    6180
nnnnnnnnnn nnnnnnnnnn nnnnnnnnnn nnnnnnnnnn nnnnnnnnnn nnnnnnnnnn    6240
nnnnnnnnnn nnnnnnnnnn nnnnnnnnnn nnnnnnnnnn nnnnnnnnnn nnnnnnnnnn    6300
nnnnnnnnnn nnnnnnnnnn nnnnnnnnnn nnnnnnnnnn nnnnnnnnnn nnnnnnnnnn    6360
nnnnnnnnnn nnnnnnnnnn nnnnnnnnnn nnnnnnnnnn nnnnnnnnnn nnnnnnnnnn    6420
nnnnnnnnnn nnnnnnnnnn nnnnnnnnnn nnnnnnnnnn nnnnnnnnnn nnnnnnnnnn    6480
nnnnnnnnnn nnnnnnnnnn nnnnnnnnnn nnnnnnnnnn nnnnnnnnnn nnnnnnnnnn    6540
nnnnnnnnnn nnnnnnnnnn nnnnnnnnnn nnnnnnnnnn nnnnnnnnnn nnnnnnnnnn    6600
nnnnnnnnnn nnnnnnnnnn nnnnnnnnnn nnnnnnnnnn nnnnnnnnnn nnnnnnnnnn    6660
nnnnnnnnnn nnnnnnnnnn nnnnnnnnnn nnnnnnnnnn nnnnnnnnnn nnnnnnnnnn    6720
nnnnnnnnnn nnnnnnnnnn nnnnnnnnnn nnnnnnnnnn nnnnnnnnnn nnnnnnnnnn    6780
nnnnnnnnnn nnnnnnnnnn nnnnnnnnnn nnnnnnnnnn nnnnnnnnnn nnnnnnnnnn    6840
nnnnnnnnnn nnnnnnnnnn nnnnnnnnnn nnnnnnnnnn nnnnnnnnnn nnnnnnnnnn    6900
nnnnnnnnnn nnnnnnnnnn nnnnnnnnnn nnnnnnnnnn nnnnnnnnnn nnnnnnnnnn    6960
nnnnnnnnnn nnnnnnnnnn nnnnnnnnnn nnnnnnnnnn nnnnnnnnnn nnnnnnnnnn    7020
nnnnnnnnnn nnnnnnnnnn nnnnnnnnnn nnnnnnnnnn nnnnnnnnnn nnnnnnnnnn    7080
nnnnnnnnnn nnnnnnnnnn nnnnnnnnnn nnnnnnnnnn nnnnnnnnnn nnnnnnnnnn    7140
nnnnnnnnnn nnnnnnnnnn nnnnnnnnnn nnnnnnnnnn nnnnnnnnnn nnnnnnnnnn    7200
nnnnnnnnnn nnnnnnnnnn nnnnnnnnnn nnnnnnnnnn nnnnnnnnnn nnnnnnnnnn    7260
nnnnnnnnnn nnnnnnnnnn nnnnnnnnnn nnnnnnntagg atccgccggc ggccgcgtcg    7320
acaatcaacc tctggattac aaaatttgtg aaagattgac tggtattctt aactatgttg    7380
ctccttttac gctatgtgga tacgctgctt taatgccttt gtatcatgct attgcttccc    7440
gtatggcttt cattttctcc tccttgtata aatcctggtt gctgtctctt tatgaggagt    7500
tgtggcccgt tgtcaggcaa cgtggcgtgg tgtgcactgt gtttgctgac gcaacccccca    7560 ctggttgggg cattgccacc acctgtcagc tcctttccgg gactttcgct ttccccctcc    7620
ctattgccac ggcggaactc atcgccgcct gccttgcccg ctgctggaca ggggctcggc    7680
tgttgggcac tgacaattcc gtggtgttgt cggggaagct gacgtccttt ccatggctgc    7740
```

-continued

```
tcgcctgtgt tgccacctgg attctgcgcg ggacgtcctt ctgctacgtc ccttcggccc    7800
tcaatccagc ggaccttcct tcccgcggcc tgctgccggc tctgcggcct cttccgcgtc    7860
ttcgccttcg ccctcagacg agtcggatct ccctttgggc cgcctccccg cctggaattc    7920
gagctcggta cctttaagac caatgactta caaggcagct gtagatctta gccacttttt    7980
aaaagaaaag gggggactgg aagggctaat tcactcccaa cgaagacaag atctgctttt    8040
tgcttgtact gggtctctct ggttagacca gatctgagcc tgggagctct ctggctaact    8100
agggaaccca ctgcttaagc ctcaataaag cttgccttga gtgcttcaag tagtgtgtgc    8160
ccgtctgttg tgtgactctg gtaactagag atccctcaga cccttttagt cagtgtggaa    8220
aatctctagc agtagtagtt catgtcatct tattattcag tatttataac ttgcaaagaa    8280
atgaatatca gagagtgaga ggaacttgtt tattgcagct tataatggtt acaaataaag    8340
caatagcatc acaaatttca caaataaagc attttttttca ctgcattcta gttgtggttt    8400
gtccaaactc atcaatgtat cttatcatgt ctggctctag ctatcccgcc cctaactccg    8460
cccagttccg cccattctcc gccccatggc tgactaattt tttttattta tgcagaggcc    8520
gaggccgcct cggcctctga gctattccag aagtagtgag gaggcttttt tggaggccta    8580
ggcttttgcg tcgagacgta cccaattcgc cctatagtga gtcgtattac gcgcgctcac    8640
tggccgtcgt tttacaacgt cgtgactggg aaaaccctgg cgttacccaa cttaatcgcc    8700
ttgcagcaca tcccccttttc gccagctggc gtaatagcga agaggcccgc accgatcgcc    8760
cttcccaaca gttgcgcagc ctgaatggcg aatggcgcga cgcgccctgt agcggcgcat    8820
taagcgcggc gggtgtggtg gttacgcgca gcgtgaccgc tacacttgcc agcgccctag    8880
cgcccgctcc tttcgctttc ttcccttcct ttctcgccac gttcgccggc tttccccgtc    8940
aagctctaaa tcgggggctc cctttagggt tccgatttag tgctttacgg cacctcgacc    9000
ccaaaaaact tgattagggt gatggttcac gtagtgggcc atcgccctga tagacggttt    9060
ttcgcccttt gacgttggag tccacgttct ttaatagtgg actcttgttc caaactggaa    9120
caacactcaa ccctatctcg gtctattctt ttgatttata agggattttg ccgatttcgg    9180
cctattggtt aaaaaatgag ctgatttaac aaaaatttaa cgcgaatttt aacaaaatat    9240
taacgtttac aatttcccag gtggcacttt tcggggaaat gtgcgcggaa cccctatttg    9300
tttatttttc taaatacatt caaatatgta tccgctcatg agacaataac cctgataaat    9360
gcttcaataa tattgaaaaa ggaagagtat gagtattcaa catttccgtg tcgcccttat    9420 tcccttttttt gcggcatttt gccttcctgt ttttgctcac ccagaaacgc tggtgaaagt    9480
aaaagatgct gaagatcagt tgggtgcacg agtgggttac atcgaactgg atctcaacag    9540
cggtaagatc cttgagagtt ttcgccccga agaacgtttt ccaatgatga gcactttttaa    9600 agttctgcta tgtggcgcgg tattatcccg tattgacgcc gggcaagagc aactcggtcg    9660
ccgcatacac tattctcaga atgacttggt tg                                  9692
```

ALL-IN ONE VECTOR FOR CAR AND THERAPEUTIC EFFECTOR MOLECULE

INCORPORATION BY REFERENCE OF THE SEQUENCE LISTING

The content of the ASCII text file of the sequence listing name 1BD0981, 215714 bytes in size, created on Oct. 4, 2022, is incorporated herein by reference in its entirety.

The present invention relates to a vector for the constitutive expression of a second protein and the inducible expression of at least one first molecule, also referred to as a first protein, in mammalian cells. Generally, the vector contains an expression cassette for constitutive expression of the second protein and an expression cassette for inducible expression of the first molecule, wherein the second protein is a receptor molecule, e.g. a receptor, e.g. a CAR or a TCR, capable of binding a cognate antigen, and the first molecule is an effector molecule and expression of the first molecule is induced by binding of the second protein to its cognate antigen. The vector can be preferentially used for introduction and expression in immune cells, in particular lymphocytes, NK cells, and macrophages. The second protein and first molecule can be clinically relevant proteins. Accordingly, the vector is suitable for use in therapy, e.g. for use in immune therapy, especially in the treatment of cancer, including leukemia, lymphoma and solid tumours, or for use in immunomodulation, e.g. for use in the treatment of autoimmune diseases or for providing immune tolerance, e.g. immune tolerance for a cognate antigen. In a specific embodiment of the invention, the vector comprises a constitutive expression cassette encoding as the second protein a chimeric antigen receptor (CAR) or a T-cell receptor (TCR) and an inducible expression cassette encoding as the first molecule a therapeutic molecule, also referred to as effector molecule or as effector module, can e.g. be a peptide, protein, or RNA, which may be selected from shRNA, miRNA, lncRNA, and sgRNA. The therapeutic molecule can have stimulating activity on the immune response, e.g. the effector molecule can be a cytokine, lymphokine, chemokine, or tissue factor. Examples of effector molecules are IL-18, IL-12, IL-12 having a modified sequence, IL15, IL15 having a modified sequence, IL21, IL2, TGF-beta, IL10, IL35, TRAIL (tumor necrosis factor-related apoptosis-inducing ligand) and/or IFN-γ. The vector can be a viral vector comprising flanking LTR or SIN LTR, or flanking inverted terminal repeats (ITRs), or alternatively can be an integrating or episomal non-viral vector, for example with recognition sites for a transposase or recombinase. Preferably, the vector is adapted for integration into the genome of an immune cell. Generally herein, a cognate antigen is also termed target antigen.

In a preferred embodiment of the invention, the viral vector is self-inactivating (SIN) upon integration into the DNA of a recipient cell. The vector has the advantages that the constitutive expression cassette for the second protein, which preferably is a CAR or a TCR, and the inducible expression cassette for the first molecule, which is also related to as effector molecule, in the absence of antigen binding to the CAR or TCR do not influence each other, i.e. the inducible allele only has very low background activity, and that both cassettes are present on a single vector, requiring only a single genetic modification to generate genetically manipulated immune cells. In the presence of antigen binding to the CAR or TCR, respectively, the first molecule is produced, i.e. as an antigen-specific response mediated by the signal transduction of the CAR or TCR.

STATE OF THE ART

Chmielewski and Abken, Cell Reports 3205-3219 (2017), describe genetically manipulated T-cells that on the one hand contain a nucleic acid construct expressing a CAR that can bind to its target antigen through its specific single chain variable fragment (scFv) region, and on the other hand additionally contain a second nucleic acid construct for the cytokine IL-18 that either is inducible upon CAR engagement or constitutively. The additional inducible IL-18 vector construct consists of six NFAT elements followed by a minimal IL-2 promoter. IL-18 is solely expressed after antigen recognition of the CAR. Moreover, they also describe an IL-18 vector construct that constitutively expresses IL-18 independent of antigen recognition and engagement of the CAR construct.

Chmielewski and Abken, Cancer Immunol Immunother 1269-1277 (2012) describe the expression of IL-12 under the control of an NFAT-derived promoter upon binding of a CAR to its antigen, the CAR containing CD3ζ as an intracellular signalling domain. Kailayangiri et al., Oncoimmunology 2017, vol. 6, No. 1, e1250050, describe construction of a CAR that is specific for the antigen GD2.

OBJECT OF THE INVENTION

The objective of the invention is to provide an alternative improved vector, especially a vector containing both a CAR expression cassette and an additional inducible effector module which contains or is an expression cassette encoding RNA or a protein. This shall allow a specific increased expression of the effector molecule after CAR recognition of the cognate antigen. The effector can optionally be IL-18, IL-12 and/or another cytokine that can e.g. help to specifically modify the tumour microenvironment and recruit other immune cells. Preferably, the vector shall be suitable for immunomodulation, e.g. for induction of tolerance or treatment of autoimmunity via e.g. immunomodulatory effector modules like IL10 or TGF-beta. Preferably, the viral vector shall enable the production of a high titer of viral particles which is suitable for clinical applications. Further preferred, the invention shall provide T-cells transduced by the vector, optionally other immune cells transduced by the vector, for use in the treatment of tumour or of virally infected cells. Preferably, the inducible cytokine expression should be tightly linked to the CAR expression and shall not be active without any presence of the target antigen.

DESCRIPTION OF THE INVENTION

The invention achieves the objective by the features of the claims, especially by a nucleic acid construct, herein also generally referred to as a vector or viral vector, and by immune cells containing the nucleic acid construct, especially for use in immune therapy, e.g. for use in the treatment of cancer, or for use in the treatment of autoimmune disease, or for use in the treatment of GvH or HvG. The nucleic acid construct comprises a second expression cassette for constitutive expression of a CAR or a TCR, the binding of which to its target or cognate antigen results in signalling and induces the expression of an effector molecule from a first expression cassette, which is contained on the same nucleic acid construct, and which first expression cassette encodes the effector molecule under the control of a promoter inducible by signalling of the CAR or TCR. Therein, the second molecule is a receptor molecule for a cognate antigen and the first molecule is an effector molecule, and the nucleic acid construct is set up to express the effector molecule upon signalling by the CAR or TCR binding to its cognate antigen. The nucleic acid construct preferably contains integration elements, e.g. viral LTR elements and the vector is e.g. a lentiviral, an alpha ($\alpha$)-retroviral or a gamma ($\gamma$)-retroviral vector. Further, the integration elements can be transposase recognition sites. The nucleic acid construct can optionally be operably linked to a promoter controlling transcription for use in production of viral particles that contain the viral vector, wherein the production is in eukaryotic host cells. The nucleic acid construct, or vector, comprises or consists of at least one expression cassette for a first molecule, herein also referred to as an effector molecule, and at least one expression cassette for a second protein, herein generally represented by a CAR, which expression cassettes are arranged between a 5'LTR and a 3'SIN LTR. In embodiments, in which the at least one expression cassette for an effector molecule and the at least one expression cassette for a CAR are arranged on the same strand of one nucleic acid construct, i.e. forming one vector, more preferred on one common RNA or DNA strand, the expression cassette for an effector molecule is also referred to as a first expression cassette, which is arranged in 5' to the expression cassette for the CAR, which is also referred to as a second expression cassette. It was found that this vector architecture is very important, because another arrangement of these expression cassettes results in readthrough, and can result in unwanted background expression of the effector molecule. An arrangement of both cassettes in antisense orientation leads to RNA interference decreasing vector titers. It was found further that the orientation of the promoter of the first expression cassette and of the coding sequence of the effector molecule in sense-orientation, i.e. sense orientation of the first expression cassette, and sense orientation of the second expression cassette is preferable. Accordingly, it is preferred that the first expression cassette and the second expression cassette are on the same strand, DNA or RNA, and that the first expression cassette is in 5' to the second expression cassette. In contrast to a high induction for sense orientation of both expression cassettes, antisense orientation of the first expression cassette resulted in decreased expression of the sense-oriented expression cassette encoding the CAR. Accordingly, it is preferred that the first expression cassette is arranged directly adjacent to the second expression cassette, wherein both expression cassettes are arranged on one nucleic acid strand, so that both the expression cassettes are arranged in the same direction of transcription, i.e. in sense orientation. Further preferred, a packaging signal ($\Psi$ element) is arranged between the 5' SIN LTR and the first promoter of the first expression cassette Upon integration of the nucleic acid construct, e.g. in an embodiment of a viral vector, into the genome of an immune cell, e.g. by transduction with viral particles containing the vector, the LTR (long terminal repeat) which is arranged in 5' of the at least one first expression cassette and the at least one second expression cassette, is replaced by a copy of the SIN LTR (self-inactivating LTR) that is arranged in 3' to the first and second expression cassettes, e.g. at the 3' terminus of the vector, resulting in a genome-integrated and non-replicating copy of the vector. In the alternative, in the nucleic acid construct, the first and the second expression cassettes may be arranged between two SIN LTR elements, or between two transposase recognition elements, e.g. recognition sites of Sleeping Beauty or PiggyBac transposase or recognition sites for a recombinase. Accordingly, the vector can contain two SIN LTR or two recognition sites for a transposase or recombinase, flanking the first and the second expression cassettes.

The viral vector can be an alpha retroviral SIN vector, a gamma retroviral SIN vector, or a lentiviral SIN vector.

Preferably, a viral packaging signal ($\Psi$ element) is arranged between at least one of the LTR or of the transposase recognition sites and an expression cassette, more preferably, a $\Psi$ element is arranged between a 5' LTR, respectively a 5' transposase recognition site, and the adjacent expression cassette, which preferably is the first expression cassette.

The arrangement of the expression cassettes on one strand, DNA or RNA, with the first expression cassette in 5' to the second expression cassette in the vector has the advantage of being one nucleic acid construct that integrally contains and is sufficient for providing an immune cell with both a CAR or TCR directed against a target antigen, and with an expression cassette encoding an effector molecule, wherein the expression of the effector molecule is only inducible by binding of the CAR or TCR to its target antigen, preferably with significantly lower or preferably no expression of the effector in the absence of target antigen for the CAR or TCR. This All-in-One configuration of the vector enables simplified clinically translatable production processes comprising the alteration, e.g. exchange of the antigen binding domain of the CAR or TCR, and production of only one vector construct, and provides therefore an advantage compared to current combinations of vectors, in which one separate vector construct is used for CAR expression and a second vector construct is used for expression of an effector module. The process produces immune cells for use in the treatment of cells that express the target antigen of the CAR or TCR, respectively. The cells expressing the target antigen can e.g. be tumour cells expressing a tumour antigen as the target antigen, immune cells that cause an autoimmune disease, e.g. immune cells expressing an MHC molecule as the target antigen, which MHC molecule recognizes a self-antigen, or for use in the treatment of HvG disease in transplant patients, wherein the target antigen is e.g. an MHC molecule of the graft. The process can be an in vitro process, using autologous immune cells that originate from the later patient to be treated, and the process can comprise a step of controlling immune cells into which a nucleic acid construct of the invention has been introduced, and selecting immune cells which contain the nucleic acid construct of the invention, preferably selecting immune cells which contain the nucleic acid construct of the invention and excluding cells having tumour markers.

Further, viral particles containing the one nucleic acid construct according to the invention, also termed All-in-One vector, containing or consisting of both the first expression cassette and the second expression cassette, preferably flanked by LTR sites, LTR and SIN-LTR sites, can be produced at high titer in a production cell. For production of viral particles containing the vector, preferably a split-packaging system is used, which e.g. comprises or consists of the vector, a first helper plasmid expressing the viral structural proteins and replication enzymes (gag-pol), and a second helper plasmid for expression of the retroviral envelope protein (env). For lentiviral vector production, an additional rev protein is expressed that binds to the Rev response elements (RRE) and facilitates packaging and the export of transcripts. For production, especially of nucleic acid constructs of the invention which are viral vectors, cultivated human or non-human mammalian cells are preferred. For nucleic acid constructs that contain transposase recognition sites, e.g. ITR, that flank the first expression cassette and the second expression cassette, the nucleic acid construct can be in combination with transposase, e.g. encoded on a nucleic acid section that is arranged on a section that is not flanked by the transposase recognition sites, e.g. ITR, or the transposase can be provided as an addition plasmid. The region encoding the transposase preferably is an expression cassette for transposase, having a promoter in 5' to the transposase encoding region and a poly-adenylation signal in 3' to the transposase encoding region. For genetic manipulation of an immune cell, both the nucleic acid construct containing the first expression cassette and the second expression cassette and the region encoding the transposase are transfected into the immune cell.

Furthermore, the vector has the advantage that once the target antigen is present, the binding of the CAR to its target antigen directly results in the induction of the expression of the effector molecule from the first expression cassette, whereas in the absence of the target antigen a significantly lower or no expression of the effector molecule occurs. This shows that the vector is set up to express the effector molecule encoded by the first expression cassette essentially only in response to the presence of the target antigen, for which the CAR is specific. This behaviour of the vector is highly desirable, because the effector molecule is only produced by cells, preferably immune cells, containing the vector in the presence, i.e. in contact with the target antigen, and hence the effector is produced only in the vicinity of e.g. cells bearing the target antigen. Accordingly, the vector, respectively immune cells containing the vector, are suitable for use in the medical treatment of cells expressing the target antigen, and especially of solid tumours, of autoimmune disease, or for providing tolerance, by generating a cellular immune response directed against cells bearing the target antigen in combination with secreting an effector molecule in the vicinity only of cells bearing the target antigen. For use in the treatment of a tumour, preferably of a solid tumour, the target antigen can be a tumour antigen, and the CAR is specific for the tumour antigen. For use in the treatment of an autoimmune disease, the target antigen can be the antigen against which the autoimmune disease is directed, and the CAR is specific for the target antigen.

Due to the localized cytokine secretion in the presence of the target antigen only, e.g. at the site of inflammation, e.g. IL-12 or IL-18 as effector molecule, this vector has the advantage to shape the tumour microenvironment by recruiting other immune cells, e.g. macrophages, dendritic cells or NK cells, and to therefore improve the proinflammatory immune and anti-tumour responses. Based on the modular architecture of the vector, it is also possible to express other effector molecules, e.g. other cytokines, e.g. IL-15, that are known to prolong the survival and persistence of the immune cells and thus directly affect the immune response. In this regard, the vector can be used to influence the immune response in an anti-inflammatory manner, expressing as effector molecule e.g. IL10 and/or TGF-beta, e.g. for use in the treatment of GvH disease or in HvG disease in order to prolong transplant survival, or for use in the treatment of an autoimmune disease.

As immune cells containing the vector are set up to secrete the effector encoded by the first expression cassette only in the presence of the target antigen of the CAR, it was found that essentially no systemic secretion of the effector molecule occurs, avoiding adverse systemic side effects of the effector. In detail, the constitutively expressed CAR of the second expression cassette activates expression of the effector molecule encoded by the inducible first expression cassette through its intracytoplasmatic effector domain, and therefore activates the secretion of the immune effector molecule directly in the tissue bearing the target antigen recognized by the CAR, e.g. within the tumour, and due to this localized expression of effector molecules, which e.g. induce inflammation, possible adverse systemic side effects are minimized or avoided. This direct functional link between the CAR binding its target antigen and expression of the effector molecule provides an improved control of both the genetically modified target cells and the inducible secretion of the effector molecule and represents an additional advantage of the all-in-one vector system. Moreover, the use of just one vector reduces the risk of insertional mutagenesis and of cooperative oncogenesis. Finally, a reduction of steps for genetic manipulation of immune cells to a transduction with just a single All-in-One vector viral particles is more practical and e.g. allows use of clinical processes for producing for effector-enhanced CAR/TCR T-cells, NK cells and other immune cells.

The effector molecule can be selected e.g. from IL-12, IL-15, IL-18, IL10, TGF-beta, IL-2, IL-21 and IFN-γ. Preferably, IL-12 is encoded by SEQ ID NO: 4, which in human immune cells has been found to be expressed more efficiently than the wild-type coding sequence, and IL-18 is preferably encoded by SEQ ID NO: 6, which in human immune cells has been found to be expressed more efficiently than the wild-type coding sequence. For IL12, the chains are preferably directly fused to one another.

The vector can be contained in various immune cells, e.g. T-cells, preferably primary T cells (also including primary regulatory T cells), primary NK cells, primary NKT cells, macrophages, NK92 cells and dendritic cells. The immune cell containing the vector, respectively the immune cell which is genetically manipulated to contain the vector, can be a T-cell, a primary NKT-cell, a NK92 cell, a macrophage, or a dendritic cell, preferably a primary T-cell. Preferably, for the first promoter being the NκBenhsyn promoter, the immune cell is a primary NK cell or a NK92 cell. More detailed, the immune cell originates from the patient who is the later recipient of the immune cell containing the vector.

Alternatively, immune cells with downregulated MHC and/or downregulated TCR expression, which are e.g. obtainable as pre-fabricated cells, can be genetically manipulated to contain the vector.

In embodiments, in which immune cell is a NK cell, especially when the vector is an alpha-retroviral or lentiviral vector, the first promoter preferably is the NFκBenhsyn promoter as a stronger promoter, or the first promoter is the NFAT promoter as a weaker promoter.

The CAR, from N-terminus to C-terminus, generally comprises or consists of an antigen binding domain—optionally a hinge—transmembrane domain—intracytoplasmatic effector domain, wherein the binding domain is a target antigen-binding domain, e.g. a scFv, a nanobody, a darpin, a ligand, or the extracellular portion of a T-cell receptor or of a B-cell receptor. The intracytoplasmatic effector domain preferably comprises or consists of the CD3zeta (CD3ζ) domain or e.g. the FceRI g-chain, with or without at least one co-stimulating domain, e.g. selected from the CD28 domain, the 41BB domain and the CD27 domain, preferably the intracytoplasmatic effector domain from N-terminus to C-terminus consists of the CD3t domain and an adjacent CD28 domain. In the presence of target antigen binding to the binding domain, at least a portion of the intracytoplasmatic effector domain, e.g. the CD3ζ domain, dimerizes. The co-stimulating domain may enhance the activating effect of the CAR when binding target antigen.

In an alternative to CD3ζ, e.g. for NK cells, the intracytoplasmatic effector domain of the CAR can be the intracellular effector domain of DAP12 or DAP10. In the preferred embodiments, the CAR, which can be a T-cell receptor (TCR), as its intracellular signalling domain comprises a CD3ζ domain, which directly or mediated or assisted by transcription factors of eukaryotic cells, activates promoters containing an NFAT element or an NFκBenhsyn element, especially a promoter of one of SEQ ID NO: 1, SEQ ID NO: 2, SEQ ID NO: 3, and SEQ ID NO: 31.

For production of viral particles containing the nucleic acid construct containing or consisting of both the first expression cassette and the second expression cassette, in a production cell the nucleic acid construct preferably is under the control of a promoter selected from the group of the Cytomegalovirus (CMV) promoter (SEQ ID NO: 12), the Rous sarcoma virus (RSV) promoter (SEQ ID NO: 13), or the HIV U3 promoter (SEQ ID NO: 14). In case of gammaretroviral vectors also MLV-derived promoters (e.g. the SFFV or MPSV promoter) may be used. The vector has the advantage for clinical application that it can be produced at high titers that are sufficient for the generation of genetically modified T cells and other immune cells, e.g. NK cells and NK T cells, under good manufacturing practice (GMP) conditions. It was found that by the exchange of the RSV promoter to the CMV promoter within the 5' LTR region the titer of viral particles containing the vector in producer cells was increased to the 10-fold.

According to the invention, the first expression cassette from 5' to 3' comprises or consists of a first promoter containing a TATA box, e.g. in the minimal IL2 promoter or enhanced element, a coding sequence encoding the effector molecule, and optionally in 3' adjacent to the coding sequence a terminator or preferably is devoid of a terminator. Preferably, these elements are arranged directly adjacent to one another. The first promoter is inducible by the host cell containing the vector and is induced by NFAT (nuclear factor of activated T-cells) and preferably has SEQ ID NO: 1, also referred to as NFATenhsyn promoter, because it has shown enhanced induction, e.g. effecting higher expression of the coding sequence than a known wild-type NFAT promoter, and it is a synthetic promoter element. As an alternative, the first promoter can have SEQ ID NO: 2 (NFATmIL2) and consists of an minimal IL2 promoter including a TATA box and fused to six NFAT response elements, or SEQ ID NO: 3 (NfκBenhsyn), where the NFAT response elements were exchanged for two NFκB response elements, or SEQ ID NO: 31. It was found that the first promoter having

```
(NFATenhsyn)
                                        SEQ ID NO: 1
(TGGAGGAAAAACTGTTTCATACAGAAGGCGTGGAGGAAAAACTGTTTCA

TACAGAAGGCGTGGAGGAAAAACTGTTTCATACAGAAGGCGTGGAGGAAA

AACTGTTTCATACAGAAGGCGTGGAGGAAAAACTGTTTCATACAGAAGGC

GTGGAGGAAAAACTGTTTCATACAGAAGGCGTCTGCAGGAGACTCTAGAG

GGTATATAATGGTTTAAACTTAAGCTTGGTACCGGGCCCCCGAAG), (NFATmIL2)
                                        SEQ ID NO: 2
(GATATCGAATTAGGAGGAAAAACTGTTTCATACAGAAGGCGTCAATTAG

GAGGAAAAACTGTTTCATACAGAAGGCGTCAATTAGGAGGAAAAACTGTT
```

```
                    -continued
TCATACAGAAGGCGTCAATTGGTCCCATCGAATTAGGAGGAAAAACTGTT

TCATACAGAAGGCGTCAATTAGGAGGAAAAACTGTTTCATACAGAAGGCG

TCAATTAGGAGGAAAAACTGTTTCATACAGAAGGCGTCAATTGGTCCCGG

GACATTTTGACACCCCCATAATATTTTTCCAGAATTAACAGTATAAATTG

CATCTCTTGTTCAAGAGTTCCCTATCACTCTCTTTAATCACTACTCACAG

TAACCTCAACTCCTG),
or (NfκBenhsyn)
                                        SEQ ID NO: 3
(CTCGAGGGGAATTTCCGGGGACTTTCCGGGAATTTCCGGGGACTTTCCG

GGAATTTCCGGGAATTTCCGGGGACTTTCCGGGAATTTCCGGGGACTTTC

CGGGAATTTCCCTGCAGGAGACTCTAGAGGGTATATAATGGTTTAAACTT

AAGCTTGGTACCGGGCCCCCGAAG),
or (nucleotides 4178 . . . 4400 of SEQ ID NO: 32)
(NfκBmIL2)
                                        SEQ ID NO: 31
GGGAATTTCCGGGGACTTTCCGGGAATTTCCGGGGACTTTCCGGGAATTT

CCGGGAATTTCCGGGGACTTTCCGGGAATTTCCGGGGACTTTCCGGGAAT

TTCCCCCGGGACATTTTGACACCCCCATAATATTTTTCCAGAATTAACAG

TATAAATTGCATCTCTTGTTCAAGAGTTCCCTATCACTCTCTTTAATCAC

TACTCACAGTAACCTCAACTCCTG
``` results in a high expression of the effector, whose expression is only induced in the presence of the target antigen of the CAR. It is generally preferred that in 3' of the first promoter having SEQ ID NO: 1 and in 5' to the coding sequence, a TATA box is arranged, which TATA box preferably has sequence 5'—TATA (A/T) A (A/T)—3' and respectively a nucleotide sequence of nucleotides No. 202-208 of SEQ ID NO: 1 or a nucleotide sequence of nucleotides 291-297 of SEQ ID NO: 2 or a sequence of nucleotides 131-137 of SEQ ID NO: 3. In embodiments, in which the first promoter has SEQ ID NO: 2 or SEQ ID NO: 3, the coding sequence can be arranged directly adjacent to the first promoter. Preferably, the first promoter is selected from the group comprising or consisting of SEQ ID NO: 1, SEQ ID NO: 2, SEQ ID NO: 3, and SEQ ID NO: 31.

The second expression cassette from 5' to 3' comprises or consists of a second promoter, which is a constitutive promoter, a coding sequence encoding a CAR, optionally a WPRE (woodchuck hepatitis virus posttranscriptional regulatory element, preferably SEQ ID NO: 15), optionally in 3' adjacent to the WPRE a terminator or preferably no terminator. Preferably, these elements are arranged directly adjacent one another. Preferably, the constitutive second promoter is a PGK (phosphoglycerokinase) promoter, e.g. having a nucleotide sequence of nucleotides 5158 . . . 5673 of SEQ ID NO: 8.

Preferably, a polyadenylation signal is arranged in 3' to the second expression cassette. A poly-adenylation signal can e.g. be contained in the 3' LTR, preferably a 3' SIN LTR, e.g. in its R region with U5. Generally preferred, there is no poly-adenylation signal between the first expression cassette and the second expression cassette, and/or no poly-adenylation signal between the second expression cassette and the 3' SIN LTR. It has been found that a poly-adenylation signal arranged between the flanking LTRs results in a decrease in titer of viral particles in production cells.

Accordingly, it is generally preferable for viral vectors of the invention, e.g. nucleic acid constructs containing LTR and SIN LTR flanking the first and second expression cassettes, that between flanking LTR and SIN LTR, between flanking ITRs, the nucleic acid construct is devoid of a poly-adenylation signal. In embodiments containing transposase recognition sites flanking the first and second expression cassettes, it is preferred that in 5' to the 3'ITR, e.g. directly in 3' to the second expression cassette, there is arranged an additional poly-adenylation signal.

The PGK promoter is the preferred promoter for the second expression cassette encoding the CAR, because the PGK promoter was found not to activate neighbouring genes, i.e. does not have a cis-activating effect when the vector is integrated into the genome of an immune cell. Similarly, for example the EF-1 alpha short (EFS, SEQ ID NO: 11) promoter, when arranged in the second expression cassette, was found also not to induce transcription from the first expression cassette encoding the effector. In contrast to PGK and EFS promoters, the spleen focus forming virus (SFFV, SEQ ID NO: 10) U3 promoter when used as the second promoter for the CAR showed higher transactivation of the first expression cassette. Accordingly, promoters with weak transactivation potential, like the PGK promoter and the EFS promoter, are preferred over a strong promoter with transactivation potential, e.g. SFFV.

Figure 4:
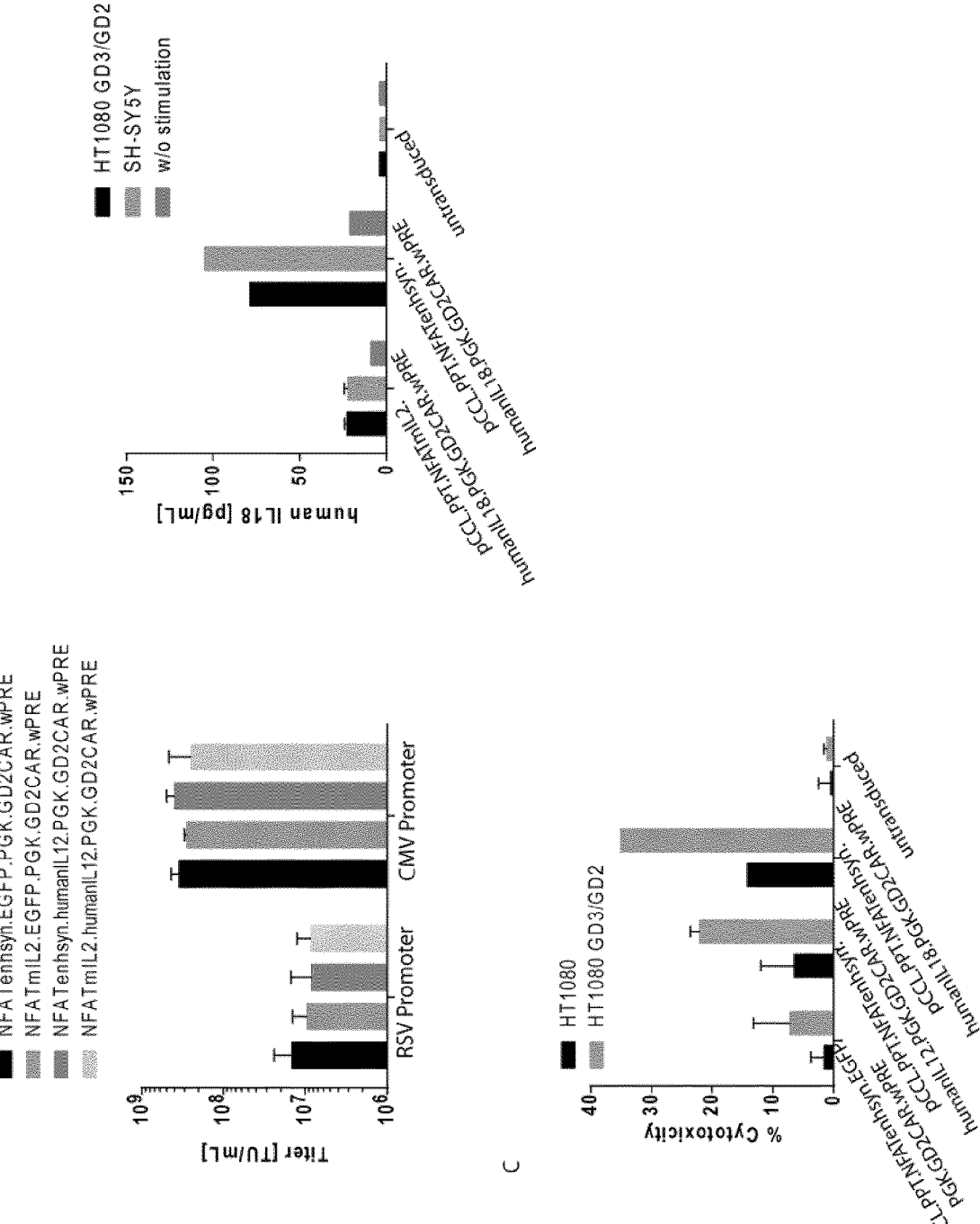
Figure 5:
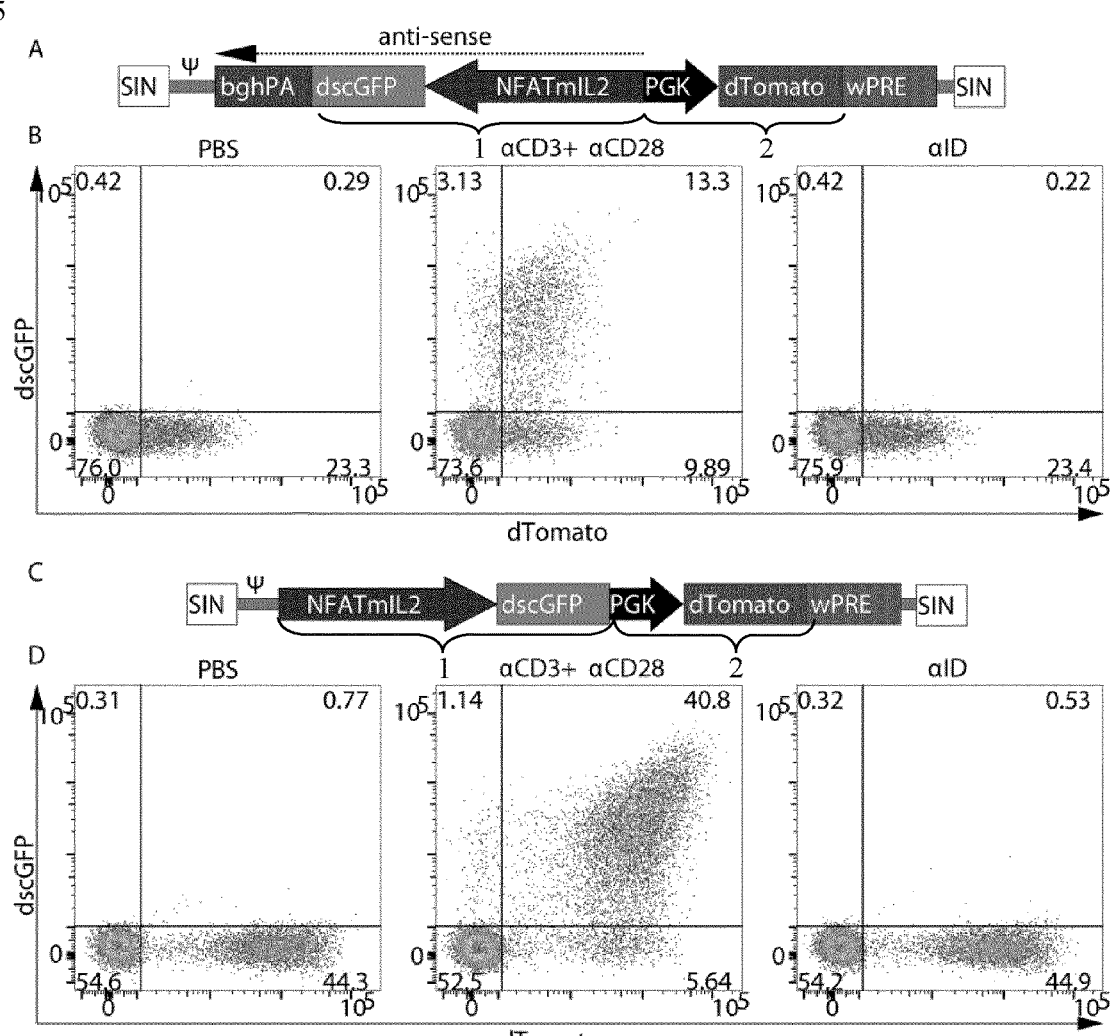
Figure 5:
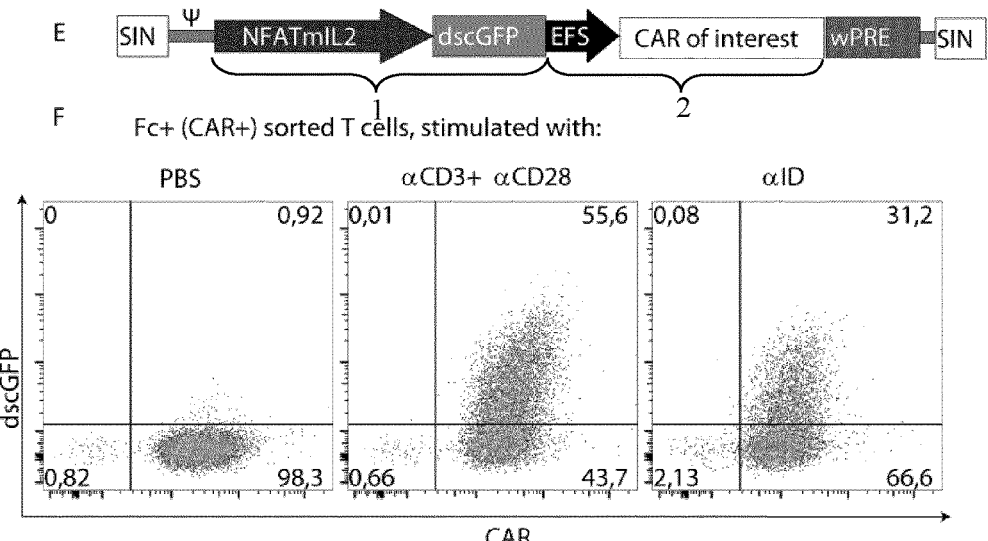
Figure 6:
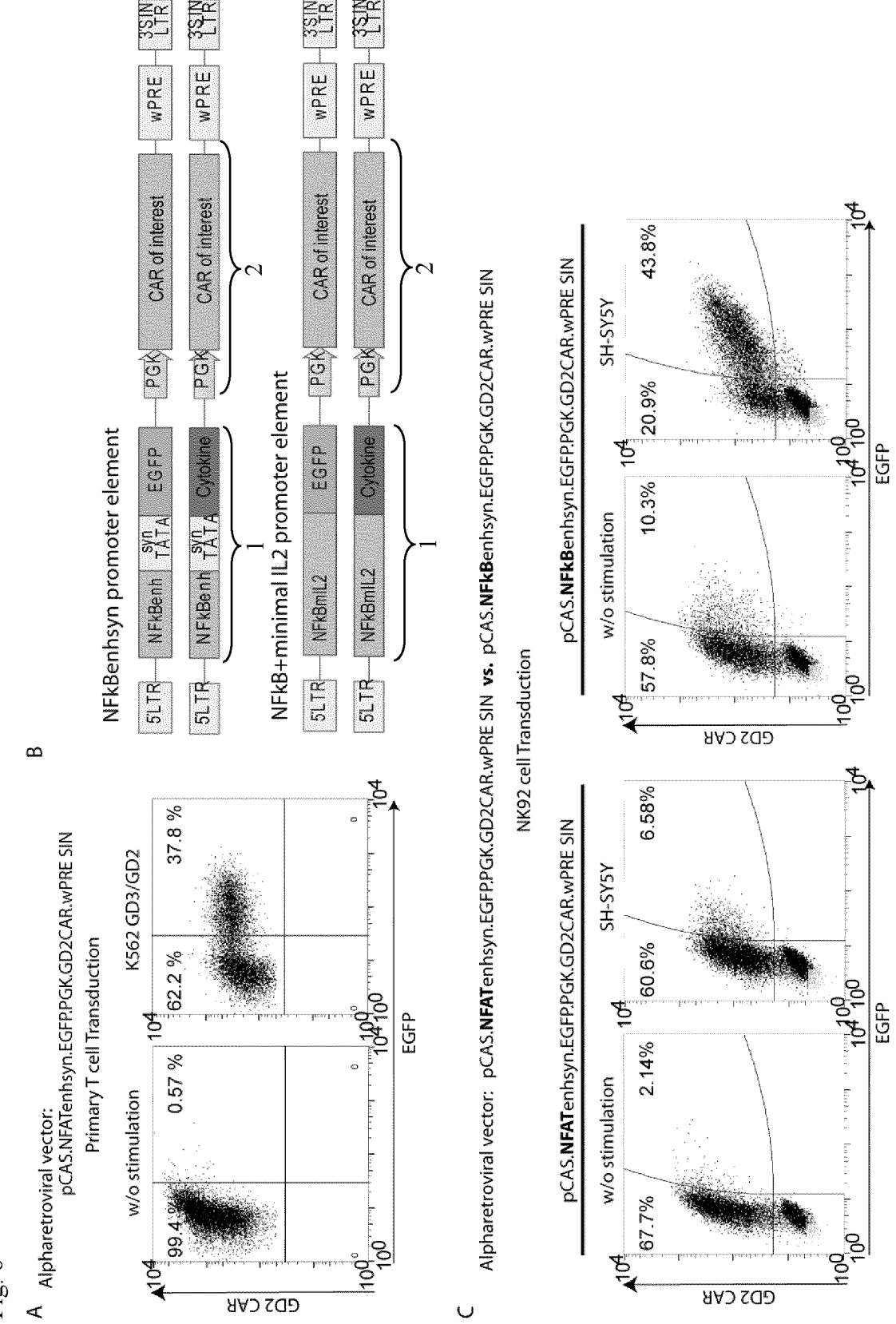
Figure 7:
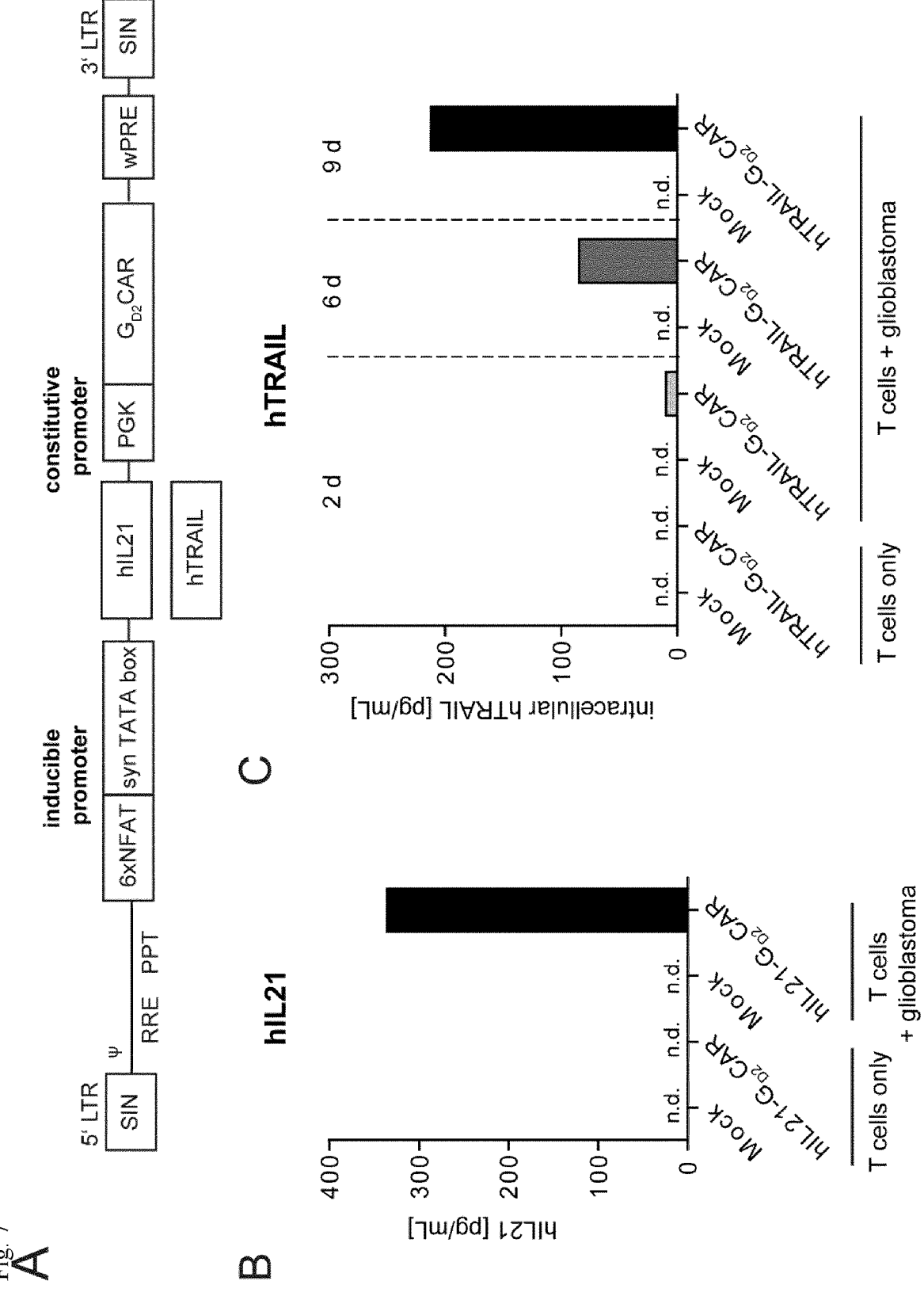

The invention is now described in greater detail and with reference to the figures, wherein FIG. 1 shows an embodiment of the arrangement of the elements of a viral vector according to the invention, FIG. 2 shows an embodiment of the arrangement of the elements of a viral vector according to the invention, FIG. 3 shows expression levels from vectors in T-cells after CAR-specific stimulation, FIG. 4A shows results for production of viral particles containing a vector of the invention, FIG. 4B shows expression levels of an effector from T cells containing the vector after CAR-specific stimulation, FIG. 4C shows cytotoxicity results for immune cells (T cells) containing the vector, FIG. 5 in A, C, and E shows schematic representations of vectors, and in B, D, and F shows FACS results for expression of the effector from vectors without induction, with induction, and with unspecific induction, FIG. 6A shows expression of the effector in T cells transduced with alpharetroviral all-in-one vectors after CAR-specific stimulation, and FIG. 6B shows an embodiment of the arrangement of the elements of a viral vector after exchange of the NFAT element to the NFκB element, FIG. 6C shows the comparison between the NFATenhsyn and NFκBenhsyn promoters in alpharetrovirally transduced NK92 cells and its effector induction after CAR-specific stimulation, FIG. 7A schematically shows two embodiments of a viral vector according to the invention encoding hIL21 and hTRAIL as the effector molecules, respectively, FIG. 7B shows secretion levels of hIL21 and FIG. 7C shows secretion levels of hTRAIL, resp., of primary T-cells containing a vector shown in FIG. 7A with or without contact with glioblastoma cells that express the target antigen for the CAR, FIGS. 8A, 8B, 8C and 8E show bar graphs of expression of a representative effector molecule for different first promoters from immune cells harbouring the vector and stimulated by presence of the target antigen of the CAR, FIG. 8D shows FACS results for EGFP as a representative effector molecule under control of different first promoters without (w/o) and with stimulation by cells expressing the target antigen GD2 for the GD2-specific CAR.

In the Figures, the exemplary CAR, which is specific for GD2, is also designated as GD2CAR. FIG. 1 and FIG. 2 schematically show exemplary nucleic acid constructs of a first expression cassette 1 and a second expression cassette 2 of the invention between a 5' LTR and a 3' SIN LTR. As generally preferred, the first expression cassette 1 is arranged in 5' of the second expression cassette 2, and both the first and the second expression cassettes 1, 2 are on the same strand of one nucleic acid construct.

FIG. 1 shows two embodiments, in which the first expression cassette 1 consists of a promoter of SEQ ID NO: 1 (NFATenhsyn), a TATA box of nucleotides 202..208 of SEQ ID NO: 1, and a coding sequence for the effector, represented by eGFP (EGFP) or a cytokine (Cytokine), and the second expression cassette 2 consists of the PGK promoter (PGK), a coding sequence for a CAR having an antigen-binding domain (CAR of interest), and a WPRE (wPRE). In two further embodiments shown in FIG. 2, the first expression cassette 1 consists of the NFATmIL2 promoter (NFATmIL2) of SEQ ID NO: 2 directly adjoined by a coding sequence for the effector, exemplified by EGFP or a cytokine (Cytokine). The second expression cassette 2 is the same as in the other two embodiments. Neither the first expression cassette 1, nor the second expression cassette 2 contains an internal terminator in 3' of the coding sequence. Generally, the 3'LTR, more specifically the R region with U5, can serve as the polyadenylation signal.

EXAMPLE 1

Expression of Effector and of CAR from Lentiviral Vectors

As a representative for an effector, the coding sequence for eGFP (enhanced green fluorescent protein, EGFP) or the coding sequence for IL-12 (IL12) was contained in a first expression cassette under the control of the NFATenhsyn promoter (NFATenhsyn) having SEQ ID NO: 1 or under the control of the NFATmIL2 promoter having SEQ ID NO: 2, and the second expression cassette, arranged in 3' to the first expression cassette, contained a GD2-specific CAR (GD2CAR) under the control of the PGK promoter (PGK, nucleotides 5158..5673 of SEQ ID NO: 8), followed by the WPRE (SEQ ID NO: 15, PRE). A GD2-specific CAR (GD2CAR, e.g. as described by Kailayangiri et al., Onco-immunology 2017) contained, from its N-terminus to its C-terminus, an antigen-binding domain specific for the exemplary target antigen Ganglioside 2 (GD2), a hinge, a transmembrane domain, a 4-1BB signalling domain fused to a CD3ζ domain. The first and the second expression cassettes were flanked by a 5' LTR and a 3' SIN LTR.

The vector encoding eGFP (EGFP) under the control of the NFATenhsyn promoter is designated pCCL.PPT.NFATenhsyn.EGFP.PGK.CAR.wPRE (SEQ ID NO: 8), wherein the CAR was a GD2-specific CAR.

The vector which in the alternative to the NFATenhsyn promoter in the first expression cassette contained the promoter having SEQ ID NO: 2 (NFATmIL2) in 5' to the effector (eGFP) encoding portion was designated pCCL.PPT.NFATmIL2.EGFP.PGK.CAR.wPRE (SEQ ID NO: 20), wherein the CAR was a GD2-specific CAR. An alpha retroviral vector construct having the NFκBmIL2 promoter in the first expression cassette is shown in SEQ ID NO: 26.

As a further example, a vector having the same elements except for the first expression cassette encoding human IL-12 (IL12human) instead of eGFP was used, this vector was designated pCCL.PPT.NFATenhsyn.humanIL12.PGK.CAR.wPRE (SEQ ID NO: 16) for the first expression cassette containing the NFATenhsyn promoter, wherein the CAR was a GD2-specific CAR. A vector containing the promoter NFATmIL2 of SEQ ID NO: 2 for the first expression cassette was designated pCCL.PPT.NFATmIL2.humanIL12.PGK.CAR.wPRE (SEQ ID NO: 22), wherein the CAR was a GD2-specific CAR. A vector containing the promoter NFκBmIL2 of SEQ ID NO: 31 for the first expression cassette was designated pCCL.PPT.NFκBmIL2.EGFP.PGK.CAR.WPRE (SEQ ID NO: 32), wherein the CAR was the GD2-specific CAR. Herein, pCCL designates a lentiviral transfer vector containing chimeric CMV-HIV 5′ LTRs. In pCCL, the enhancer and promoter of CMV were joined to the R region of HIV-1. The vector constructs designated pCAS are alpha-retroviral vectors having alpha-retroviral LTRs.

For transduction of lentiviral, gamma- or alpha-retroviral particles containing the vector, primary human T-cells were isolated from human peripheral blood mononuclear cells (PBMC) from buffy coats. The T cells were activated with αCD3/αCD28 antibodies before transduction and were then transduced with the viral particles using RetroNectin (available from TaKaRa) as an enhancer of transduction.

The primary human T-cells containing one of the vectors were cultivated in RPMI medium containing 10% FCS (fetal calf serum), 1% P/S (penicillin-streptomycin) and IL-2 for approximately 11 days , followed by addition of cells expressing the target antigen, GD2HT1080 cells (HT1080 GD2), or K562 cells (K562 GD2), or the neuroblastoma cell line SH-SY5Y, which naturally expresses GD2.

FIG. 3A shows analytical results for the expression of EGFP from the first expression cassette measured after 24 h of co-cultivation of the primary T-cells containing one of these vectors either without any additional target antigen-bearing cell line (w/o stimulation, left col.), with HT1080 GD2-bearing cells (middle col.), or with SH-SY5Y cells (right col.). On the example of eGFP as a reporter effector, these results show that the effector of the first expression cassette is essentially only expressed by the primary T-cells in the presence of cells bearing the target antigen (GD2) for the CAR, whereas in the absence of cells bearing the target antigen, essentially no expression of the effector occurs from the first expression cassette, clarifying the CAR-specific and tight induction of the effector molecule FIG. 3B from left to right shows analytical results for the expression of human IL-12 from the first expression cassette measured after 24 h of co-cultivation of the primary T-cells containing one of these vectors either without any additional target antigen-bearing cell lines (w/o stimulation, $1^{st}$ col.), with SH-SY5Y cells ($2^{nd}$ col.), with HT1080 GD2 cells ($3^{rd}$ col.), or with K562 cells that express GD2 ($4^{th}$ col).

Further, these results show that in primary T-cells that were used as exemplary immune cells the CAR is expressed sufficiently to activate the first promoter of the first expression cassette in the presence of cells bearing its target antigen.

FIG. 3B further depicts the results for primary T-cells that did not contain the vector for comparison (untransduced), showing that the synthesis of the effector is caused by the presence of the vector in the immune cells and that there are no additional side effects or unspecific cytokine secretion in primary T cells.

For production of lentiviral particles containing the vector, the vector was cloned for transcription under the control of the RSV promoter or the CMV promoter. Viral particles were produced in 293T cells with the vector under the control of the CMV promoter or the RSV promoter and containing helper plasmids encoding VSVg pseudotype coat proteins.

FIG. 4A depicts the results of the determination of the titer of viral particles in HT1080 cells, showing that the vectors, from left to right,
NFATenhsyn.EGFP.PGK.CAR.wPRE,
NFATmIL2.EGFP.PGK.CAR.wPRE,
NFATenhsyn.humanIL12.PGK.CAR.wPRE (containing the IL12 encoding sequence in the first expression cassette), and
NFATmIL2.humanIL12.PGK.CAR.wPRE are produced at significantly higher titer under the control of the CMV promoter for transcription in production cells than under control of the RSV promoter.

Expression of the effector, represented by human IL-18, was tested in primary T-cells transduced with one of the vectors pCCL.PPT.NFATmIL2.humanIL18.PGK.CAR.PRE containing a human IL-18 encoding sequence under the control of the promoter NFATmIL2 of SEQ ID NO: 2, pCCL.PPT.NFATenhsyn.humanIL18.PGK.CAR.PRE (SEQ ID NO: 18) containing the human IL-18 encoding sequence under the control of the promoter NFATenhsyn of SEQ ID NO: 1, wherein the CAR was a GD2-specific CAR, and in T-cells that were not genetically manipulated (untransduced, control).

Stimulation was done by co-incubation of the genetically manipulated primary T-cells or non-transduced primary T-cells as control in a 10:1 effector to target ratio of primary T-cells with target cells expressing the target antigen GD2, namely HT1080 cells expressing GD2 (HT1080 GD3/GD2, FIG. 4B, left col.) or SH-SY5Y cells (FIG. 4B, center col.), or without stimulation (w/o stimulation, FIG. 4B, right col.). These results show that in comparison to control cells (untransduced), essentially only cells containing a vector according to the invention effectively express IL-18, and that the NFATenhsyn promoter generates a significantly higher expression of the effector from the first expression cassette than the promoter NFATmIL2.

FIG. 4C depicts the analytical results of lactate dehydrogenase measurements (LDH) as an indicator for cytotoxicity of primary T-cells that were lentivirally transduced to contain a vector of the invention after co-cultivation with HT1080 cells that do not express GD2 (HT1080, negative control, left columns), or with GD2-expressing HT1080 cells (HT1080 GD3/GD2, right columns) in a target-effector ratio of 10:1 (primary T-cells to HT1080 or HT1080 GD3/GD2 cells). As a control, primary T-cells without genetic manipulation (untransduced) were used. The results show that in the presence of cells without target antigen, and especially in the presence of cells bearing the target antigen, the immune cells containing a vector according to the invention exhibit a significantly higher cytotoxicity over primary T-cells without the vector (untransduced).

EXAMPLE 2

Regulatory Elements of Gamma Retroviral Vector

For embodiments, regulatory elements of the vector, especially the second promoter and the arrangement of the first and second expression cassettes in relation to one another were tested in the embodiment of a gamma retroviral vector.

As an embodiment there was used the arrangement of the first expression cassette and of the second expression cassette such that the first and the second expression cassettes are arranged on opposite strands of a double stranded nucleic acid construct with their 5'-ends adjacent one another and their 3'-ends distant from one another (antisense orientation), and the expression cassettes are between two SIN LTR (SIN). The first expression cassette from 5' to 3' consists of the NFATmIL2 representing the first promoter, dscGFP (destabilized copGFP) as a representative of the effector. The second expression cassette from 5' to 3' consists of the PGK promoter, the dTomato as a reporter representing the CAR, and a WPRE. This embodiment is schematically shown in FIG. 5A.

FIG. 5C shows the generally preferred arrangement of the first expression cassette in 5' of the second expression cassette, wherein, further preferred, the first expression cassette is arranged directly adjacent to the second expression cassette, wherein both expression cassettes are arranged on one nucleic acid strand, so that both the expression cassettes are arranged in the same direction of transcription (sense orientation). A packaging signal (Ψ element) is arranged between the 5' SIN LTR and the first promoter of the first expression cassette.

FIG. 5E shows the structure of an embodiment of the vector, in which the second expression cassette as the second promoter contains the EFS promoter to control expression of the CAR encoding sequence, in 3' to which a WPRE is adjacent.

The γ-retroviral vectors were transduced into primary T-cells, which after cultivation were stimulated with phosphate buffered saline (PBS, negative control), T-cell activating antibodies anti-CD3 and anti-CD28 (αCD3+αCD28), or with a non-specific antibody (irrelevant antibody, αID (anti-idiotype antibody).

FIGS. 5B and 5D, 5F show FACS (fluorescence activated flow cytometric cell sorting) results of the expression of dsGFP from the first expression cassette after stimulation and of dTomato representing the CAR from the second expression cassette as indicated. FIGS. 5B and 5D show that the arrangement of the first expression cassette and adjacent thereto in 3' the second expression cassette, both on the same nucleic acid strand (FIG. 5C), upon effective stimulation by anti-CD3 and anti-CD28 results in a higher expression from both the first and the second expression cassettes than arrangement of the first expression cassette in antisense orientation and the second expression cassette on opposite strands of a double-stranded nucleic acid construct, especially with the direction of transcription pointing away from one another.

Further, FIGS. 5B and 5D show that mock stimulation by PBS or stimulation with an irrelevant anti-idiotype antibody (αID) results in no dscGFP expression. This shows that the nucleic acid constructs are set to specifically express the effector from the first expression cassette only upon activation of the immune cell by presence of the target antigen of the CAR. Further, these results show that the inducible promoter as the first promoter is only active upon specific activation of the immune cell.

FIG. 5F shows FACS results for primary T-cells transduced with the vector of FIG. 5E. Here, the dTomato-WPRE construct (FIG. 5C) was exchanged by a CAR expression cassette. The CAR (CAR of interest, anti-CEA (carcinoembryonic antigen)-CAR) was detected by a labelled specific antibody against the Hinge-Region of the CAR (anti-F(ab)$_2$ αIgG1-PE antibody). FIG. 5F indicates that T cells transduced with the vector displayed no dscGFP expression when stimulated with PBS, but responded with induction of dscGFP after culture with activating aCD3 antibody and aCD28 antibody. Moreover, transduced T cells induced dscGFP expression after binding to CAR-crosslinking αID antibody, providing proof that CAR-mediated signaling activates the NFAT-responsive promoter in the vector, indicating that the vector is also suitable for γ-retroviral vectors and for the EFS promoter.

EXAMPLE 3

Regulatory Elements of Alpha Retroviral Vector

Regulatory elements of the vector, especially the first promoter and the arrangement of the first and second expression cassettes in relation to one another were tested in the embodiment of an alpha retroviral vector.

Primary T-cells were transduced with viral particles containing one of the exemplary vectors transferred to the alpha retroviral vector, followed by co-cultivation with GD2-expressing K562 cells for 24 h (FIG. 6A).

The vector containing the coding sequence for eGFP as a representative of the effector under the control of the NFATenhsyn promoter was designated pCAS.NFATenhsyn.EGFP.PGK.GD2CAR.wPRE SIN, and expression from this vector was analysed by FACS, using an anti-GD2CAR-PE antibody for detection of the CAR. FIG. 6A presents the FACS results without stimulation (w/o stimulation), and with stimulation (K562 GD3/GD2), showing that without stimulation and also in the presence of stimulation, the CAR is expressed, and that only in the presence of the target antigen GD2 for stimulation the effector, represented by eGFP (EGFP), is upregulated.

EXAMPLE 4

Embodiments of the Vector (First Expression Cassette)

The following exemplary vectors show that the vector is suitable for introduction into other immune cells besides T cells, e.g. NK92 (FIG. 6C), primary NK and NK T cells and macrophages. The modular structure of the vector allows an adjustment to the specific properties and signaling pathways of the immune cells. An improvement of the first expression cassette can be obtained e.g. by the exchange of the promoter controlling the coding sequence of the effector module. The exchange of the NFAT promoter allele for the nuclear factor kappa-light-chain-enhancer of activated B-cells (NFκBenhsyn) promoter element (SEQ ID NO: 3) was found to result in an increased CAR-mediated induction of the effector, e.g. represented by eGFP, in NK92 cells (FIGS. 6B and C) and primary NK cells.

FIG. 6B schematically shows exemplary vector constructs that on one nucleic acid strand between a 5' LTR and a 3' SIN LTR from 5' to 3' contain a first expression cassette consisting of a first promoter, which has SEQ ID NO: 3 (NFκBenhsyn) or nucleotides 4178..4281 of SEQ ID NO: 32 (NFκBmIL2) each including a TATA box, and a coding sequence for the effector which is represented by eGFP (EGFP) or a cytokine (Cytokine), and a second expression cassette consisting of a constitutive second promoter, herein the PGK promoter having the nucleotide sequence of nucleotides No. 5158..5673 of SEQ ID NO: 8, a coding sequence for a CAR of interest and the WPRE having SEQ ID NO: 15 (wPRE).

FIG. 6C shows the comparison between the different tested promoter elements (respectively NFATenhsyn and NFκBenhsyn) in the first expression cassette in alpha retrovirally transduced NK92 cells (pCAS.NFATenhsyn-.EGFP.PGK.CAR.PRE SIN (SEQ ID NO: 26), wherein the CAR was a GD2-specific CAR, or pCAS.NFκBenhsyn.EGFP.PGK. CAR.PRE SIN (SEQ ID NO: 28). The FACS results were depicted for pCAS.N-FATenhsyn.EGFP.PGK. CAR.PRE SIN in the two left graphs, and for pCAS.NFκBenhsyn.EGFP.PGK.CAR.PRE SIN in the two right graphs. The results show that the CAR is expressed from all the vector embodiments tested, and that in the absence of stimulation (w/o stimulation) essentially no effector (EGFP) is produced, whereas in the presence of the stimulating target antigen, represented by the GD2-expressing SH-SY5Y neuroblastoma cells, the representative effector eGFP is produced. This shows that the NFκBenhsyn promoter as the first promoter results in a stronger and more prominent expression of the effector encoded by the first expression cassette. The exchange of the NFAT-inducible element to the NFκB-inducible element resulted in a better and prominent upregulation of eGFP in NK92 cells indicating the adapted and improved signal transduction in these cells due to the vector according to the invention. A lentiviral vector containing the expression cassettes NFκBenhsyn.EGFP.PGK.CAR is shown in SEQ ID NO: 24.

EXAMPLE 5

Embodiments of the Vector Expressing hIL21 or hTRAIL

Exemplary embodiments of the vector, which in the first expression cassette encode human interleukin 21 (hIL21) or human tumor necrosis factor-related apoptosis-inducing ligand (hTRAIL) under the control of a CAR inducible promoter, with a second expression cassette arranged in 3' and in sense orientation and directly adjacent to the first expression cassette. The second expression cassette encodes a CAR having a binding domain that is specific for the $G_{D2}$ tumor antigen of glioblastoma cells. As generally preferred, also these nucleic acid constructs are devoid of a polyadenylation signal between the first expression cassette and the second expression cassette. FIG. 7A schematically shows the arrangement of elements of the nucleic acid constructs from 5' to 3', wherein the coding sequence for the effector molecule hTRAIL is depicted beneath the coding sequence for hIL21, schematically indicating that the hTRAIL encoding sequence is inserted in the same place as the hIL21 encoding sequence between the first promoter and the second expression cassette. These nucleic acid constructs contain flanking LTRs, a 5'SIN LTR and a 3'SIN LTR. The second expression cassette contains the PGK promoter, which controls constitutive expression of the $G_{D2}$-specific CAR ($G_{D2}$CAR). The nucleic acid sequence of the lentiviral vector encoding hIL21 is termed pCCL.PPT.NFATenhsyn.humanIL21co.PGK.CAR.PRE, the nucleic acid sequence is given in SEQ ID NO: 34, the nucleic acid sequence of the lentiviral vector encoding hTRAIL is termed pCCL.PPT.NFATenhsyn.TRAIL.PGK-.CAR.PRE, the nucleic acid sequence is given in SEQ ID NO: 35.

Human primary T-cells were transduced separately with one of the vectors shown in FIG. 7A, and the transduced T-cells were co-cultivated with or without $G_{D2}$ expressing human glioblastoma cells that were obtained from a patient and cultivated. After two days of co-cultivation of the glioblastoma cells with the T-cells that were transduced with the vector encoding hIL21, or of cultivation of the transduced T-cells alone, IL21 was determined by ELISA. In contrast to T-cells cultivated without glioblastoma cells or T-cells transduced with a vector that was devoid of the $G_{D2}$-CAR but contained only the first expression cassette encoding hIL21 cultivated in presence of or in absence of glioblastoma cells that were used as negative controls, the T-cells containing the vector according to the invention express hIL21 only in presence of glioblastoma cells. The results are shown in FIG. 7B, wherein n.d. denotes that hIL21 was not detectable in the controls, indicating that hIL21 was below detection levels.

For the T-cells that were transduced with the vector encoding hTRAIL as the effector molecule, intracellular TRAIL was analysed from collected cells by ELISA after 2 days, 6 days and after 9 days of co-cultivation with glioblastoma cells. As negative controls, the untransduced (Mock) T-cells alone and T-cells only (i.e. without glioblastoma coculture) transduced with the vector according to the invention with both the first (hTRAIL) and the second ($G_{D2}$-CAR) expression cassette were cultured. The ELISA results of cell lysates show that only the T-cells transduced with the vector according to the invention with both the first and the second expression cassettes produced hTRAIL, and only in presence of the glioblastoma cells. Expression of the exemplary effector molecule hTRAIL increased significantly over the time of the cultivation, namely at day 2 10 pg/mL, at day 6 84.7 pg/mL, at day 9 212.8 pg/mL. Results are shown in FIG. 7C, wherein n.d. denotes that hTRAIL was not detectable in the controls, indicating that hTRAIL was below detection levels.

EXAMPLE 6

Immune Cells Containing the Vector

Using EGFP as a representative for an effector molecule under the control of the first promoter and a second expression cassette expressing a $G_{D2}$-CAR in a nucleic acid construct according to the invention, NK-92 cells were transduced and co-cultivated with patient-derived glioblastoma cells expressing the target antigen $G_{D2,}$ and as a control without these stimulating cells. In one embodiment, the vector NFATsyn.EGFP-GD2CAR as the first promoter contained the Nasty promoter, in another embodiment, the vector NFATmIL2.EGFP-GD2CAR contained the NFAT-mIL2 promoter, and in a further embodiment the vector NFκBsyn.EGFP-GD2CAR contained the NFκBsyn promoter as the first promoter. These constructs contained the PGK promoter as the second promoter to constitutively express the CAR, and in 3' to the second expression cassette, which was arranged sense orientation in 3' to the first expression cassette, contained a wPRE and in 5' to the first expression cassette contained a packaging signal, an RRE and a PPT, the construct flanked by SIN LTRs, and except for the different first promoters, these nucleic acid constructs were identical.

Figure 8:
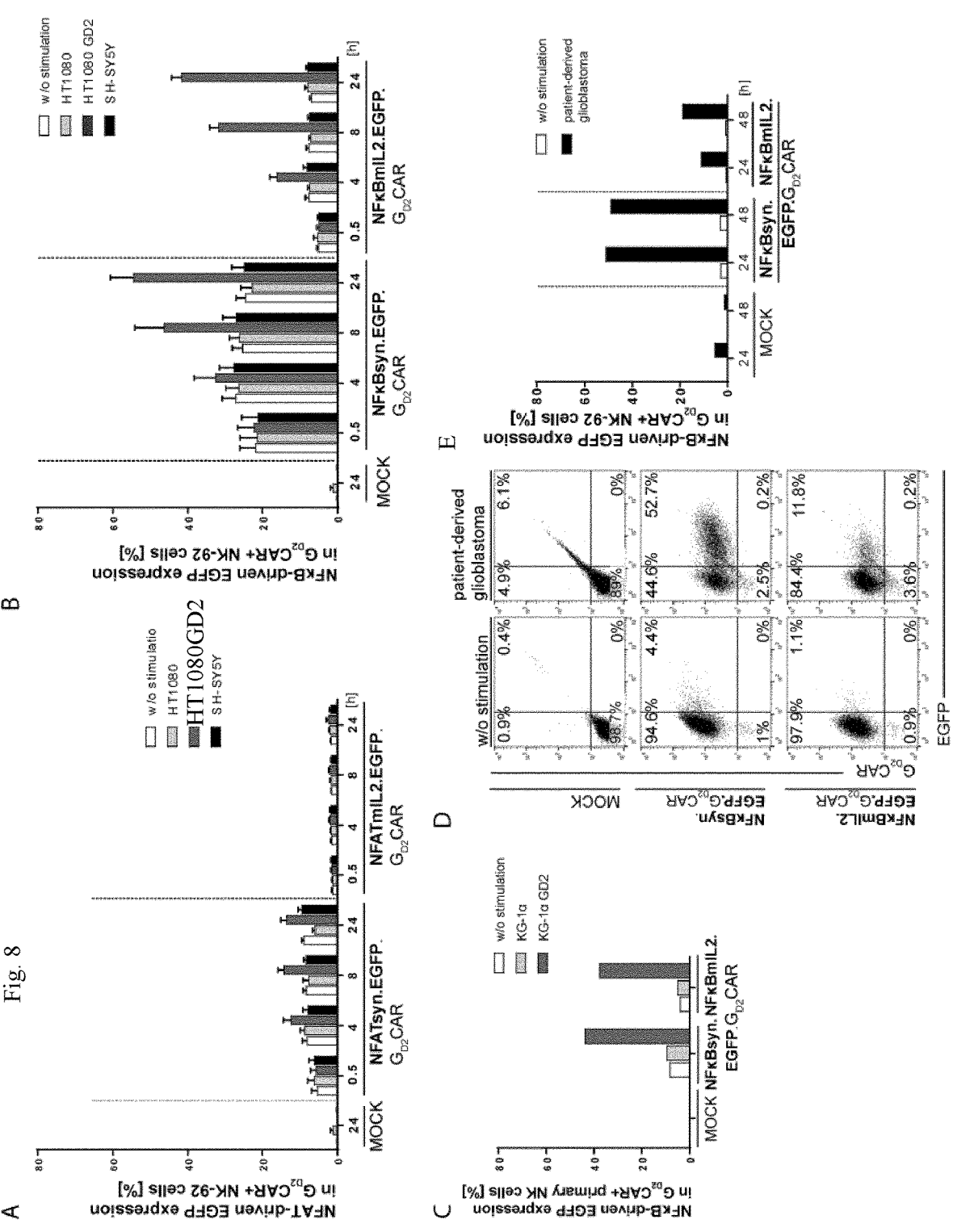

The results are shown in FIG. 8, wherein FIG. 8A shows a bar graph of a summary of flow cytometric analysis of unsorted NFATsyn.EGFP-GD2CAR- and NFATmIL2.EGFP-GD2CAR-modified (MOI 10) NK-92 cells after a 24 h-lasting co-culture with different target cells. GD2CAR-positive NK-92 cells were detected via antibody staining of scFv-CAR-region. Co-cultures were performed in a 10:1 effector:target (E:T; NK-92 cells:glioblastoma cells) ratio. Only a slight NFAT-driven EGFP expression after antigen recognition was detectable; (mean values±SD; n=3, biological replicates).

FIG. 8B shows a bar graph of a summary of flow cytometric analysis of EGFP upregulation in unsorted NFκBsyn.EGFP-GD2CAR-positive (MOI 10) NK-92 cells after co-culture with different target cells in a 10:1 effector: target (E:T) ratio for 24 h. GD2CAR-positive NK-92 cells were identified via antibody staining of scFv-CAR-region. A prominent EGFP expression was detected dependent on GD2-recognition of target cells in co-culture; (mean values±SD; n=5). In FIGS. 8A and 8B, the columns from left to right are without (w/o) stimulation, with stimulation by HT1080 (HT1080, negative comparison), with stimulation by HT1080 expressing GD2 (HT1080 GD2, positive), and stimulation by SH-SY5Y.

FIG. 8C shows a bar graph of a summary of flow cytometric analyses of a co-culture with modified primary NK cells and GD2-positive and GD2-negative suspension target cells after 24 h. Transduced (multiplicity of infection (MOI) 10) and unsorted primary NK cells of three different donors were co-cultivated with target cells in a 10:1 target: effector (T:E) ratio. GD$_2$CAR-positive primary NK cells were identified via antibody staining against CD56 and against the single chain variable fragment (scFv)-CAR-region. As a negative comparison KG-1α was used, for stimulation KG1α expressing GD$_2$ (KG1α G$_{D2}$). A clear inducible NFκB-driven EGFP expression was detected after antigen recognition.

FIG. 8D shows exemplary flow cytometric analyses (FACS) of a 24 h-lasting co-culture of sorted modified NK-92 cells with and without patient-derived primary glioblastoma cells. A specific EGFP upregulation was seen after tumor recognition. The bar graph of FIG. 8E shows a comparison of specific NFκB-driven EGFP upregulation after 24 h and 48 h.

These results show that immune cells containing the vector in the presence of cells that carry the target antigen of the CAR specifically produce the effector molecule that is encoded by the first expression cassette. Further, these results show that in immune cells containing the vector, the NFκBsyn promoter as the first promoter can be contained to generate a stronger expression of the effector molecule, and the NFATenhsyn promoter as the first promoter can be contained to generate a weaker expression of the effector molecule. Furthermore, the results show that the choice of the promoter in the first expression cassette can improve the expression of the inducible gene of interest and is dependent on the immune cell.

The invention claimed is:

1. A nucleic acid construct for expression of an effector molecule in response to the presence of a target antigen of a chimeric antigen receptor (CAR) or a T-cell receptor (TCR), wherein the nucleic acid construct in one strand comprises a first expression cassette, comprising a first promoter which is inducible by binding of a CAR or TCR to its target antigen to control expression of a coding sequence for the effector molecule, and a second expression cassette encoding the CAR or TCR under the control of a constitutive second promoter, wherein the nucleic acid construct is part of a lentiviral vector, of an alpha (α)-retroviral vector or of a gamma (γ)-retroviral vector, and wherein the first expression cassette is arranged in 5' of the second expression cassette, and wherein between the first expression cassette and the second expression cassette there is no poly-adenylation signal and wherein a poly-adenylation signal is contained in an LTR that is arranged in the 3' end of the second expression cassette.

2. The nucleic acid construct according to claim 1, wherein the first promoter is selected from the group consisting of SEQ ID NO: 1, SEQ ID NO: 2, SEQ ID NO: 3, and SEQ ID NO: 31.

3. The nucleic acid construct according claim 1, wherein the constitutive second promoter is selected from the group consisting of a PGK promoter having the nucleotide sequence of nucleotides No. 5158 . . . 5673 of SEQ ID NO: 8, an EF-1 alpha promoter having SEQ ID NO: 11, and an SFFV promoter having SEQ ID NO: 10.

4. The nucleic acid construct according to claim 1, wherein a WPRE is arranged at the 3' end of the CAR encoding sequence.

5. The nucleic acid construct according to claim 1, wherein the nucleic acid construct only contains a polyadenylation signal that is contained in an LTR that is arranged in the 3' end of the second expression cassette.

6. The nucleic acid construct according to claim 1, wherein a viral packaging signal is arranged in the 5' end of the first expression cassette.

7. The nucleic acid construct according to claim 1, wherein the first expression cassette encodes the effector molecule by SEQ ID NO: 4 or by SEQ ID NO: 6.

8. The nucleic acid construct according to-claim 1, wherein the arrangement of the first expression cassette and of the second expression cassette is arranged between a 5' LTR and a 3' SIN LTR.

9. The nucleic acid construct according to claim 8, wherein the LTR and SIN LTR elements are of lentiviral, of alpha-retroviral, or of gamma-retroviral origin.

10. The nucleic acid construct according to claim 8, wherein for expression in a production cell, the nucleic acid construct is under the control of a viral promoter for driving transcription of the genomic packageable viral mRNA.

11. The nucleic acid construct according to claim 8, wherein the nucleic acid construct is contained in a viral particle.

12. The nucleic acid construct according claim 8, wherein an intracytoplasmatic effector domain of the CAR comprises the intracellular effector domain of DAP12 or DAP10, or the intracytoplasmatic effector domain of the CAR comprises the CD3ζ domain.

13. An immune cell, containing a nucleic acid construct according to claim 1 for use in the treatment of cells expressing or presenting the target antigen of the CAR or TCR.

14. The immune cell according to claim 13 for use in the treatment of cells which are virus-infected cells or tumour cells, wherein the CAR is specific for a target antigen which is selected from viral antigens and tumour antigens, wherein the immune cell is a CD8+ (cytotoxic) T-cell, a primary NK-cell or NK T-cell, a NK92-cell, a macrophage, or a dendritic cell.

15. Immune The immune cell according to claim 13 for use in the treatment of an autoimmune disease or for use in the induction of tolerance for a target antigen, wherein the CAR is specific for the target antigen wherein the immune cell is a regulatory CD4+CD25+FOXP3+ regulatory T cell or an alternative immunomodulatory cell type, e.g. selected from NK cells, macrophages, double negative regulatory T cell and a mesenchymal stroma cell.

16. A process for producing an immune cell comprising the steps of providing an immune cell and introducing the nucleic acid construct according to claim 1 into the immune cell.

17. The process according to claim 16, wherein the immune cell originates from a patient, the nucleic acid construct is introduced into the immune cell in vitro, for producing an immune cell for use in the treatment of cells expressing or presenting the target antigen of the CAR or TCR in the patient.

18. A process for producing viral particles containing the nucleic acid construct according to-claim 1, comprising expressing the nucleic acid construct in a mammalian cell and co-expressing the viral structural proteins and replication enzymes (gag-pol), and the retroviral envelope protein (env), and optionally a rev protein.

19. The nucleic acid construct according to claim 10, wherein the viral promoter is selected from the group consisting of CMV promoter, RSV promoter, HIV promoter and MLV-derived promoters.

20. The nucleic acid construct of claim 12, wherein the intracytoplasmatic effector domain of the CAR further comprises an adjacent CD28 or 4-1BB domain.

* * * * *